US011116443B2

(12) United States Patent
Curtin

(10) Patent No.: US 11,116,443 B2
(45) Date of Patent: Sep. 14, 2021

(54) SYSTEMS AND METHODS FOR CLASSIFICATION AND TREATMENT OF DECUBITUS ULCERS

(71) Applicant: UNIVERSAL CARE SOLUTIONS, LLC, Wilmington, NC (US)

(72) Inventor: Candice Ganey Curtin, Wilmington, NC (US)

(73) Assignee: Universal Care Solutions, LLC, Wilmington, DE (US)

( * ) Notice: Subject to any disclaimer, the term of this patent is extended or adjusted under 35 U.S.C. 154(b) by 0 days.

(21) Appl. No.: 16/569,235

(22) Filed: Sep. 12, 2019

(65) Prior Publication Data
US 2020/0000398 A1 Jan. 2, 2020

Related U.S. Application Data

(63) Continuation of application No. 16/093,902, filed as application No. PCT/US2017/027983 on Apr. 17, 2017, now Pat. No. 10,448,881.
(Continued)

(51) Int. Cl.
*G06K 9/00* (2006.01)
*A61B 5/00* (2006.01)
(Continued)

(52) U.S. Cl.
CPC .............. *A61B 5/445* (2013.01); *A61B 5/107* (2013.01); *A61B 5/1455* (2013.01);
(Continued)

(58) Field of Classification Search
None
See application file for complete search history.

(56) References Cited

U.S. PATENT DOCUMENTS

2007/0259808 A1* 11/2007 Gans .................... A61K 9/0095
424/443
2010/0172567 A1* 7/2010 Prokoski ................ A61B 5/418
382/132
(Continued)

OTHER PUBLICATIONS

Notification of Transmittal of the International Search Report and the Written Opinion of the International Searching Authority, issued in International Application No. PCT/US2017/027983, dated Jun. 29, 2017; 10 pages.
(Continued)

*Primary Examiner* — Atiba O Fitzpatrick
(74) *Attorney, Agent, or Firm* — Morris, Manning & Martin, LLP; Daniel E. Sineway, Esq.

(57) ABSTRACT

Systems and methods for accurately and efficiently diagnosing, assessing, staging/grading/categorizing, and treating pressure ulcers, as well as preventing reverse staging of pressure ulcers, are disclosed. The system, in one embodiment, ensures that the rationale for the stage assigned to the patient will be in the patients' medical record. The system, in various embodiments, further suggests the pressure ulcer classification and allows the user to choose which classification terms should be used. In various embodiments, the system also allows for the different classification/staging system guidelines to be used, including the National Pressure Ulcer Advisory Panel (NPUAP) guidelines, the European Pressure Ulcer Advisory Panel Guidelines (EPUAP), the Pan Pacific Pressure Injury Alliance, CMS, WHO, and the MDS Guidelines.

24 Claims, 34 Drawing Sheets

Related U.S. Application Data

(60) Provisional application No. 62/323,365, filed on Apr. 15, 2016, provisional application No. 62/329,752, filed on Apr. 29, 2016.

(51) Int. Cl.
| | |
|---|---|
| *A61B 5/107* | (2006.01) |
| *A61B 5/1455* | (2006.01) |
| *G16H 30/20* | (2018.01) |
| *G06F 16/583* | (2019.01) |
| *G06T 7/00* | (2017.01) |

(52) U.S. Cl.
CPC .......... *A61B 5/4842* (2013.01); *A61B 5/7264* (2013.01); *G06F 16/5854* (2019.01); *G06T 7/0012* (2013.01); *G16H 30/20* (2018.01); *G06T 2207/10024* (2013.01); *G06T 2207/30088* (2013.01)

(56) References Cited

U.S. PATENT DOCUMENTS

| | | |
|---|---|---|
| 2012/0171652 A1 | 7/2012 | Sparks et al. |
| 2013/0331708 A1 | 12/2013 | Estocado |
| 2016/0296158 A1* | 10/2016 | Papazoglou ......... A61B 5/6886 |
| 2017/0079530 A1* | 3/2017 | DiMaio ................ A61B 5/0261 |
| 2017/0367580 A1* | 12/2017 | DiMaio ................ A61B 5/0064 |

OTHER PUBLICATIONS

Wound Ostomy and Continence Nurses Society, Position Statement: Pressure Ulcer Staging, Oct. 2007; 5 pages.

Haesler, E., Prevention and Treatment of Pressure Ulcers: Quick Reference Guide. Perth: Cambridge Media, 2014, 2nd Edition, ISBN-10 0-9579343-6-X; 75 pages.

Winnipeg Regional Health Authority, Pressure Ulcer Prevention and Treatment Clinical Practice Guideline, Nov. 2012; 83 pages.

* cited by examiner

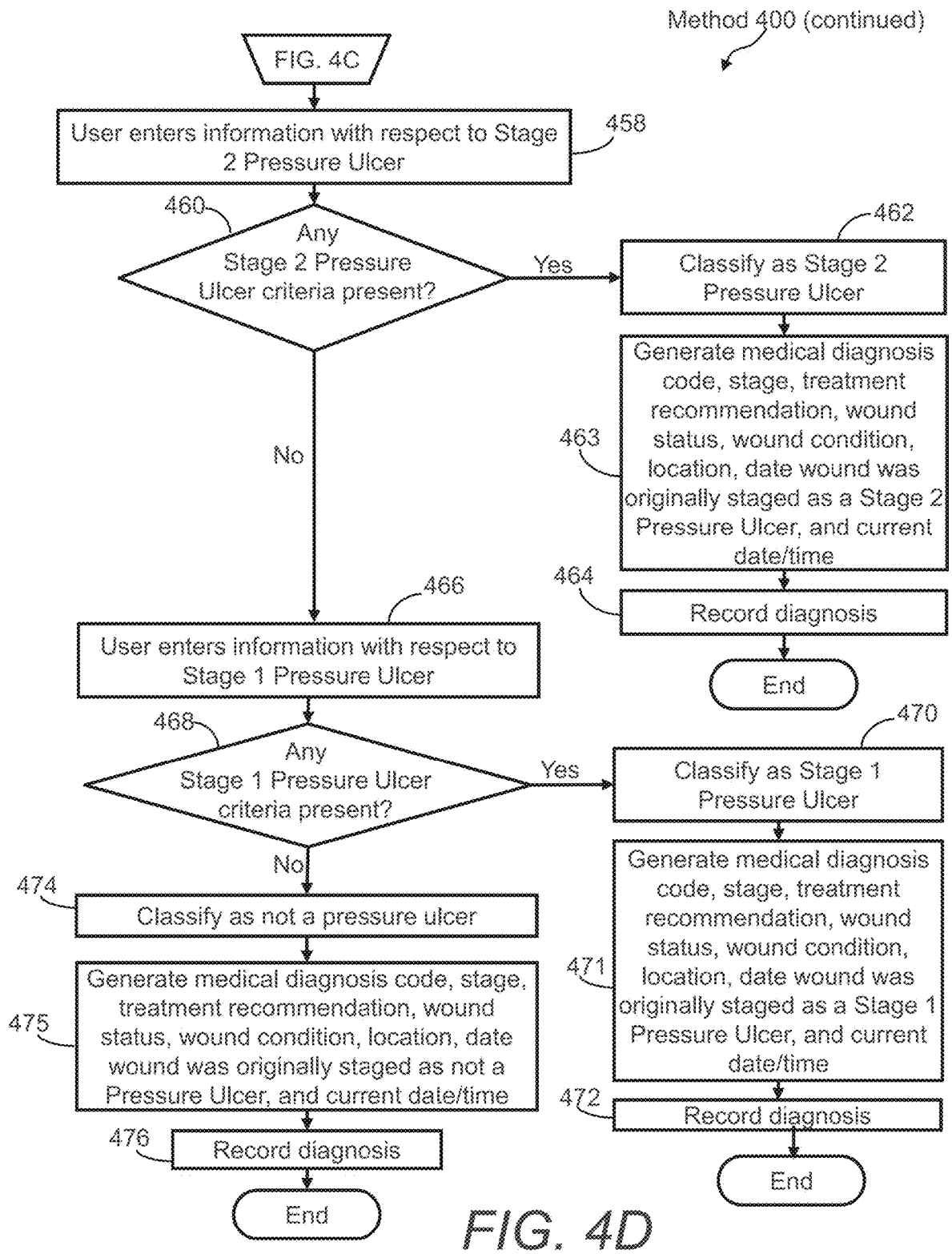

PUD GUI 118

Screen 515

Pressure Ulcer Diagnostic Tool

Patient: John Doe
Wound #2 – Right Heel Plantar Wound History

| | Assessment # | Override | Photo | Stage | Diagnosis Code | Date | Status | Condition |
|---|---|---|---|---|---|---|---|---|
| ☐ | 1 | No | No photo | Unstageable | L89.610 | 10/1/2016 | Active | Open |
| ☐ | 2 | No | No photo | Stage 3 | L89.613 | 2/1/2017 | Active | Open |
| ☐ | 3 | No | No photo | Stage 3 | L89.613 | 2/5/2017 | Active | Open |

[VIEW ASSESSMENT] [UPLOAD PHOTO] [MARK IN ERROR]

[BACK] [PRINT] [EXPORT]

*FIG. 8A*

PUD GUI 118

Screen 516

Pressure Ulcer Diagnostic Tool

Wound Assessment
Date: 10/20/2016

Question 1: Is this wound caused by pressure and/or pressure in conjunction with shear?
Answer 1: Yes
Question 2: Is or was any of the following visible, palpable, and/or true?
Answer 2: No
Question 3: Select the following statement if it is true:
Answer 3: No selection
Question 4: Is or was any of the following visible or true?
Answer 4: No
Question 5: Is any of the following currently visible?
Answer 5: No
Question 6: Is any of the following currently visible?
Answer 6: Intact blister

Diagnosis: Stage 2 Pressure Ulcer L89.012
Wound Status: Active
Wound Condition: Open

[PRINT]  [BACK]  [EXPORT]

*FIG. 8B*

PUD GUI 118

Screen 518

Pressure Ulcer Diagnostic Tool

Patient: John Doe
Left Upper Back

Is or Was any of the following visible, palpable, and/or true?
(Select all that apply)

| | | Visible | Palpable |
|---|---|---|---|
| | Bone | ☐ Visible | ☐ Palpable |
| | Muscle | ☐ Visible | ☐ Palpable |
| | Tendon | ☐ Visible | ☐ Palpable |
| | Ligament | ☐ Visible | ☐ Palpable |
| | Fascia | ☐ Visible | ☐ Palpable |
| | Cartilage | ☐ Visible | ☐ Palpable |
| | Joint Capsule | ☐ Visible | ☐ Palpable |
| | Other Supporting Structures | ☐ Visible | ☐ Palpable |

☐ This was previously classified as a Stage 4 Pressure Ulcer.

☐ This pressure ulcer is or was closed, resurfaced with scar tissue and/or epithelium, AND the last known stage was Unstageable or unknown.

[ CANCEL ]   [ BACK ]   [ CONTINUE ]

[ OVERRIDE ]

*FIG. 10A*

PUD GUI 118

Screen 518

Pressure Ulcer Diagnostic Tool

Patient: John Doe
Left Upper Back

Is or Was any of the following visible, palpable, and/or true?
(Select all that apply)

| | | Visible | Palpable |
|---|---|---|---|
| | Bone | ☐ Visible | ☐ Palpable |
| | Muscle | ☐ Visible | ☐ Palpable |
| | Tendon | ☐ Visible | ☐ Palpable |
| | Ligament | ☐ Visible | ☐ Palpable |
| | Fascia | ☐ Visible | ☐ Palpable |
| | Cartilage | ☐ Visible | ☐ Palpable |
| | Joint Capsule | ☐ Visible | ☐ Palpable |
| | Other Supporting Structures | ☐ Visible | ☐ Palpable |

☑ This was previously classified as a Stage 4 Pressure Ulcer.

☐ This pressure ulcer is or was closed, is or was resurfaced with scar tissue and/or epithelium, AND the last known stage was Unstageable or unknown.

[ CANCEL ]        [ BACK ]        [ CONTINUE ]

[ OVERRIDE ]

*FIG. 10B*

PUD GUI 118

Screen 518

Pressure Ulcer Diagnostic Tool

Patient: John Doe
Left Upper Back

Is or Was any of the following visible, palpable, and/or true?
(Select all that apply)

| | | Visible | Palpable |
|---|---|---|---|
| | Bone | ☐ Visible | ☐ Palpable |
| | Muscle | ☐ Visible | ☐ Palpable |
| | Tendon | ☐ Visible | ☐ Palpable |
| | Ligament | ☐ Visible | ☐ Palpable |
| | Fascia | ☐ Visible | ☐ Palpable |
| | Cartilage | ☐ Visible | ☐ Palpable |
| | Joint Capsule | ☐ Visible | ☐ Palpable |
| | Other Supporting Structures | ☐ Visible | ☐ Palpable |

☐ This was previously classified as a Stage 4 Pressure Ulcer.

☑ This pressure ulcer is or was closed, resurfaced with scar tissue and/or epithelium, AND the last known stage was Unstageable or unknown.

[ CANCEL ]   [ BACK ]   [ CONTINUE ]

[ OVERRIDE ]

*FIG. 10C*

PUD GUI 118

Screen 524

Pressure Ulcer Diagnostic Tool

Patient: John Doe
Left Upper Back

Is or Was any of the following visible or true?
(Select all that apply)

- ☐ Granulation Tissue
- ☐ Adipose or Fat Tissue
- ☐ Slough
- ☐ Eschar
- ☑ Tunneling
- ☐ Sinus Tract
- ☐ Undermining

- ☐ This wound was previously classified as an Unstageable
- ☑ This wound was previously classified as a Stage 3 Pres

1205

- Tunneling is a narrow opening or a passageway underneath the skin that extends through soft tissue and results in dead space with potential for abscess.

- Tunneling goes in one direction only.

optional photo shown here

OVERRIDE

*FIG. 12C*

PUD GUI 118

Screen 518

Pressure Ulcer Diagnostic Tool

Patient: John Doe
Left Upper Back

Is or Was any of the following visible, palpable, and/or true?
(Select all that apply)

| | | Visible | Palpable |
|---|---|---|---|
| | Bone | ☐ Visible | ☐ Palpable |
| | Muscle | ☐ Visible | ☐ Palpable |
| | Tendon | ☐ Visible | ☐ Palpable |
| | Ligament | ☐ Visible | ☐ Palpable |
| | Fascia | ☐ Visible | ☐ Palpable |
| | Cartilage | ☐ Visible | ☐ Palpable |
| | Joint Capsule | ☐ Visible | ☐ Palpable |
| | Other Supporting Structures | ☐ Visible | ☐ Palpable |

☐ This pressure ulcer is or was closed, is or was resurfaced with scar tissue and/or epithelium, AND the last known stage was Unstageable or unknown.

[CANCEL]  [BACK]  [CONTINUE]

[OVERRIDE]

*FIG. 19*

PUD Tool Accuracy Data

| # | Type of Clinician | Total Years of Nursing | Total Years of Hands on Care | Total Correct WITHOUT Tool | Total Correct WITH Tool | Total Staged Too Low | Total Staged Too High | Total that Would Show Declined | Years in Home Health | Years in Hospice | Years in Hospital | Years in Dialysis Center | Years in Doctors Office | Years in Private Duty | Years in Psych Facility | Years in Wound Clinic | Years in Other Work | Age Range | Sex |
|---|---|---|---|---|---|---|---|---|---|---|---|---|---|---|---|---|---|---|---|
| 1 | RN | 3 | 3 | 40% | 100% | 5 | 1 | 5 | 0 | 0 | 3 | 0 | 0 | 0 | 0 | 0 | 0 | 20-29 | F |
| 2 | RN | 7 | 7 | 60% | 100% | 4 | 0 | 4 | 0 | 0 | 7 | 0 | 0 | 0 | 0 | 0 | 0 | 40-49 | F |
| 3 | RN | 5 | 5 | 50% | 100% | 4 | 1 | 4 | 0 | 0 | 5 | 0 | 0 | 0 | 0 | 0 | 0 | 50-59 | M |
| 4 | RN | 31 | 31 | 20% | 100% | 5 | 3 | 5 | 1 | 0 | 10 | 0 | 0 | 0 | 20 | 0 | 0 | 60-69 | F |
| 5 | RN | 9 | 9 | 50% | 100% | 4 | 1 | 4 | 0 | 0 | 9 | 0 | 0 | 0 | 0 | 0 | 0 | 30-39 | F |
| 6 | RN | 38 | 25 | 20% | 100% | 5 | 3 | 5 | 10 | 10 | 10 | 0 | 0 | 0 | 3.5 | 0 | 16 | 60-69 | F |
| 7 | RN | 25 | 20 | 60% | 100% | 4 | 2 | 4 | 0 | 0 | 22 | 0 | 3 | 0 | 0 | 0 | 0 | 40-49 | F |
| 8 | RN | 30 | 30 | 60% | 100% | 4 | 0 | 4 | 0 | 0 | 30 | 0 | 0 | 0 | 0 | 0 | 0 | 60-69 | F |
| 9 | RN | 34 | 10 | 40% | 100% | 5 | 1 | 5 | 5 | 0 | 29 | 0 | 0 | 0 | 0 | 0 | 0 | 50-59 | F |
| 10 | RN | 19 | 19 | 50% | 100% | 5 | 0 | 5 | 0 | 0 | 19 | 0 | 0 | 0 | 0 | 0 | 0 | 40-49 | F |
| 11 | RN | 6 | 6 | 50% | 100% | 4 | 1 | 4 | 0 | 0 | 0 | 0 | 0 | 0 | 0 | 0 | 0 | 20-29 | F |
| 12 | RN | 21 | 13 | 50% | 100% | 4 | 1 | 4 | 19 | 0 | 2 | 0 | 0 | 0 | 0 | 0 | 0 | 40-49 | F |
| 13 | RN | 24 | 21 | 60% | 100% | 3 | 1 | 3 | 3 | 0 | 21 | 0 | 0 | 0 | 0 | 0 | 0 | 50-59 | F |
| 14 | RN | 10 | 8 | 70% | 100% | 3 | 0 | 3 | 2 | 0 | 8 | 0 | 0 | 0 | 0 | 0 | 0 | 30-39 | F |
| 15 | RN | 22 | 20 | 50% | 100% | 3 | 2 | 3 | 14 | 0 | 0 | 0 | 2 | 4 | 0 | 0 | 0 | 50-59 | F |
| 16 | LPN | 27 | 17 | 70% | 100% | 3 | 0 | 3 | 2 | 0 | 8 | 0 | 0 | 0 | 0 | 0 | 11 | 40-49 | F |
| 17 | RN | 9 | 9 | 40% | 100% | 5 | 1 | 5 | 0 | 0 | 9 | 0 | 3 | 0 | 0 | 0 | 0 | 30-39 | F |
| Totals | | 16.8 ave | 14.9 ave | 49.40% | 100% | 45 | 12 | 45 | 16 | 10 | 152 | 0 | 3 | 4 | 23.5 | 0 | 16 | | |

FIG. 24

SYSTEMS AND METHODS FOR CLASSIFICATION AND TREATMENT OF DECUBITUS ULCERS

CROSS REFERENCE TO RELATED APPLICATIONS

This application is a continuation of U.S. application Ser. No. 16/093,902, filed Oct. 15, 2018, entitled "Systems and Methods for Classification and Treatment of Decubitus Ulcers," which is a national phase application of, and claims the benefit of and priority to, International Application No. PCT/US2017/027983, filed Apr. 17, 2017, entitled "Systems and Methods for Classification and Treatment of Decubitus Ulcers," which claims the benefits of and priority to U.S. Provisional Patent Application No. 62/323,365, filed Apr. 15, 2016, and entitled "Pressure Ulcer Assessment (PUA) System, Computer Application, and Methods," and U.S. Provisional Patent Application No. 62/329,752, filed Apr. 29, 2016, and entitled "Pressure Ulcer Assessment (PUA) System, Computer Application, and Methods," all of which are incorporated herein by reference in their entireties.

TECHNICAL FIELD

The present systems and methods relate generally to classification of decubitus ulcers and, more particular, to diagnosis, assessment, staging/grading/categorizing, and treatment of decubitus ulcers.

BACKGROUND

Healthcare providers (e.g., physicians, nurses, therapists, certified wound care specialists, certified wound care nurses, etc.) use an international classification system to classify and code symptoms and diagnoses of decubitus ulcers (also referred to as "pressure ulcers," "bedsores," "pressure sores," etc.). The pressure ulcer classification system and treatment guidelines comprise six classifications maintained by the National Pressure Ulcer Advisory Panel (e.g., "NPUAP") and the European Pressure Ulcer Advisory Panel (e.g., "EPUAP"). The classifications, which may be referred to as "stages", "grades", or "categories" depending on the geographic area in which a healthcare provider practices, indicate the severity of the pressure ulcer and may also dictate what treatment is needed, what type(s) of medical equipment the patient is eligible for, as well as, the final medical diagnosis code (which determines the payment given to the healthcare provider). Therefore, diagnosing/ classifying pressure ulcers incorrectly may lead to inappropriate medical treatment, improper insurance payments, a misuse of medical resources, and it may negatively affect overall clinical, financial, and legal outcomes.

Classifying pressure ulcers to determine the correct diagnosis and medical diagnosis code (also referred to as "staging," "grading," or "categorizing") is extremely complicated as it requires such extensive clinical knowledge that even experts trained in wound care do not stage pressure ulcers accurately all of the time. To stage a pressure ulcer, a healthcare provider physically assesses a wound and peri-wound to determine whether the ulcer satisfies the defined standards of a particular stage of pressure ulcer, according to the classifications, as well as consulting the patient's medical record to obtain necessary information from the patient's chart and/or from their previous healthcare provider(s). Despite many grants offered and multiple medical community requests, the healthcare community has not yet developed effective tools to assist providers with classifying pressure ulcers. No tools currently exist that accurately classify pressure ulcers and prevent mistakes commonly made, such as reverse staging (e.g., reducing the severity of the classification of a pressure ulcer that cannot be reduced).

Therefore, there is a long-felt but unresolved need for a system or method that assists with accurate and efficient diagnosis, assessment, staging, and treatment of pressure ulcers.

BRIEF SUMMARY OF THE DISCLOSURE

Briefly described, and according to one embodiment, aspects of the present disclosure generally relate to systems and methods for accurately and efficiently diagnosing, assessing, staging, and treating pressure ulcers.

Pressure ulcers may be classified, for example, as a Stage/Grade/Category 1, 2, 3, and/or 4 Pressure Ulcer, an Unstageable Pressure Ulcer, and/or a Deep Tissue Injury. Pressure ulcers may also be classified as a Resurfaced Full-thickness Pressure Ulcer of unspecified stage when it is known that there was a pre-existing full-thickness pressure ulcer (e.g., either a Stage/Grade/Category 4 or 3 or Unstageable Pressure Ulcer) was present at one time but not enough information is present to determine which one of those three classifications it had been. Of all the pressure ulcer classifications, in various embodiments, a Stage/Grade/Category 1 is the least severe, whereas a Stage/Grade/Category 4 is the most severe. The severity of an Unstageable Pressure Ulcer, a Deep Tissue Injury, and a Resurfaced Full-thickness Pressure Ulcer is generally unknown but may be able to be later classified and has the possibility to evolve to as high as a Stage/Grade/Category 4. Those skilled in the art will appreciate that the term pressure ulcer as used herein is synonymous with the terms pressure injury, decubitus ulcer, and bedsore; that the term stage as used herein is synonymous with the terms grade and category; that the term Deep Tissue Injury ("DTI") as used herein is synonymous with the terms Deep Tissue Pressure Injury, Suspected Deep Tissue Injury ("SDTI"), and Suspected Deep Tissue Pressure Injury; and that the term Unstageable Pressure Ulcer as used herein is synonymous with the terms Unclassified Pressure Ulcer and Ungradable Pressure Ulcer, all of which are consistent with changes recently announced by the NPUAP in 2016, as well as the International Pressure Ulcer Guidance from the NPUAP, EPUAP, the PPPIA (Pan Pacific Pressure Injury Alliance), CMS (Center for Medicare and Medicaid Services), and the WHO (World Health Organization).

Conventionally, a pressure ulcer is classified by a healthcare provider determining if any prior classification of the wound exists. Then, the provider would physically assess whether the suspected pressure ulcer is open or closed. From there, the provider would proceed stepwise by comparing the current tissue status of the pressure ulcer with the current definitions of the stage of pressure ulcers as defined by their determining organization to see which stage the pressure ulcer fits into, if any (e.g., bearing in mind that, currently, Resurfaced Full-thickness Pressure Ulcer is not an option listed directly in any staging system, though it is expected that a clinician should recognize that this could potentially be an option).

By contrast, in one embodiment, the presently disclosed pressure ulcer diagnostic (PUD) clinical decision support system first determines if the wound in question is actually caused by pressure, and, if so, then determines whether the pressure ulcer is or has ever been classified as a Stage/Grade/ Category 4, and then whether the pressure ulcer is or has ever been classified as, in one embodiment in the following order, a Stage 4, a Resurfaced Full-thickness Pressure Ulcer, an Unstageable Pressure Ulcer, a Stage 3, a Deep Tissue Injury, a Stage 2, a Stage 1, and not a pressure ulcer, systematically ruling out each category in a hierarchal approach/order.

In various embodiments, the PUD system does not permit reverse staging/classifying of pressure ulcers (e.g., diagnosing a pressure ulcer that has been previously diagnosed as a full-thickness pressure ulcer to either a less severe full-thickness pressure ulcer, such as going from a Stage 4 to a Stage 3, a partial thickness pressure ulcer, such as a Stage 1 or a Stage 2, and/or to a Deep Tissue Injury).

Advantageously, embodiments of the PUD tool of the PUD system and of the networked PUD system—

(1) ensure accurate diagnosis of Stage 4 Pressure Ulcers and prevent reverse staging of Stage 4 Pressure Ulcers to a Resurfaced Full-thickness Pressure Ulcer, Unstageable Pressure Ulcer, Stage 3 Pressure Ulcer, Deep Tissue Injury, Stage 2 Pressure Ulcer, Stage 1 Pressure Ulcer, as not a pressure ulcer, or as a healed pressure ulcer that is no longer present once a pressure ulcer has been determined at any time to be classified as a Stage 4 Pressure Ulcer;

(2) ensure accurate diagnosis of Resurfaced Full-thickness Pressure Ulcers and prevent reverse staging of Resurfaced Full-thickness Pressure Ulcers to an Unstageable Pressure Ulcer, a Stage 3 Pressure Ulcer, Stage 2 Pressure Ulcer, Stage 1 Pressure Ulcer, as not a pressure ulcer at all, or as a healed pressure ulcer, while still allowing the ability for the Resurfaced Full-thickness Pressure Ulcer to become a Stage 4 Pressure Ulcer if the pressure ulcer is determined as such at any subsequent given time.

(3) ensure accurate diagnosis of Unstageable Pressure Ulcers and prevent reverse staging of Unstageable Pressure Ulcers to a Deep Tissue Injury, Stage 2 Pressure Ulcer, Stage 1 Pressure Ulcer, as not a pressure ulcer, or as a healed pressure ulcer, while still allowing the Unstageable Pressure Ulcer to become a Stage 3 Pressure Ulcer, a Resurfaced Full-thickness Pressure Ulcer, or a Stage 4 Pressure Ulcer, if the pressure ulcer is determined as such at any subsequent given time;

(4) ensure accurate diagnosis of Stage 3 Pressure Ulcers and prevent reverse staging of Stage 3 Pressure Ulcers to a Deep Tissue Injury (DTI), Stage 2 Pressure Ulcer, Stage 1 Pressure Ulcer, as not a pressure ulcer, or as a healed pressure ulcer, while still allowing the Stage 3 Pressure Ulcer to become a Resurfaced Full-thickness Pressure Ulcer, Unstageable Pressure Ulcer, or a Stage 4 Pressure Ulcer if the pressure ulcer is determined as such at any subsequent time;

(5) ensure accurate diagnosis of Deep Tissue Injuries;

(6) ensure accurate diagnosis of Stage 2 Pressure Ulcers;

(7) ensure accurate diagnosis of Stage 1 Pressure Ulcers;

(8) ensure accurate diagnosis of a healed pressure ulcer;

(9) ensure that a wound that does not have the characteristics or symptoms of one of the seven pressure ulcer classifications is not diagnosed as a pressure ulcer; and

(10) ensure the appropriate medical diagnosis code is assigned to a pressure ulcer.

The correct staging/classifying referenced in item (5) above, in various embodiments, will be determined even when there is a Stage 2 or Stage 1 Pressure Ulcer characteristic or symptom present. For example, if a blister is present (ruptured or intact) regardless of the type of fluid the blister did contain, if there are any characteristics or symptoms of a Deep Tissue Injury, then this will be classified as a Deep Tissue Injury. Additionally, the system still allows for a Deep Tissue Injury to be later classified as a Stage 2 Pressure Ulcer if: 1) there are no longer any characteristics or symptoms of a DTI; and 2) there is at least one characteristic or symptom of a Stage 2 Pressure Ulcer present. In one embodiment, the system will still allow for a Deep Tissue Injury to be later classified as a Stage 1 Pressure Ulcer if: 1) no characteristics or symptoms of a DTI are present; 2) no characteristics or symptoms of a Stage 2 Pressure Ulcer are present; and 3) there is at least one characteristic or symptom of a Stage 1 Pressure Ulcer present. In one embodiment, the system will still allow for a Deep Tissue Injury to be classified as not a pressure ulcer if: 1) there are no longer any characteristics or symptoms of a Deep Tissue Injury present; 2) no Stage 2 Pressure Ulcer characteristics or symptoms are present; and 3) no Stage 1 Pressure Ulcer characteristics or symptoms are present, then this would no longer be classified as a pressure ulcer but would be considered healed. The system, in various embodiments, will allow for a DTI to be classified as a Stage 4 Pressure Ulcer, Stage 3 Pressure Ulcer, Unstageable Pressure Ulcer, and/or a Resurfaced Full-thickness Pressure Ulcer, at any later given time, if any of those characteristics or symptoms are present, even if evidence of a DTI is currently or was ever present. For example, if characteristics or symptoms of a DTI and a Stage 4 Pressure Ulcer are present simultaneously, the system would classify the wound as a Stage 4 Pressure Ulcer; In another example of this embodiment, if there are no characteristics or symptoms of a Stage 4 Pressure Ulcer present and there are characteristics or symptoms of a DTI and a Resurfaced Full-thickness Pressure Ulcer present simultaneously, then the system would classify the wound as a Resurfaced Full-thickness Pressure Ulcer; In another example, if there are no characteristics or symptoms of a Stage 4 Pressure Ulcer or a Resurfaced Full-thickness Pressure Ulcer present and there are characteristics or symptoms of an Unstageable Pressure Ulcer present, then the system would classify the wound as a Unstageable Pressure Ulcer. In another example, if there are no characteristics or symptoms of a Stage 4 Pressure Ulcer, a Resurfaced Full-thickness Pressure Ulcer, or an Unstageable Pressure Ulcer present and there are characteristics or symptoms of a DTI and a Stage 3 Pressure Ulcer present simultaneously, then the system would classify the wound as a Stage 3 Pressure Ulcer. Additionally, in another example, is if there are no characteristics or symptoms of a Stage 4 Pressure Ulcer, a Resurfaced Full-thickness Pressure Ulcer, an Unstageable Pressure Ulcer, or a Stage 3 Pressure Ulcer present and there are characteristics or symptoms of a DTI and a Stage 2 Pressure Ulcer present simultaneously, then the system would classify the wound as a Deep Tissue Injury (rather than the Stage 2 Pressure Ulcer). In another example, is if there are no characteristics or symptoms of a Stage 4 Pressure Ulcer, a Resurfaced Full-thickness Pressure Ulcer, an Unstageable Pressure Ulcer, a Stage 3 Pressure Ulcer, or a Stage 2 Pressure Ulcer present and there are characteristics or symptoms of a DTI and a Stage 1 Pressure Ulcer present simultaneously, then the system would classify the wound as a Deep Tissue Injury (rather than the Stage 1 Pressure Ulcer).

In one embodiment, a method of classifying decubitus ulcers, comprising the steps of: determining whether one or more Stage 4 criteria are presented by a particular wound; if the one or more Stage 4 criteria are presented, classifying the particular wound as a Stage 4 decubitus ulcer and generating a recommended treatment corresponding to the Stage 4 classification for the particular wound; if the one or more Stage 4 criteria are not presented, determining whether one or more Resurfaced Full-Thickness criteria are presented by the particular wound; if the one or more Resurfaced Full-Thickness criteria are presented, classifying the particular wound as a Resurfaced Full-Thickness decubitus ulcer and generating a recommended treatment corresponding to the Resurfaced Full-Thickness classification for the particular wound; if the one or more Resurfaced Full-Thickness criteria are not presented, determining whether one or more Unstageable criteria are presented by the particular wound; if the one or more Unstageable criteria are presented, classifying the particular wound as an Unstageable decubitus ulcer and generating a recommended treatment corresponding to the Unstageable classification for the particular wound; if the one or more Unstageable criteria are not presented, determining whether one or more Stage 3 criteria are presented by the particular wound; if the one or more Stage 3 criteria are presented, classifying the particular wound as a Stage 3 decubitus ulcer and generating a recommended treatment corresponding to the Stage 3 classification for the particular wound; if the one or more Stage 3 criteria are not presented, determining whether one or more Deep Tissue Injury criteria are presented by the particular wound; if the one or more Deep Tissue Injury criteria are presented, classifying the particular wound as a Deep Tissue Injury and generating a recommended treatment corresponding to the Deep Tissue Injury classification for the particular wound; if the one or more Deep Tissue Injury criteria are not presented, determining whether one or more Stage 2 criteria are presented by the particular wound; if the one or more Stage 2 criteria are presented, classifying the particular wound as a Stage 2 decubitus ulcer and generating a recommended treatment corresponding to the Stage 2 classification for the particular wound; if the one or more Stage 2 criteria are not presented, determining whether one or more Stage 1 criteria are presented by the particular wound; if the one or more Stage 1 criteria are presented, classifying the particular wound as a Stage 1 decubitus ulcer and generating a recommended treatment corresponding to the Stage 1 classification for the particular wound; and if the one or more Stage 1 criteria are not presented, taking a predetermined action with respect to the particular wound.

In one embodiment, a system for classifying decubitus ulcers, comprising: a data store; and a processor operatively connected to the data store, wherein the processor is operative to: determine whether one or more Stage 4 criteria are presented by a particular wound; if the one or more Stage 4 criteria are presented, classify the particular wound as a Stage 4 decubitus ulcer, generate a recommended treatment corresponding to the Stage 4 classification for the particular wound, and store the Stage 4 classification and the recommended treatment corresponding to the Stage 4 classification in the data store; if the one or more Stage 4 criteria are not presented, determine whether one or more Resurfaced Full-Thickness criteria are presented by the particular wound; if the one or more Resurfaced Full-Thickness criteria are presented, classify the particular wound as a Resurfaced Full-Thickness decubitus ulcer, generate a recommended treatment corresponding to the Resurfaced Full-Thickness classification for the particular wound, and store the Resurfaced Full-Thickness classification and the recommended treatment corresponding to the Resurfaced Full-Thickness classification in the data store; if the one or more Resurfaced Full-Thickness criteria are not presented, determine whether one or more Unstageable criteria are presented by the particular wound; if the one or more Unstageable criteria are presented, classify the particular wound as an Unstageable decubitus ulcer, generate a recommended treatment corresponding to the Unstageable classification for the particular wound, and store the Unstageable classification and the recommended treatment corresponding to the Unstageable classification in the data store; if the one or more Unstageable criteria are not presented, determine whether one or more Stage 3 criteria are presented by the particular wound; if the one or more Stage 3 criteria are presented, classify the particular wound as a Stage 3 decubitus ulcer, generate a recommended treatment corresponding to the Stage 3 classification for the particular wound, and store the Stage 3 classification and the recommended treatment corresponding to the Stage 3 classification in the data store; if the one or more Stage 3 criteria are not presented, determine whether one or more Deep Tissue Injury criteria are presented by the particular wound; if the one or more Deep Tissue Injury criteria are presented, classify the particular wound as a Deep Tissue Injury, generate a recommended treatment corresponding to the Deep Tissue Injury classification for the particular wound, and store the Deep Tissue Injury classification and the recommended treatment corresponding to the Deep Tissue Injury classification in the data store; if the one or more Deep Tissue Injury criteria are not presented, determine whether one or more Stage 2 criteria are presented by the particular wound; if the one or more Stage 2 criteria are presented, classify the particular wound as a Stage 2 decubitus ulcer, generate a recommended treatment corresponding to the Stage 2 classification for the particular wound, and store the Stage 2 classification and the recommended treatment corresponding to the Stage 2 classification in the data store; if the one or more Stage 2 criteria are not presented, determine whether one or more Stage 1 criteria are presented by the particular wound; if the one or more Stage 1 criteria are presented, classify the particular wound as a Stage 1 decubitus ulcer, generate a recommended treatment corresponding to the Stage 1 classification for the particular wound, and store the Stage 1 classification and the recommended treatment corresponding to the Stage 3 classification in the data store; and if the one or more Stage 1 criteria are not presented, take a predetermined action with respect to the particular wound.

In one embodiment, a method of classifying decubitus ulcers, comprising the steps of: determining whether one or more criteria of a first stage/grade/category decubitus ulcer are presented by a particular wound; if the one or more criteria of the first stage/grade/category decubitus ulcer are presented, classifying the particular wound as the first stage/grade/category decubitus ulcer and generating a recommended treatment corresponding to the first stage/grade/category for the particular wound; if the one or more criteria of a first stage/grade/category decubitus ulcer are not presented, determining whether one or more criteria of a second stage/grade/category decubitus ulcer are presented by the particular wound; if the one or more criteria of the second stage/grade/category decubitus ulcer are presented, classifying the particular wound as the second stage/grade/category decubitus ulcer and generating a recommended treatment corresponding to the second stage/grade/category for the particular wound; and if the one or more criteria of the second stage/grade/category decubitus ulcer are not presented, taking a predetermined action with respect to the particular wound.

In one embodiment, a system for classifying decubitus ulcers, comprising: a data store; and a processor operatively connected to the data store, wherein the processor is operative to: determine whether one or more criteria of a first stage/grade/category decubitus ulcer are presented by a particular wound; if the one or more criteria of the first stage/grade/category decubitus ulcer are presented, classify the particular wound as the first stage/grade/category decubitus ulcer, generate a recommended treatment corresponding to the first stage/grade/category for the particular wound, and store the first stage/grade/category classification and the recommended treatment corresponding to the first stage/grade/category in the data store; if the one or more criteria of a first stage/grade/category decubitus ulcer are not presented, determine whether one or more criteria of a second stage/grade/category decubitus ulcer are presented by the particular wound; if the one or more criteria of the second stage/grade/category decubitus ulcer are presented, classify the particular wound as the second stage/grade/category decubitus ulcer, generate a recommended treatment corresponding to the second stage/grade/category for the particular wound, and store the second stage/grade/category classification and the recommended treatment corresponding to the second stage/grade/category in the data store; and if the one or more criteria of the second stage/grade/category decubitus ulcer are not presented, take a predetermined action with respect to the particular wound.

In one embodiment, a method of classifying decubitus ulcers, comprising the steps of: determining the previous classification of a particular wound; determining, in a predefined order of decreasing severity based on the determined previous classification, which one or more symptoms the particular wound presents; and generating, based the determined one or more symptoms and the determined previous classification, a current classification and recommended treatment corresponding to the particular wound.

In one embodiment, a system for classifying decubitus ulcers, comprising: a data store; and a processor operatively connected to the data store, wherein the processor is operative to: determine the previous classification of a particular wound; determine, in a predefined order of decreasing severity based on the determined previous classification, which one or more symptoms the particular wound presents; and generate, based the determined one or more symptoms and the determined previous classification, a current classification and recommended treatment corresponding to the particular wound.

In one embodiment, a method of preventing reverse staging of decubitus ulcers, comprising the steps of: determining the previous classification of a particular wound; determining only whether the particular wound presents one or more symptoms of one or more classifications of decubitus ulcers that are at least as severe as the determined previous classification; and generating, based on the determined one or more symptoms and the previous classification, a current classification and recommended treatment corresponding to the particular wound.

In one embodiment, a system for preventing reverse staging of decubitus ulcers, comprising: a data store; and a processor operatively connected to the data store, wherein the processor is operative to: determine the previous classification of a particular wound; determine only whether the particular wound presents one or more symptoms of one or more classifications of decubitus ulcers that are at least as severe as the determined previous classification; and generate, based on the determined one or more symptoms and the previous classification, a current classification and recommended treatment corresponding to the particular wound.

According to one aspect of the present disclosure, the method, wherein the one or more Stage 4 criteria comprise whether any of the following are visible in, palpable in, or true of the particular wound: bone, muscle, tendon, ligament, cartilage, fascia, joint capsule, other supporting structures, or the particular wound was previously classified as a Stage 4 decubitus ulcer. Furthermore, the method, wherein the one or more Resurfaced Full-Thickness criteria comprise whether: the particular wound is or was closed, is or was resurfaced with scar tissue or epithelium, and the particular wound was previously classified as Unstageable or Unknown. Moreover, the method, wherein the one or more Unstageable criteria comprise whether: slough, eschar, or a non-removable dressing is obscuring a portion of the particular wound such that an extent of tissue loss cannot be determined. Further, the method, wherein the one or more Stage 3 criteria comprise whether any of the following are visible in, palpable in, or true of the particular wound: adipose tissue, granulation tissue, slough, eschar, sinus tract, tunneling, or undermining. Additionally, the method, wherein the one or more Deep Tissue Injury criteria comprise whether any of the following are visible in, palpable in, or true of the particular wound: blood filled blisters; ruptured blisters surrounded by or adjacent to discolored purple, maroon, or deep red intact skin; intact blister surrounded by or adjacent to non-blanching discolored purple, maroon, or deep red intact skin; intact and non-intact non-blanching discolored purple, maroon, or deep red skin; or skin surrounding or adjacent to the particular wound is non-blanching and discolored purple, maroon, or deep red. Also, the method, wherein the one or more Stage 2 criteria comprise whether any of the following is currently visible in the particular wound: intact blisters, ruptured blisters, or shallow opened wounds with exposed dermis.

According to one aspect of the present disclosure, the method, wherein the one or more Stage 1 criteria comprise whether intact skin with non-blanching erythema is currently visible in the particular wound. Furthermore, the method, wherein the predetermined action comprises classifying the particular wound as not a decubitus ulcer. Moreover, the method, wherein determining whether the one or more Stage 4 criteria are presented by the particular wound further comprises the steps of: receiving a digital image of the particular wound; analyzing the digital image of the particular wound to identify one or more decubitus ulcer criteria; comparing the identified one or more decubitus ulcer criteria to the one or more Stage 4 criteria to determine whether the identified one or more decubitus ulcer criteria match the one or more Stage 4 criteria; and if at least one of the identified one or more decubitus ulcer criteria match the one or more Stage 4 criteria, determining that the one or more Stage 4 criteria are presented by the particular wound.

According to one aspect of the present disclosure, the system, wherein the one or more Stage 4 criteria comprise whether any of the following are visible in, palpable in, or true of the particular wound: bone, muscle, tendon, ligament, cartilage, fascia, joint capsule, other supporting structures, or the particular wound was previously classified as a Stage 4 decubitus ulcer. Further, the system, wherein the one or more Resurfaced Full-Thickness criteria comprise whether: the particular wound is or was closed, is or was resurfaced with scar tissue or epithelium, and the particular wound was previously classified as Unstageable or Unknown. Additionally, the system, wherein the one or more Unstageable criteria comprise whether: slough, eschar, or a non-removable dressing is obscuring a portion of the particular wound such that an extent of tissue loss cannot be determined. Also, the system, wherein the one or more Stage 3 criteria comprise whether any of the following are visible in, palpable in, or true of the particular wound: adipose tissue, granulation tissue, slough, eschar, sinus tract, tunneling, or undermining. Furthermore, the system, wherein the one or more Deep Tissue Injury criteria comprise whether any of the following are visible in, palpable in, or true of the particular wound: blood filled blisters; ruptured blisters surrounded by or adjacent to discolored purple, maroon, or deep red intact skin; intact blister surrounded by or adjacent to non-blanching discolored purple, maroon, or deep red intact skin; intact and non-intact non-blanching discolored purple, maroon, or deep red skin; or skin surrounding or adjacent to the particular wound is non-blanching and discolored purple, maroon, or deep red. Moreover, the system, wherein the one or more Stage 2 criteria comprise whether any of the following is currently visible in the particular wound: intact blisters, ruptured blisters, or shallow opened wounds with exposed dermis.

According to one aspect of the present disclosure, the system, wherein the one or more Stage 1 criteria comprise whether intact skin with non-blanching erythema is currently visible in the particular wound. Further, the system, wherein. to take the predetermined action, the processor is further operative to classify the particular wound as not a decubitus ulcer and store the not a decubitus ulcer classification in the data store. Additionally, the system, further comprising an image capture device that is operatively connected to the data store and the processor, wherein to determine whether the one or more Stage 4 criteria are presented by the particular wound, the processor is further operative to: receive a digital image of the particular wound from the image capture device; analyze the digital image of the particular wound to identify one or more decubitus ulcer criteria; compare the identified one or more decubitus ulcer criteria to the one or more Stage 4 criteria to determine whether the identified one or more decubitus ulcer criteria match the one or more Stage 4 criteria; and if at least one of the identified one or more decubitus ulcer criteria match the one or more Stage 4 criteria, determine that the one or more Stage 4 criteria are presented by the particular wound.

According to one aspect of the present disclosure, the method, wherein the predetermined action further comprises a first predetermined action, and wherein the first predetermined action comprises the steps of: determining whether one or more criteria of a third stage/grade/category decubitus ulcer are presented by the particular wound; if the one or more criteria of the third stage/grade/category decubitus ulcer are presented, classifying the particular wound as the third stage/grade/category decubitus ulcer and generating a recommended treatment corresponding to the third stage/grade/category for the particular wound; and if the one or more criteria of the third stage/grade/category decubitus ulcer are not presented, taking a second predetermined action with respect to the particular wound. Also, the method, wherein the first stage/grade/category decubitus ulcer comprises a Stage 4 decubitus ulcer, the second stage/grade/category decubitus ulcer comprises a Resurfaced Full-Thickness decubitus ulcer, and the third stage/grade/category decubitus ulcer comprises an Unstageable decubitus ulcer. Furthermore, the method, wherein the first stage/grade/category decubitus ulcer comprises a Resurfaced Full-Thickness decubitus ulcer, the second stage/grade/category decubitus ulcer comprises an Unstageable decubitus ulcer, and the third stage/grade/category decubitus ulcer comprises a Stage 3 decubitus ulcer. Moreover, the method, wherein the first stage/grade/category decubitus ulcer comprises an Unstageable decubitus ulcer, the second stage/grade/category decubitus ulcer comprises a Stage 3 decubitus ulcer, and the third stage/grade/category decubitus ulcer comprises a Deep Tissue Injury. Further, the method, wherein the first stage/grade/category decubitus ulcer comprises a Stage 3 decubitus ulcer, the second stage/grade/category decubitus ulcer comprises a Deep Tissue Injury decubitus ulcer, and the third stage/grade/category decubitus ulcer comprises a Stage 2 decubitus ulcer. Additionally, the method, wherein the first stage/grade/category decubitus ulcer comprises a Deep Tissue Injury, the second stage/grade/category decubitus ulcer comprises a Stage 2 decubitus ulcer, and the third stage/grade/category decubitus ulcer comprises a Stage 1 decubitus ulcer. Also, the method, wherein the second predetermined action comprises classifying the particular wound as not a decubitus ulcer.

According to one aspect of the present disclosure, the system, wherein the predetermined action further comprises a first predetermined action, and wherein, to take the first predetermined action, the processor is further operative to: determine whether one or more criteria of a third stage/grade/category decubitus ulcer are presented by the particular wound; if the one or more criteria of the third stage/grade/category decubitus ulcer are presented, classify the particular wound as the third stage/grade/category decubitus ulcer, generate a recommended treatment corresponding to the third stage/grade/category for the particular wound, and store the third stage/grade/category classification and the recommended treatment corresponding to the third stage/grade/category in the data store; and if the one or more criteria of the third stage/grade/category decubitus ulcer are not presented, take a second predetermined action with respect to the particular wound. Furthermore, the system, wherein the first stage/grade/category decubitus ulcer comprises a Stage 4 decubitus ulcer, the second stage/grade/category decubitus ulcer comprises a Resurfaced Full-Thickness decubitus ulcer, and the third stage/grade/category decubitus ulcer comprises an Unstageable decubitus ulcer. Moreover, the system, wherein the first stage/grade/category decubitus ulcer comprises a Resurfaced Full-Thickness decubitus ulcer, the second stage/grade/category decubitus ulcer comprises an Unstageable decubitus ulcer, and the third stage/grade/category decubitus ulcer comprises a Stage 3 decubitus ulcer. Further, the system, wherein the first stage/grade/category decubitus ulcer comprises an Unstageable decubitus ulcer, the second stage/grade/category decubitus ulcer comprises a Stage 3 decubitus ulcer, and the third stage/grade/category decubitus ulcer comprises a Deep Tissue Injury. Additionally, the system, wherein the first stage/grade/category decubitus ulcer comprises a Stage 3 decubitus ulcer, the second stage/grade/category decubitus ulcer comprises a Deep Tissue Injury decubitus ulcer, and the third stage/grade/category decubitus ulcer comprises a Stage 2 decubitus ulcer. Also, the system, wherein the first stage/grade/category decubitus ulcer comprises a Deep Tissue Injury, the second stage/grade/category decubitus ulcer comprises a Stage 2 decubitus ulcer, and the third stage/grade/category decubitus ulcer comprises a Stage 1 decubitus ulcer. Furthermore, the system, wherein, to take the second predetermined action, the processor is further operative to classify the particular wound as not a decubitus ulcer and store the not a decubitus ulcer classification in the data store.

According to one aspect of the present disclosure, the method, wherein the determined previous classification comprises a Stage 4 decubitus ulcer; the one or more symptoms comprise whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and the current classification comprises the Stage 4 decubitus ulcer. Moreover, the method, wherein the determined previous classification comprises a Resurfaced Full-Thickness decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown. Further, the method, wherein the determined previous classification comprises an Unstageable decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined. Additionally, the method, wherein the determined previous classification comprises a Stage 3 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining.

According to one aspect of the present disclosure, the method, wherein the determined previous classification comprises a Deep Tissue Injury and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red. Also, the method, wherein the determined previous classification comprises a Stage 2 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red; and then whether any of the following is currently visible in the particular wound: intact blisters, ruptured blisters, or shallow opened wounds with exposed dermis. Furthermore, the method, wherein the determined previous classification comprises a Stage 1 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red; and then whether any of the following is currently visible in the particular wound: intact blisters, ruptured blisters, or shallow opened wounds with exposed dermis; and then whether intact skin with non-blanching erythema is currently visible in the particular wound.

According to one aspect of the present disclosure, the system, wherein the determined previous classification comprises a Stage 4 decubitus ulcer; the one or more symptoms comprise whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and the current classification comprises the Stage 4 decubitus ulcer. Moreover, the system, wherein the determined previous classification comprises a Resurfaced Full-Thickness decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown. Further, the system, wherein the determined previous classification comprises an Unstageable decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined. Additionally, the system, wherein the determined previous classification comprises a Stage 3 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining.

According to one aspect of the present disclosure, the system, wherein the determined previous classification comprises a Deep Tissue Injury and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red. Also, the system, wherein the determined previous classification comprises a Stage 2 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red; and then whether any of the following is currently visible in the particular wound: intact blisters, ruptured blisters, or shallow opened wounds with exposed dermis. Furthermore, the system, wherein the determined previous classification comprises a Stage 1 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red; and then whether any of the following is currently visible in the particular wound: intact blisters, ruptured blisters, or shallow opened wounds with exposed dermis; and then whether intact skin with non-blanching erythema is currently visible in the particular wound.

According to one aspect of the present disclosure, the method, wherein the previous classification of the particular wound comprises a Stage 4 decubitus ulcer and the one or more classifications of decubitus ulcers that are at least as severe as the determined previous classification comprises the Stage 4 decubitus ulcer. Moreover, the method, wherein the previous classification of the particular wound comprises a Resurfaced Full-Thickness decubitus ulcer and the one or more classifications of decubitus ulcers that are at least as severe as the determined previous classification comprise the Resurfaced Full-Thickness decubitus ulcer and a Stage 4 decubitus ulcer. Further, the method, wherein the previous classification of the particular wound comprises an Unstageable decubitus ulcer and the one or more classifications of decubitus ulcers that are at least as severe as the determined previous classification comprise the Unstageable decubitus ulcer, a Resurfaced Full-Thickness decubitus ulcer, and a Stage 4 decubitus ulcer. Additionally, the method, wherein the previous classification of the particular wound comprises a Stage 3 decubitus ulcer and the one or more classifications of decubitus ulcers that are at least as severe as the determined previous classification comprise the Stage 3 decubitus ulcer, an Unstageable decubitus ulcer, a Resurfaced Full-Thickness decubitus ulcer, and a Stage 4 decubitus ulcer. Also, the method, wherein the previous classification of the particular wound comprises a Deep Tissue Injury and the one or more classifications of decubitus ulcers that are at least as severe as the determined previous classification comprise the Deep Tissue Injury, a Stage 3 decubitus ulcer, an Unstageable decubitus ulcer, a Resurfaced Full-Thickness decubitus ulcer, and a Stage 4 decubitus ulcer. Furthermore, the method, wherein the previous classification of the particular wound comprises a Stage 2 decubitus ulcer and the one or more classifications of decubitus ulcers that are at least as severe as the determined previous classification comprise the Stage 2 decubitus ulcer, a Deep Tissue Injury, a Stage 3 decubitus ulcer, an Unstageable decubitus ulcer, a Resurfaced Full-Thickness decubitus ulcer, and a Stage 4 decubitus ulcer. Moreover, the method, wherein the previous classification of the particular wound comprises a Stage 1 decubitus ulcer and the one or more classifications of decubitus ulcers that are at least as severe as the determined previous classification comprise the Stage 1 decubitus ulcer, a Stage 2 decubitus ulcer, a Deep Tissue Injury, a Stage 3 decubitus ulcer, an Unstageable decubitus ulcer, a Resurfaced Full-Thickness decubitus ulcer, and a Stage 4 decubitus ulcer.

According to one aspect of the present disclosure, the system, wherein the previous classification of the particular wound comprises a Stage 4 decubitus ulcer and the one or more classifications of decubitus ulcers that are at least as severe as the determined previous classification comprises the Stage 4 decubitus ulcer. Further, the system, wherein the previous classification of the particular wound comprises a Resurfaced Full-Thickness decubitus ulcer and the one or more classifications of decubitus ulcers that are at least as severe as the determined previous classification comprise the Resurfaced Full-Thickness decubitus ulcer and a Stage 4 decubitus ulcer. Additionally, the system, wherein the previous classification of the particular wound comprises an Unstageable decubitus ulcer and the one or more classifications of decubitus ulcers that are at least as severe as the determined previous classification comprise the Unstageable decubitus ulcer, a Resurfaced Full-Thickness decubitus ulcer, and a Stage 4 decubitus ulcer. Also, the system, wherein the previous classification of the particular wound comprises a Stage 3 decubitus ulcer and the one or more classifications of decubitus ulcers that are at least as severe as the determined previous classification comprise the Stage 3 decubitus ulcer, an Unstageable decubitus ulcer, a Resurfaced Full-Thickness decubitus ulcer, and a Stage 4 decubitus ulcer. Furthermore, the system, wherein the previous classification of the particular wound comprises a Deep Tissue Injury and the one or more classifications of decubitus ulcers that are at least as severe as the determined previous classification comprise the Deep Tissue Injury, a Stage 3 decubitus ulcer, an Unstageable decubitus ulcer, a Resurfaced Full-Thickness decubitus ulcer, and a Stage 4 decubitus ulcer. Moreover, the system, wherein the previous classification of the particular wound comprises a Stage 2 decubitus ulcer and the one or more classifications of decubitus ulcers that are at least as severe as the determined previous classification comprise the Stage 2 decubitus ulcer, a Deep Tissue Injury, a Stage 3 decubitus ulcer, an Unstageable decubitus ulcer, a Resurfaced Full-Thickness decubitus ulcer, and a Stage 4 decubitus ulcer. Further, the system, wherein the previous classification of the particular wound comprises a Stage 1 decubitus ulcer and the one or more classifications of decubitus ulcers that are at least as severe as the determined previous classification comprise the Stage 1 decubitus ulcer, a Stage 2 decubitus ulcer, a Deep Tissue Injury, a Stage 3 decubitus ulcer, an Unstageable decubitus ulcer, a Resurfaced Full-Thickness decubitus ulcer, and a Stage 4 decubitus ulcer.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 8 (consisting of FIGS. 8A and 8B) is a screenshot of an exemplary wound history screen of a PUD system, according to one embodiment of the present disclosure;

FIG. 10 (consisting of FIGS. 10A, 10B, and 10C) is a screenshot of an exemplary Stage 4 wound classification screen of a PUD system, according to one embodiment of the present disclosure;

FIG. 19 is a screenshot of an alternative exemplary Stage 4 wound classification screen of a PUD system, according to one embodiment of the present disclosure;

FIG. 24 shows data demonstrating that the presently disclosed PUD system and tool are capable of diagnosing pressure injuries with 100% accuracy in contrast to conventional methods which are not even half as accurate.

DETAILED DESCRIPTION

Figure 1:
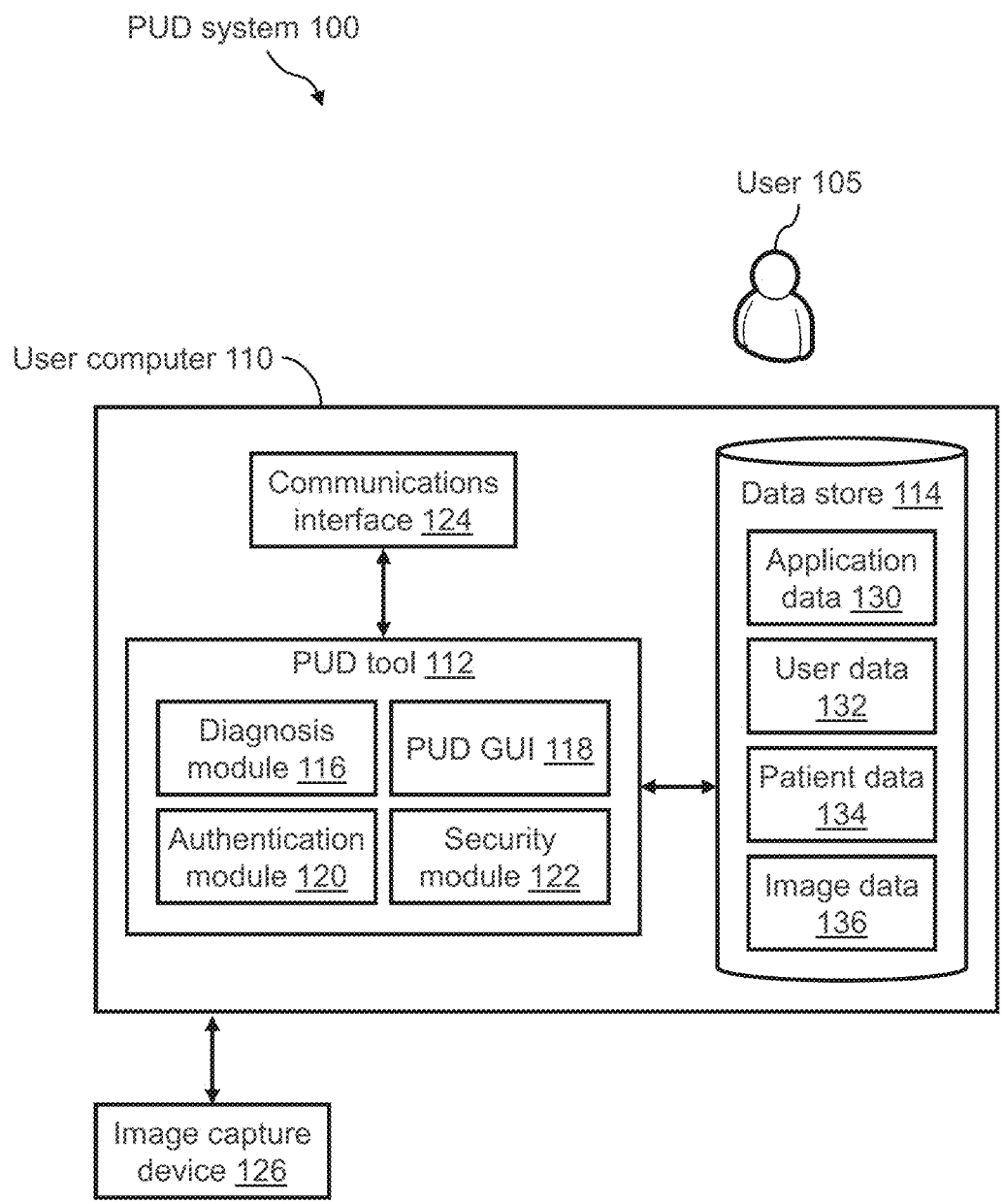
FIG. 1 illustrates a high-level overview of an exemplary pressure ulcer diagnostic clinical decision support ("PUD") system, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to systems and methods for accurately and efficiently diagnosing, assessing, staging, and treating pressure ulcers.

Pressure ulcers may be classified, for example, as a Stage/Grade/Category 1, 2, 3, and/or 4 Pressure Ulcer, an Unstageable Pressure Ulcer, and/or a Deep Tissue Injury. Pressure ulcers may also be classified as a Resurfaced Full-thickness Pressure Ulcer of unspecified stage when it is known that there was a pre-existing full-thickness pressure ulcer (e.g., either a Stage/Grade/Category 4 or 3 or Unstageable Pressure Ulcer) was present at one time but not enough information is present to determine which one of those three classifications it had been. Of all the pressure ulcer classifications, in various embodiments, a Stage/Grade/Category 1 is the least severe, whereas a Stage/Grade/Category 4 is the most severe. The severity of an Unstageable Pressure Ulcer, a Deep Tissue Injury, and a Resurfaced Full-thickness Pressure Ulcer is generally unknown but may be able to be later classified and has the possibility to evolve to as high as a Stage/Grade/Category 4. Those skilled in the art will appreciate that the term pressure ulcer as used herein is synonymous with the terms pressure injury, decubitus ulcer, and bedsore; that the term stage as used herein is synonymous with the terms grade and category; that the term Deep Tissue Injury ("DTI") as used herein is synonymous with the terms Deep Tissue Pressure Injury, Suspected Deep Tissue Injury ("SDTI"), and Suspected Deep Tissue Pressure Injury; and that the term Unstageable Pressure Ulcer as used herein is synonymous with the terms Unclassified Pressure Ulcer and Ungradable Pressure Ulcer, all of which are consistent with changes recently announced by the NPUAP in 2016, as well as the International Pressure Ulcer Guidance from the EPUAP, the PPPIA, CMS, and the WHO.

Conventionally, a pressure ulcer is classified by a healthcare provider determining if any prior classification of the wound exists. Then, the provider would physically assess whether the suspected pressure ulcer is open or closed. From there, the provider would proceed stepwise by comparing the current tissue status of the pressure ulcer with the current definitions of the stage of pressure ulcers as defined by their determining organization to see which stage the pressure ulcer fits into, if any (e.g., bearing in mind that, currently, Resurfaced Full-thickness Pressure Ulcer is not an option listed directly in any staging system, though it is expected that a clinician should recognize that this could potentially be an option).

By contrast, in one embodiment, the presently disclosed pressure ulcer diagnostic (PUD) clinical decision support system first determines whether the pressure ulcer is or has ever been classified as a Stage/Grade/Category 4, and then whether the pressure ulcer is or has ever been classified as, in one embodiment in the following order, a Resurfaced Full-thickness Pressure Ulcer, an Unstageable Pressure Ulcer, a Stage 3, a Deep Tissue Injury, a Stage 2, a Stage 1, and not a pressure ulcer, systematically ruling out each category in a hierarchal approach/order.

In various embodiments, the PUD system does not permit reverse staging/classifying of pressure ulcers (e.g., diagnosing a pressure ulcer that has been previously diagnosed as a full-thickness pressure ulcer to either a less severe full-thickness pressure ulcer, such as going from a Stage 4 to a Stage 3, a partial thickness pressure ulcer, such as a Stage 1 or a Stage 2, and/or to a Deep Tissue Injury).

Advantageously, embodiments of the PUD tool of the PUD system and of the networked PUD system—

(1) ensure accurate diagnosis of Stage 4 Pressure Ulcers and prevent reverse staging of Stage 4 Pressure Ulcers to a Resurfaced Full-thickness Pressure Ulcer, Unstageable Pressure Ulcer, Stage 3 Pressure Ulcer, Deep Tissue Injury, Stage 2 Pressure Ulcer, Stage 1 Pressure Ulcer, as not a pressure ulcer, or as a healed pressure ulcer that is no longer present once a pressure ulcer has been determined at any time to be classified as a Stage 4 Pressure Ulcer;

(2) ensure accurate diagnosis of Resurfaced Full-thickness Pressure Ulcers and prevent reverse staging of Resurfaced Full-thickness Pressure Ulcers to an Unstageable Pressure Ulcer, a Stage 3 Pressure Ulcer, Stage 2 Pressure Ulcer, Stage 1 Pressure Ulcer, as not a pressure ulcer at all, or as a healed pressure ulcer, while still allowing the ability for the Resurfaced Full-thickness Pressure Ulcer to become a Stage 4 Pressure Ulcer if the pressure ulcer is determined as such at any subsequent given time.

(3) ensure accurate diagnosis of Unstageable Pressure Ulcers and prevent reverse staging of Unstageable Pressure Ulcers to a Deep Tissue Injury, Stage 2 Pressure Ulcer, Stage 1 Pressure Ulcer, as not a pressure ulcer, or as a healed pressure ulcer, while still allowing the Unstageable Pressure Ulcer to become a Stage 3 Pressure Ulcer, a Resurfaced Full-thickness Pressure Ulcer, or a Stage 4 Pressure Ulcer, if the pressure ulcer is determined as such at any subsequent given time;

(4) ensure accurate diagnosis of Stage 3 Pressure Ulcers and prevent reverse staging of Stage 3 Pressure Ulcers to a Deep Tissue Injury (DTI), Stage 2 Pressure Ulcer, Stage 1 Pressure Ulcer, as not a pressure ulcer, or as a healed pressure ulcer, while still allowing the Stage 3 Pressure Ulcer to become a Resurfaced Full-thickness Pressure Ulcer, Unstageable Pressure Ulcer, or a Stage 4 Pressure Ulcer if the pressure ulcer is determined as such at any subsequent time;

(5) ensure accurate diagnosis of Deep Tissue Injuries;

(6) ensure accurate diagnosis of Stage 2 Pressure Ulcers;

(7) ensure accurate diagnosis of Stage 1 Pressure Ulcers;

(8) ensure accurate diagnosis of a healed pressure ulcer;

(9) ensure that a wound that does not have the characteristics or symptoms of one of the seven pressure ulcer classifications is not diagnosed as a pressure ulcer; and

(10) ensure the appropriate medical diagnosis code is assigned to a pressure ulcer.

The correct staging/classifying referenced in item (5) above, in various embodiments, will be prevented even when there is a Stage 2 Pressure Ulcer characteristic or symptom present. For example, if a blister is present (ruptured or intact) regardless of the type of fluid the blister did contain, if there are any characteristics or symptoms of a Deep Tissue Injury, then this will be classified as a Deep Tissue Injury. Additionally, the system still allows for a Deep Tissue Injury to be later classified as a Stage 2 Pressure Ulcer if: 1) there are no longer any characteristics or symptoms of a DTI; and 2) there is at least one characteristic or symptom of a Stage 2 Pressure Ulcer present. In one embodiment, the system will still allow for a Deep Tissue Injury to be later classified as a Stage 1 Pressure Ulcer if: 1) no characteristics or symptoms of a DTI are present; 2) no characteristics or symptoms of a Stage 2 Pressure Ulcer are present; and 3) there is at least one characteristic or symptom of a Stage 1 Pressure Ulcer present. In one embodiment, the system will still allow for a Deep Tissue Injury to be classified as not a pressure ulcer if: 1) there are no longer any characteristics or symptoms of a Deep Tissue Injury present; 2) no Stage 2 Pressure Ulcer characteristics or symptoms are present; and 3) no Stage 1 Pressure Ulcer characteristics or symptoms are present, then this would no longer be classified as a pressure ulcer but would be considered healed. The system, in various embodiments, will allow for a DTI to be classified as a Stage 4 Pressure Ulcer, Stage 3 Pressure Ulcer, Unstageable Pressure Ulcer, and/or a Resurfaced Full-thickness Pressure Ulcer, at any later given time, if any of those characteristics or symptoms are present, even if evidence of a DTI is currently or was ever present. For example, if characteristics or symptoms of a DTI and a Stage 4 Pressure Ulcer are present simultaneously, the system would classify the wound as a Stage 4 Pressure Ulcer; In another example of this embodiment, if there are no characteristics or symptoms of a Stage 4 Pressure Ulcer present and there are characteristics or symptoms of a DTI and a Resurfaced Full-thickness Pressure Ulcer present simultaneously, then the system would classify the wound as a Resurfaced Full-thickness Pressure Ulcer; In another example, if there are no characteristics or symptoms of a Stage 4 Pressure Ulcer or a Resurfaced Full-thickness Pressure Ulcer present and there are characteristics or symptoms of an Unstageable Pressure Ulcer present, then the system would classify the wound as a Unstageable Pressure Ulcer. In another example, if there are no characteristics or symptoms of a Stage 4 Pressure Ulcer, a Resurfaced Full-thickness Pressure Ulcer, or an Unstageable Pressure Ulcer present and there are characteristics or symptoms of a DTI and a Stage 3 Pressure Ulcer present simultaneously, then the system would classify the wound as a Stage 3 Pressure Ulcer. Additionally, in another example, is if there are no characteristics or symptoms of a Stage 4 Pressure Ulcer, a Resurfaced Full-thickness Pressure Ulcer, an Unstageable Pressure Ulcer, or a Stage 3 Pressure Ulcer present and there are characteristics or symptoms of a DTI and a Stage 2 Pressure Ulcer present simultaneously, then the system would classify the wound as a Deep Tissue Injury (rather than the Stage 2 Pressure Ulcer). In another example, is if there are no characteristics or symptoms of a Stage 4 Pressure Ulcer, a Resurfaced Full-thickness Pressure Ulcer, an Unstageable Pressure Ulcer, a Stage 3 Pressure Ulcer, or a Stage 2 Pressure Ulcer present and there are characteristics or symptoms of a DTI and a Stage 1 Pressure Ulcer present simultaneously, then the system would classify the wound as a Deep Tissue Injury (rather than the Stage 1 Pressure Ulcer).

Exemplary Embodiments

Referring now to the figures, for the purposes of example and explanation of the fundamental processes and components of the disclosed systems and methods, reference is made to FIG. 1, which illustrates an exemplary, high-level overview of one embodiment of the pressure ulcer diagnostic (PUD) clinical decision support system 100. As will be understood and appreciated, the exemplary, high-level overview shown in FIG. 1 represents merely one approach or embodiment of the PUD system 100, and other aspects are used according to various embodiments of the present system.

Generally, a user 105 (e.g., healthcare practitioner, clinician, machine/robot, individual who is qualified/trained/programmed to perform a pressure ulcer diagnostic, etc.) may operate the PUD system 100 to classify one or more pressure ulcers on a particular patient. For example, in one embodiment, prior to physically assessing a particular pressure ulcer, the user 105 may assess the patient's past medical history to determine whether the pressure ulcer has been previously classified and, if so, what treatment it received. In various embodiments, the user 105 removes the dressing from the ulcer wound bed and periwound area and cleans the wound bed and periwound area. The user 105 generally accesses the PUD system 100, launching and logging into the PUD tool 112. After selecting the appropriate patient in the PUD tool 112, in one embodiment, the user 105 may enter the location (e.g., elbow, ankle, back, buttock, etc.) of the patient's wound bed into the PUD tool 112.

In various embodiments, the PUD tool 112 guides and directs the user 105 through the classification of the particular pressure ulcer, including, in certain steps of the diagnostic process, requesting that the user 105 physically palpate the wound bed (and the periwound area). In one embodiment, the user 105 takes one or more digital photos of the wound bed. The PUD system 100 may, in one embodiment, automatically analyze the digital photos to determine the appropriate classification for the wound. In one embodiment, the PUD system 100 may store the digital photos for later reference.

After classification, in one embodiment, the wound bed and the periwound (partially or in whole) is treated and redressed. It should be appreciated that the particular treatment applied to the wound may vary depending, for example, on the stage of the pressure ulcer diagnosed, the treatment guidelines followed by the particular health care facility in which the patient's pressure ulcer is being diagnosed, and the like. In one embodiment, the PUD system 100 may provide instructions/recommendations on how to treat the wound, based on the classification given to the wound.

In various embodiments, the PUD system 100 may be any computing device (e.g., desktop computer, laptop, servers, tablets, etc.), combination of computing devices, software, hardware, combination of software and hardware, database (e.g., stored in the cloud or on premise, structured as relational, etc.), or combination of databases that is capable of performing the functionality disclosed herein. Generally, the PUD system 100 is configured as a standalone computing device, which further comprises a PUD tool 112 for accurately diagnosing pressure ulcers. For example, in one embodiment, the PUD system 100 comprises a user computer 110 that the further comprises the PUD tool 112, a data store 114, and a communications interface 124. Additionally, in one embodiment, an image capture device 126 may be connected to user computer 110. The image capture device 126 may be, for example, any digital camera (e.g., standalone, or as a component of a smartphone, computer, and/or tablet, etc.), thermal imaging device, digital Planimetry image device, or webcam. In some embodiments, the image capture device 126 is integrated with the user computer 110, for example, a smartphone, tablet, or laptop that is equipped with a digital camera. The PUD tool 112 comprises, for example, a diagnosis module 116, a PUD graphical user interface (GUI) 118, an authentication module 120, and a security module 122. Stored in the data store 114 is, for example, application data 130, user data 132, patient data 134, and image data 136.

Generally, a user 105 is associated with the PUD system 100. In the PUD system 100, in various embodiments, the user 105 may be any healthcare practitioner, clinician, machine/robot, or individual who is qualified/trained/programmed to perform a pressure ulcer diagnostic. Of course, the user of the presently disclosed subject matter is not intended to be limited in any way, and could further comprise a caregiver, a patient, educator, an auditor, insurance agent, and the like. The user computer 110, in various embodiments, may be any computing device, such as, but not limited to, a desktop computer, a laptop computer, a handheld computing device, a mobile phone (or smart phone), and/or a tablet device.

The user 105 may use the PUD GUI 118 to interact with the PUD tool 112. The PUD tool 112 is a computer application that may be implemented as a web application and run in a web browser, such as Internet Explorer®. However, the PUD tool 112 may be implemented by other means, such as a .NET application, a desktop application, a mobile app, an application program interface (API), and the like.

The PUD tool 112 is a software application by which pressure ulcers may be accurately classified. In particular, the diagnosis module 116 manages the overall operations of the PUD tool 112 with respect to performing pressure ulcer diagnostics. The operations of the diagnosis module 116 may be informed by information stored in application data 130, wherein the information stored in application data 130 may be informed by the NPUAP, EPUAP, PPPIA, or organizations of the like (such as Center of Medicare and Medicaid Services, the World Health Organization, etc.). Currently, according to the NPUAP, a pressure ulcer "is a localized ulcer to the skin and/or underlying tissue usually over a bony prominence, as a result of pressure, or pressure in combination with shear. A number of contributing or confounding factors are also associated with pressure ulcers; the significance of these factors is yet to be elucidated" (NPUAP, 2014). The latest 2016 definition from the NPUAP states, "A pressure ulcer is localized damage to the skin and/or underlying soft tissue usually over a bony prominence or related to a medical or other device. The ulcer may present as intact skin or an open ulcer and may be painful. The ulcer occurs as a result of intense and/or prolonged pressure or pressure in combination with shear. The tolerance of soft tissue for pressure and shear may also be affected by microclimate, nutrition, perfusion, co-morbidities and condition of the soft tissue." (See, e.g., National Pressure Ulcer Advisory Panel. Updated Pressure Ulcer Stages. Retrieved from http://www.npuap.org/pr2.htm. Accessed April, 2016). Those skilled in the art will appreciate that although the latest definitions have been published by the NPUAP, the existing definitions will remain in place until the changes go into effect with all national agencies, such as Center of Medicare and Medicaid Services (CMS) and the World Health Organization (WHO). As such, the presently disclosed subject matter contemplates utilizing whichever definitions are in effect. To that end, it is to be understood that although many of the figures show the existing definitions, the systems and methods presently disclosed may be readily adapted to comprise the latest definitions, as well as any future changes to the definitions of pressure ulcers or injuries. As used herein currently, "latest NPUAP definition", "latest definition" and the like, refers to the NPUAP definitions released in April 2016. However, the term "latest definition" and similar terms will change to reflect future definitional changes publicized by NPUAP, EPUAP, PPPIA, CMS, WHO, and/or other governing organizations with the authority to determine medical diagnostic definitions.

Depending on the country, there are generally six main pressure ulcer classifications/stages used in conventional methods of diagnosing pressure ulcers: (1) category/stage/grade 1: non-blanchable redness (of intact skin); (2) category/stage/grade 2: partial thickness skin loss or blister; (3)

category/stage/grade 3: full thickness skin and tissue loss; (4) category/stage/grade 4: full thickness (skin and) tissue loss; (5) unstageable/unclassified: full thickness skin or tissue loss—depth unknown, obscured full-thickness skin and tissue loss; and, in some countries, (6) suspected deep tissue injury/deep tissue pressure injury—depth unknown, persistent non-blanchable deep red, maroon or purple discoloration. A seventh category is not defined in the classification definitions set forth currently by the NPUAP, EPUAP, and PPPIA but was recognized and established by the Wound and Ostomy Continence Nurse (WOCN) Society as a "resurfaced full-thickness pressure ulcer of undetermined full-thickness depth."

The WOCN society is a professional, international nursing society of more than 5,000 experts in the care of patients with wound, ostomy, and incontinence, who many align with their current vision statement as being "the trusted global authority and leader in wound, ostomy, and continence care" (See "About Us." Retrieved online March 2017, http://wocn.org/?page=about_us). In the WOCN Positon Statement: Pressure Ulcer Staging, it is explained that when the original depth of a pressure ulcer is unknown and it is resurfaced, with contracted scar tissue (or epithelium) present, the healed pressure ulcer should be described as evidence of a resurfaced full-thickness pressure ulcer or evidence of a full thickness pressure ulcer of undetermined full-thickness depth" (WOCN, pg. 2, March 2017). Pressure ulcers that were once full-thickness but are now or have been resurfaced with epithelium or scar tissue (otherwise known as closed or healed) prior to being classified as either a Stage 4 or a Stage 3 Pressure Ulcer, with no prior record of previous full-thickness classification information, generally cannot accurately be diagnosed or classified into one of the six stages. In these cases, scar tissue being present likely indicates a full-thickness pressure ulcer, but it is unknown which of the pressure ulcer stages it may have been, so the pressure ulcer should be classified in this case as a Resurfaced Full-thickness Pressure Ulcer.

In various embodiments, this type of pressure ulcer would be considered as unknown or undetermined depth as explained herein and therefore the PUD system 100 would recognize that the medical diagnosis code should be classified as an "Unspecified Stage" to prevent reverse staging (e.g., improperly reducing the severity of the classification of a pressure ulcer). For example, if a closed pressure ulcer was originally classified by a physician as an unstageable pressure ulcer during an office visit with a patient but the wound closed (or healed) and was completely covered with contracted scar tissue by the next physician assessment, then the physician would not be able to diagnose the appropriate classification as the physician was never able to assess/visualize/palpate the wound once slough and eschar were no longer obscuring the wound bed (e.g., such that the wound changed from unstageable to able to be classified) to determine if by the current standards, the appropriate classification. If while that wound was closing/healing, stage 4 characteristics or symptoms were visible, palpable, or true, then, in one embodiment, the wound should be classified as a Stage 4 Pressure Ulcer. Since reverse staging is not appropriate, it generally would be inappropriate to diagnose this pressure ulcer as a Stage 3 Pressure Ulcer, as an Unstageable Pressure Ulcer, as a DTI, as a Stage 2 Pressure Ulcer, as a Stage 1 pressure ulcer, or as no longer a pressure ulcer. Likewise, if while that wound was closing/healing the pressure ulcer presented only with Stage 3 Pressure Ulcer characteristics or symptoms, it would be inappropriate to classify/diagnose the wound as a Stage 4 Pressure Ulcer, Unstageable Pressure Ulcer, DTI, Stage 2 or a Stage 1 Pressure Ulcer.

Table 1 below shows the criteria, characteristics, and symptoms used in conventional methods of diagnosing the six pressure ulcer categories/stages/grades as determined in the 2014 International guideline "Prevention and Treatment of Pressure Ulcers: Clinical Practice Guideline" a collaborative effort among the NPUAP, EPUAP, and the PPPIA. Table 1 also comprises the 2016 NPUAP "Pressure Injury Stages." As will occur to one having ordinary skill in the art, the criteria, characteristics, and symptoms described in Table 1 are for only for exemplary purposes, as the PUD system 100 may be adapted to use whichever criteria, characteristics, and symptoms are appropriate according to the relevant authorities in a particular jurisdiction.

TABLE 1

Conventional Pressure Ulcer Diagnoses Criteria/Characteristics/Symptoms

| | |
|---|---|
| Stage/Category 1: non-blanchable erythema (2014) And Stage 1 Pressure Injury: Non-blanchable erythema of intact skin (2016) | Intact skin with non-blanchable redness of a localized area usually over a bony prominence. Darkly pigmented skin may not have visible blanching; its color may differ from the surrounding area. Further Description: The area may be painful, firm, soft, warmer or cooler as compared to adjacent tissue. Category 1 may be difficult to detect in individuals with dark skin tones. May indicate "at risk" persons (a heralding sign of risk). The latest 2016 definition determined by the NPUAP advises "Intact skin with a localized area of non-blanchable erythema, which may appear differently in darkly pigmented skin. Presence of blanchable erythema or changes in sensation, temperature, or firmness may precede visual changes. Color changes do not comprise purple or maroon discoloration; these may indicate Deep Tissue Pressure Injury." |
| Stage/Category 2: Partial thickness skin loss (2014) And Stage 2 Pressure Injury: Partial-thickness skin with exposed dermis (2016) | Partial thickness loss of dermis presenting as a shallow open ulcer with a red pink wound bed, without slough. May also present as an intact or open/ruptured serum-filled or sero-sanginous filled blister. Further Description: Presents as a shiny or dry shallow ulcer without slough or bruising*. This stage should not be used to describe skin tears, tape burns, incontinence associated dermatitis, maceration or excoriation. *Bruising indicates Deep Tissue Pressure Injury. The latest 2016 definition determined by the NPUAP advises "Partial-thickness loss of skin with |

TABLE 1-continued

Conventional Pressure Ulcer Diagnoses Criteria/Characteristics/Symptoms

| | |
|---|---|
| | exposed dermis. The wound bed is viable, pink or red, moist, and may also present as an intact or ruptured serum-filled blister. Adipose (fat) is not visible and deeper tissues are not visible. Granulation tissue, slough and eschar are not present. These injuries commonly result from adverse microclimate and shear in the skin over the pelvis and shear in the heel. This stage should not be used to describe moisture associated skin damage (MASD) including incontinence associated dermatitis (IAD), intertriginous dermatitis (ITD), medical adhesive related skin ulcer (MARSI), or traumatic wounds (skin tears, burns, abrasions)." |
| *Category/Stage 3: full thickness skin loss* (2014) And *Stage 3 Pressure Injury: Full-thickness skin loss* (2016) | Full thickness tissue loss. Subcutaneous fat may be visible but bone, tendon or muscle are not exposed. Some slough may be present. May comprise undermining and tunneling. The depth of a category/stage 3 pressure ulcer varies by anatomical location. The bridge of the nose, ear, occiput and malleolus do not have (adipose) subcutaneous tissue and category/stage 3 ulcers may be shallow. In contrast, areas of significant adiposity may develop extremely deep category/stage 3 pressure ulcers. Bone/tendon is not visible or directly palpable. The latest 2016 definition determined by the NPUAP advises "Full- thickness loss of skin, in which adipose (fat) is visible in the ulcer and granulation tissue and epibole (rolled wound edges) are often present. Slough and/or eschar may be visible. The depth of tissue damage varies by anatomical location; areas of significant adiposity may develop deep wounds. Undermining and tunneling may occur. Fascia, muscle, tendon, ligament, cartilage and/or bone are not exposed. If slough or eschar obscures the extent of tissue loss this is an Unstageable Pressure Ulcer." |
| *Category/Stage 4: full thickness tissue loss* (2014) And *Stage 4 Pressure Injury: Full-thickness skin and tissue loss* (2016) | Full thickness tissue loss with exposed bone, tendon or muscle. Slough or eschar may be present. Often comprises undermining and tunneling. Further Description: The depth of a category/stage 4 pressure ulcer varies by anatomical location. The bridge of the nose, ear, occiput and malleolus do not have (adipose) subcutaneous tissue and these ulcers may be shallow. Category/stage 4 ulcers may extend into muscle and/or supporting structures (e.g., fascia, tendon or joint capsule) making osteomyelitis or osteitis likely to occur. Exposed bone/muscle is visible or directly palpable. The latest 2016 definition determined by the NPUAP advises, "Full-thickness skin and tissue loss with exposed or directly palpable fascia, muscle, tendon, ligament, cartilage or bone in the ulcer. Slough and/or eschar may be visible. Epibole (rolled edges), undermining and/or tunneling often occur. Depth varies by anatomical location. If slough or eschar obscures the extent of tissue loss this is an Unstageable Pressure Ulcer." |
| *Unstageable/Unclassified: full thickness skin or tissue loss-depth unknown* (2014) And *Unstageable Pressure Injury: Obscured full-thickness skin and tissue loss* (2016) | Full thickness tissue loss in which actual depth of the ulcer is completely obscured by slough (yellow, tan, gray, green or brown) and/or eschar (tan, brown or black) in the wound bed. Further Description: Until enough slough and/or eschar are removed to expose the base of the wound, the true depth cannot be determined; but it will be either a Category/Stage 3 or 4. Stable (dry, adherent, intact without erythema or fluctuance) eschar on the heels serves as "the body's natural (biological) cover" and should not be removed. The latest 2016 definition determined by the NPUAP advises, "Full-thickness skin and tissue loss in which the extent of tissue damage within the ulcer cannot be confirmed because it is obscured by slough or eschar. If slough or eschar is removed, a Stage 3 or Stage 4 pressure injury will be revealed. Stable eschar (e.g., dry, adherent, intact without erythema or fluctuance) on the heel or ischemic limb should not be removed." |
| *Suspected Deep Tissue Injury - depth unknown* (2014) And *Deep Tissue Pressure Injury: Persistent non-blanchable deep red, maroon, or purple discoloration* (2016) | Purple or maroon localized area of discolored intact skin or blood-filled blister due to damage of underlying soft tissue from pressure and/or shear. Further Description: The area may be preceded by tissue that is painful, firm, mushy, boggy, warmer or cooler as compared to adjacent tissue. Deep tissue injury may be difficult to detect in individuals with dark skin tones. Evolution may comprise a thin blister over a dark wound bed. The wound may further evolve and become covered by thin eschar. Evolution may be rapid exposing additional layers of tissue even with treatment. The latest 2016 definition determined by the NPUAP advises, "Intact or non-intact skin with localized area of persistent non- blanchable deep |

TABLE 1-continued

Conventional Pressure Ulcer Diagnoses Criteria/Characteristics/Symptoms red, maroon, purple discoloration or epidermal separation revealing a dark wound bed or blood filled blister. Pain and temperature change often precede skin color changes. Discoloration may appear differently in darkly pigmented skin. This injury results from intense and/or prolonged pressure and shear forces at the bone-muscle interface. The wound may evolve rapidly to reveal the actual extent of tissue injury, or may resolve without tissue loss. If necrotic tissue, subcutaneous tissue, granulation tissue, fascia, muscle or other underlying structures are visible, this indicates a full thickness pressure ulcer (Unstageable, Stage 3, or Stage 4). Do not use DTPI to describe vascular, traumatic, neuropathic, or dermatologic conditions."

The authentication module 120 of the PUD tool 112, in various embodiments, is used to manage the authentication process of the user 105 of the PUD system 100. For example, when the user 105 signs into the PUD tool 112, a standard authentication process is performed that allows the user 105 to access the PUD tool 112. User-sign in may occur a number of ways. In one example, the user 105 may use a web browser to access the PUD GUI 118 of the PUD tool 112 and enter credentials (e.g., username and password). In another example, the PUD GUI 118 of the PUD tool 112 is a mobile app that the user 105 uses to enter his/her credentials. In yet another example, the user sign-in process may occur automatically when the user 105 starts the mobile app. In still yet another example, a user may sign in when they sign into their electronic medical record (EMR), for example when PUD tool 112 system and method are integrated and/or build directly into an EMR. In another example, a user may sign in via a scan method such as scanning a barcode, fingerprint, or retina, to identify the user.

The security module 122 of the PUD tool 112, in various embodiments, is used to perform any system security functions with respect to keeping the contents of the data store 114 secure, for example, to ensure compliance with patient health data privacy laws, such as the Health Insurance Portability and Accountability Act, commonly known as HIPPA and the Health Information Technology for Economic and Clinical Health Act, commonly known as the HITECH Act. The security module 122 may use security techniques, such as encryption, secure hashtags (or hash tags), and the like.

In various embodiments, the data store 114 may be any computing device (e.g., desktop computer, laptop, servers, tablets, etc.), combination of computing devices, software, hardware, combination of software and hardware, database (e.g., stored in the cloud or on premise, structured as relational, etc.), or combination of databases that is capable of performing the functionality disclosed herein; for example, the data store 114 may be data repositories (like databases) and/or flat files that may store data, such as application data 130, user data 132, patient data 134, and/or image data 136. Further, the PUD system 100 is not limited to only one data store 114; the PUD system 100 may comprise multiple data stores 114.

The application data 130 may comprise any information about pressure ulcer diagnostics that may be useful to the PUD tool 112. For example, the application data 130 may comprise information supplied by the NPUAP, the EPUAP, MDS, CMS, and/or the PPPIA, WHO, which may be used, for example, to inform the diagnosis module 116.

As users 105 are authorized to access PUD system 100, user information is generally stored in the user data 132 in the data store 114. In PUD system 100, the users 105 may be created, for example, by their organization who may assign a system administrator(s). For each user 105, information in user data 132 may comprise, for example, account information, organization, user name, job title, group name, user/group credentials, email address, employee identification number, and the user's or organization's preferred classification standards/verbiage (e.g., stage, grade, category, Unstageable or Unclassified, MDS, etc.), the user's or organization's preferred treatment recommendations, and the like.

Figure 7:
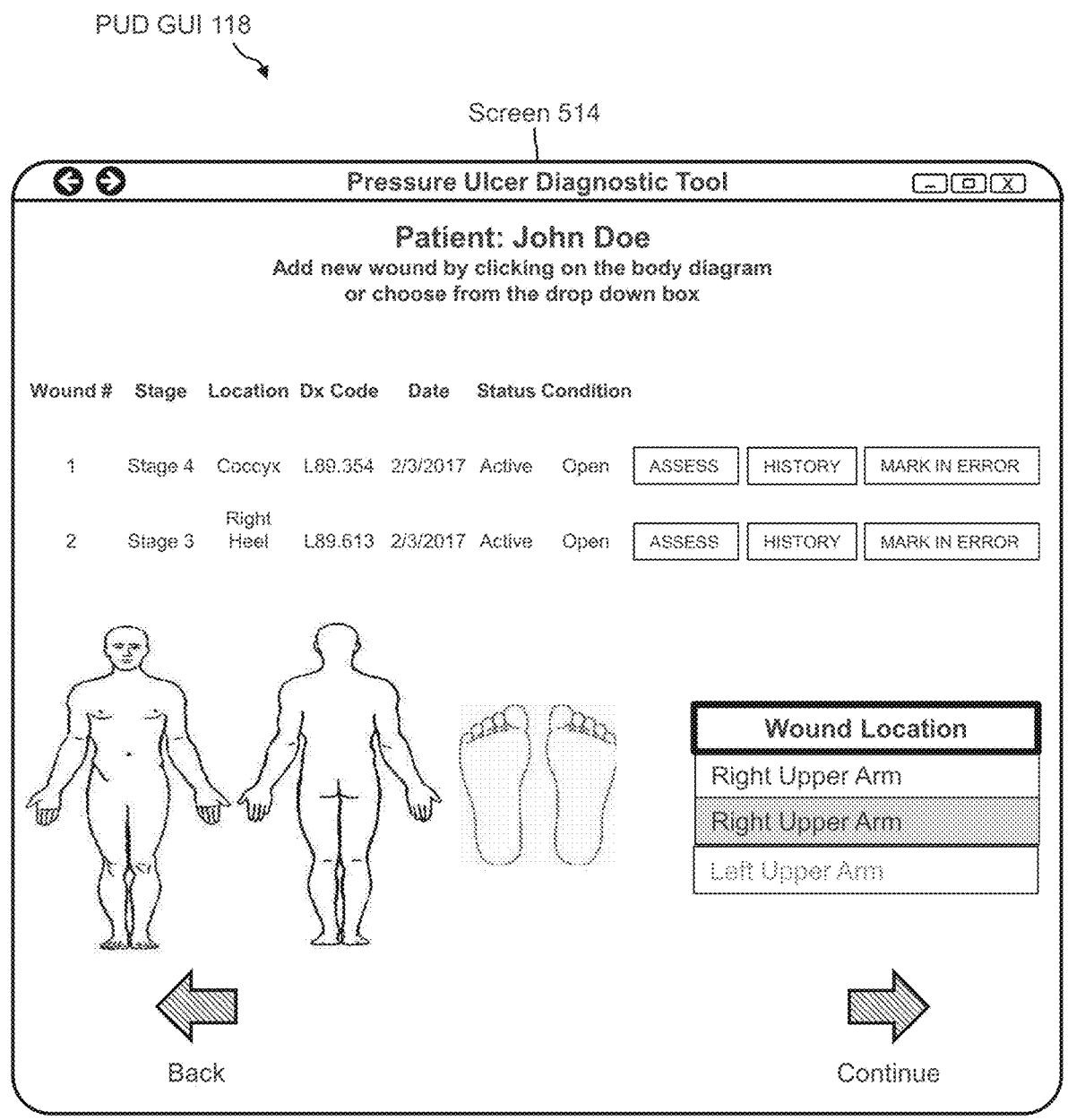
FIG. 7 is a screenshot of an exemplary patient history screen of a PUD system, according to one embodiment of the present disclosure.

The patient data 134, in various embodiments, comprises information about patients that are the subject of the pressure ulcer diagnostic. The patient data 134 may contain, for example, patient names/addresses/insurance/contact information, patient credentials, patient medical record/identification numbers, patient history information (e.g., patient electronic medical record), and the like. Further, an "history" button may be used to display to the user all of the past diagnoses—for example, past diagnoses ordered by date with the option to select certain date ranges and the option to organize from most recent to oldest diagnoses and vice-versa. FIG. 7, 8A, and FIG. 8B, which are examples of information about past diagnoses that may be displayed by selecting the "history" button.

The image data 136 may comprise, for example, digital images or files depicting the different categories/stages of pressure ulcers that may be referenced by the user 105 while using the PUD tool 112, as well as any digital images captured using the image capture device 126. For example, using the image capture device 126, the user 105 may take digital images of a patient's wound bed to assist with pressure ulcer diagnostics. Commercially available software is available that enables a user to take a picture of a wound and upload it to the software and then assign the colors to the tissue shown in the picture of the wound. Then, based on the practitioner's assignment of colors, the software indicates the percentages of different tissue types, and measures the length, width and surface area of the wound, but not depth. However, depth may be input by the practitioner. One example of this software is the PictZar® Digital Planimetry Software, such as PictZar® CDM and PictZar® Pro, which are planimetry software programs that are used to make measurements on digital photographs as well as help determine the different tissue types present and the percentage of improvement or decline in the wound. PictZar® may be used to measure wounds and other lesions that may present on the surface of a patient's skin.

The communications interface 124 may be any wired and/or wireless communication interface for connecting to a network (not shown) and by which information may be exchanged with other devices connected to the network. Examples of wired communication interfaces may comprise, but are not limited to, USB ports, RS232 connectors, RJ45 connectors, Ethernet, and any combinations thereof. Examples of wireless communication interfaces may comprise, but are not limited to, an Intranet connection, Internet, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (e.g., IPv6 over Low Power Wireless Area Network (6LoWPAN)), ANT or ANT+(Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols.

Figure 2:
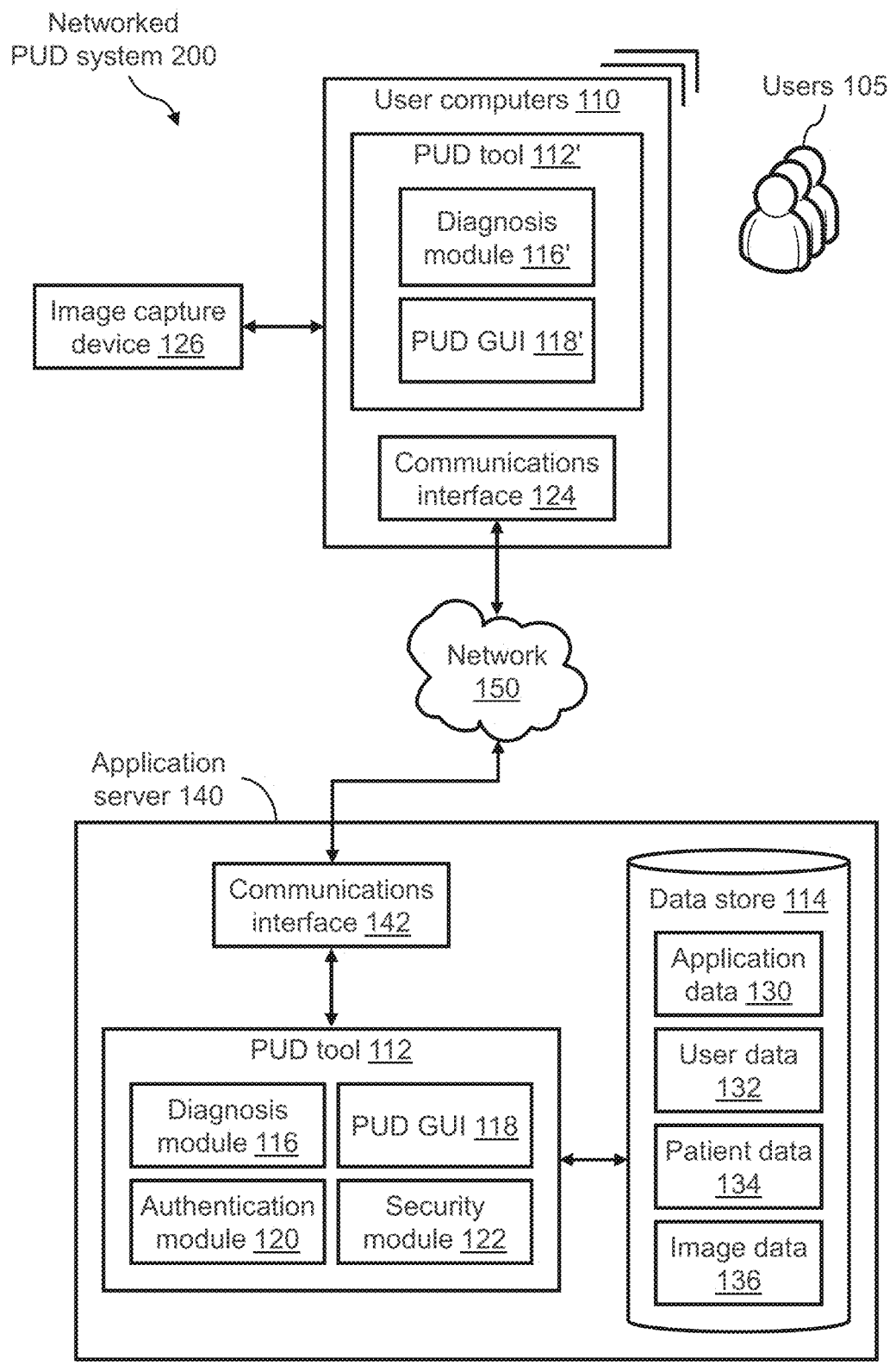
FIG. 2 illustrates architecture details of an exemplary networked PUD system, according to one embodiment of the present disclosure.

Referring now to FIG. 2, architecture details of an exemplary networked PUD system 200 are shown according to one embodiment of the present disclosure. Generally, the exemplary networked PUD system 200 comprises a networked configuration with the PUD tool 112 running on an application server 140 that further comprises the data store 114. In various embodiments, a plurality of users 105 may access the application server 140 via their respective user computers 110, which are connected to application server 140 via a network 150. The user computers 110 generally may be any computer devices, such as, but not limited to, desktop computers, laptop computers, handheld computing devices, mobile phones (or smart phones), and tablet devices. The networked PUD system 200, in one embodiment, may operate in a client/server computing architecture. Namely, in one embodiment, the PUD tool 112 at the application server 140 is the server component of the networked PUD system 200, whereas the PUD tool 112' at each of the user computers 110 is the client component of the networked PUD system 200. In other words, in one embodiment, the PUD tool 112' at each of the user computers 110 is the counterpart to the PUD tool 112 at the application server 140. The PUD tool 112 is generally a software application by which pressure ulcers may be accurately classified over a network. In a particular embodiment, the diagnosis module 116 manages the overall operations of the PUD tool 112 at the application server 140.

At each of the user computers 110, in various embodiments, the PUD tool 112' comprises the diagnosis module 116' and the PUD GUI 118'. The users 105 generally may use the PUD GUI 118' to interact with the PUD tool 112'. In various embodiments, the PUD tool 112' may be implemented as a web application and run in a web browser, such as Internet Explorer, Safari, Chrome, Firefox, and the like. However, in various embodiments, the PUD tool 112' may be implemented by other means, such as a .NET application, a desktop application, a mobile app, an API, and the like. When configured as a mobile app, in various embodiments, the PUD tool 112' may be designed to operate on any device platform, including for example, Windows®, Android®, Apple®, and the like. The application server 140 may generally be any networked computing configuration as long as it is accessible via network 150 by the user computers 110 of the users 105. For example, the networked PUD system 200, and more particularly the PUD tool 112 on the application server 140, may support a cloud computing environment. In a cloud computing environment, in one embodiment, the application server 140 is the cloud server. Further, the PUD tool 112 is generally not limited to running on one application server 140 only. The networked PUD system 200, in various embodiments, may comprise multiple application servers 140 (or cloud servers) to ensure high-availability of computing resources. Network 150 may be, for example, a local area network (LAN) and/or a wide area network (WAN) for connecting to the Internet or to an Intranet. The application server 140 and the user computers 110 generally may connect to network 150 by any wired and/or wireless means. The application server 140 comprises, for example, a communications interface 142, which is substantially the same as the communications interface 124 of user computer 110 described with reference to FIG. 1.

Figure 3:
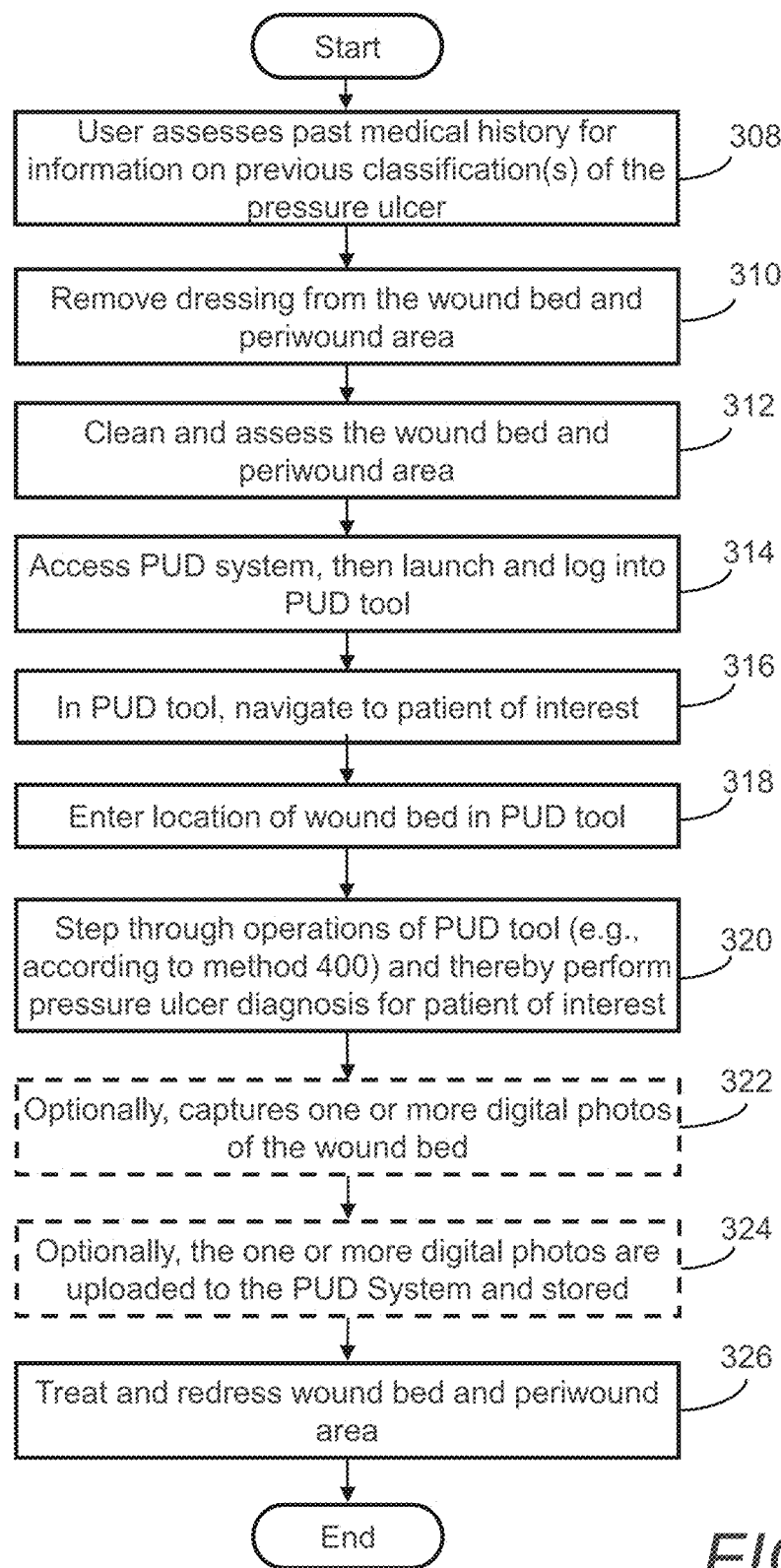
FIG. 3 is a flowchart summary of an exemplary pressure ulcer classification and treatment method, according to one embodiment of the present disclosure.

Now referring to FIG. 3, a flowchart summary of an exemplary pressure ulcer classification and treatment method 300 is shown according to one embodiment of the present disclosure. Generally, the method 300 is the process by which a user 105 accurately classifies and treats pressure ulcers using the presently disclosed PUD system 100 of FIG. 1 (and networked PUD system 200 of FIG. 2). As will be understood by one having ordinary skill in the art, the steps and processes shown in FIG. 3 (and those of all other flowcharts and sequence diagrams shown and described herein) may operate concurrently and continuously, are generally asynchronous and independent, and are not necessarily performed in the order shown.

In various embodiments, the method 300 begins at step 308, wherein the user 105 assesses past medical history of a particular patient for information on previous classifications of the particular pressure ulcer. In various embodiments, that past medical history may be physical file, data stored in a third-party electronic medical records system (to which the PUD system 100 or the networked PUD system 200 may or may not be connected), or data stored in the data store 114. Generally, the review at step 308 permits the user 105 to determine what are the appropriate actions to take with respect to a particular pressure ulcer (e.g., classification, treatment, etc.).

In one embodiment, at step 310, the user 105 removes the dressing from the ulcer wound bed and periwound area. At step 312, in various embodiments, the user 105 cleans the wound bed and periwound area. For example, a cleaning solution is administered to the wound bed and periwound area. Exemplary cleaning solutions comprise, without limitation, normal saline, sterile water, wound cleanser, hydrogen peroxide, chlorhexidine, sodium hypochlorite, and the like.

At step 314, in various embodiments, the user 105 or users 105 access the PUD system 100 (or the networked PUD system 200), then launches and logs into the PUD tool 112. For example, the user 105 uses the PUD GUI 118 to log into and interact with the PUD tool 112. At step 316, in the PUD tool 112, the user 105 generally navigates to the patient of interest. In one example, the patient of interest is an existing patient that may be located by entering, for example, a medical record number or the patient's first and last name. In another example, the patient of interest is a new patient that may be added in the PUD tool 112 by entering, for example, the patients' first and last name, birthdate, and medical record number. In some embodiments, a device may allow for the patients' armband, sticker, or information embedded into a barcode to access the appropriate patient. For example, when the system, method and tool disclosed herein are linked/integrated into an EMR, certain facilities have scan guns that scan a patient's armband or label prior to administering treatments or medications. Accordingly, in some embodiments, the PUD tool 112 may navigate to a patient of interest in this manner.

At step 318, the location (e.g., elbow, ankle, back, buttock, etc.) of the patient's wound bed is entered into the PUD tool 112. At step 320, the user 105 or users 105 steps through the operations of the PUD tool 112 and thereby performs the pressure ulcer diagnostic for the patient of interest. Namely, the user uses the PUD tool 112 to perform the pressure ulcer diagnostic according to, for example, a method 400 shown in FIG. 4. In certain steps of the diagnostic process, the wound bed (and the periwound area) are physically palpated by the user or a healthcare provider.

At step 322, the user optionally captures one or more digital photos or files of the wound bed or the patient. For example, using the image capture device 126 connected to the user computer 110, the user captures one or more digital photos of the wound bed. At step 324, the user optionally uploads the one or more digital photos of the wound bed to the PUD system 100 for storage in the image data 136 of the data store 114.

Those skilled in the art will appreciate that optional steps 322 and/or 324 may be performed at any time in method 300 after the dressing is removed from the wound bed and periwound area at step 310, preferably after the wound bed and periwound area are cleaned in step 312 and before the wound bed and periwound area are treated and redressed in step 326. In some embodiments, for example, one or more digital images/file of the wound bed are captured using image capture device 126 when the location of the wound bed is entered in the PUD tool 112. For example, in one embodiment, the location of the wound bed is entered in the PUD tool 112 and the user uploads one or more digital photos of the wound bed and periwound area showing the location of the wound into the PUD tool 112. It should be appreciated that one or more digital photos may be uploaded before or after the location of the wound bed is entered in the PUD tool 112, as the accuracy of the pressure ulcer diagnosis is not dependent on the timing of when one or more digital photos are uploaded. In another embodiment, when prompted by the PUD tool 112 to enter the location of the wound bed in step 318, the user of the PUD tool 112 may take one or more digital photos using image capture device 126 and upload the one or more digital photos of the wound bed into the PUD tool 112 wherein, once uploaded, the PUD tool 112 using a data/imaging analysis module (not shown) automatically enters the location of the wound bed in the PUD tool 112 of the data contained in the images shown in one or more digital photos of the wound bed uploaded. Alternatively, when prompted by the PUD tool 112 to enter the location of the wound bed in step 318, the user of the PUD tool 112 may select one or more digital photos stored in image data 136 of data store 114 for analysis by the data/imaging analysis module, which automatically enters the location of the wound bed in the PUD tool 112 based on the analysis of the data contained in the images shown in the one or more digital photos of the wound bed stored in image data 136 of data store 114. Similarly, in one embodiment, the user may take and upload or select one or more photos of the wound bed for analysis by the data/imaging analysis module to perform the steps of method 400.

At step 326, in one embodiment, the wound bed and the periwound (partially or in whole) is treated and redressed. It should be appreciated that the particular treatment applied to the wound may vary depending, for example, on the stage of the pressure ulcer diagnosed, the treatment guidelines followed by the particular health care facility in which the patient's pressure ulcer is being diagnosed, and the like. Exemplary treatments of pressure ulcers comprise, without limitation, debridement (including but not limited to enzymatic, chemical, biologic, sharp, and/or autolytic), hydrofibers, gelling fiber dressings, collagen based dressings, transparent film, hydrocolloids, hydrogel, foam, polymeric membrane dressings, cadexomer iodine dressings, silver impregnated dressings, antimicrobial dressings, calcium alginate dressings, honey containing dressings, glycerin dressings, grafts, surgery, antimicrobial creams/lotions, antifungal creams/lotions, antibiotics, gauze based dressings, grafts, Negative Pressure Wound Therapy, and/or the like.

Figure 4A:
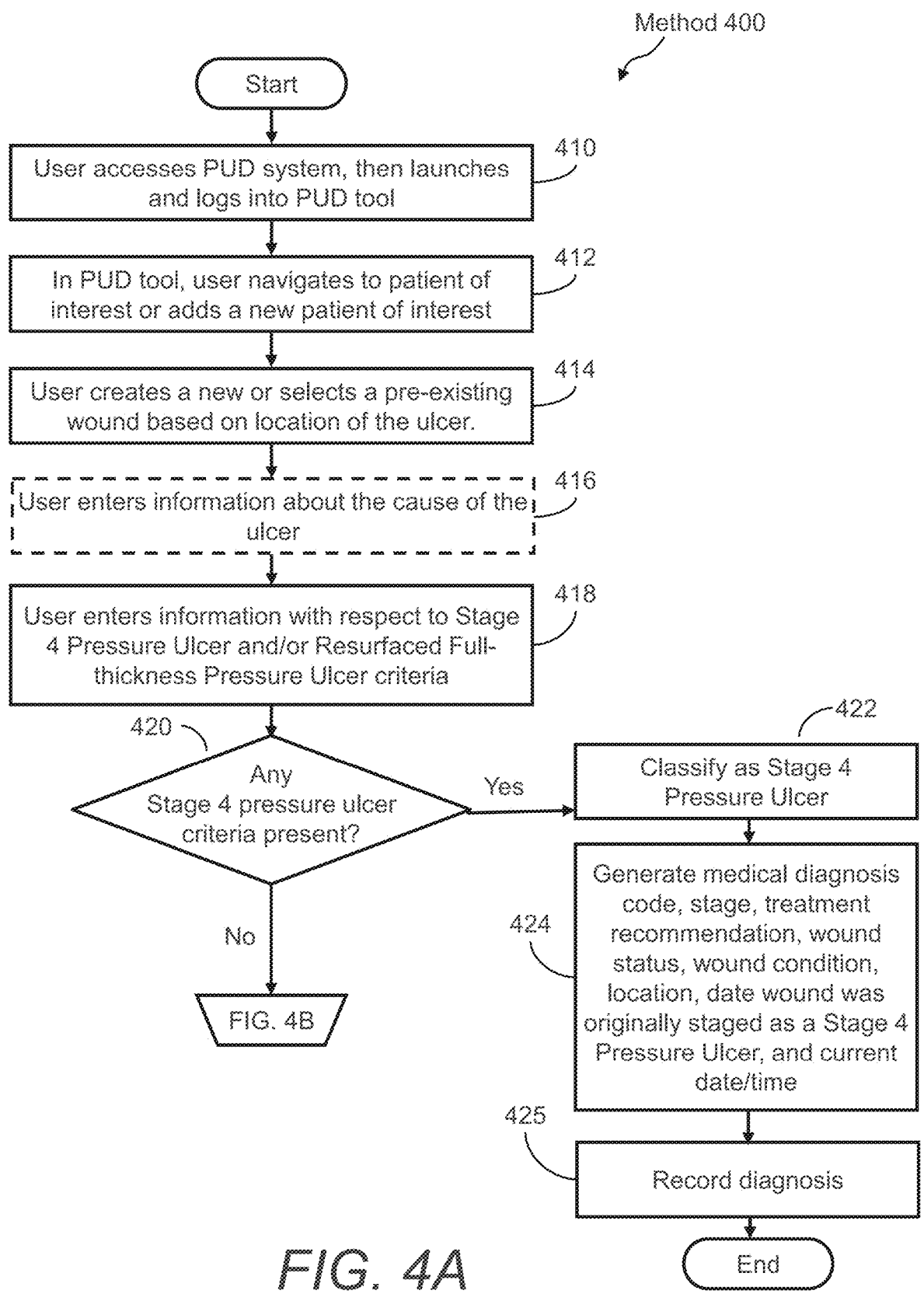
FIG. 4 (consisting of FIGS. 4A, 4B, 4C, and 4D) is a flowchart of an exemplary pressure ulcer classification method, according to one embodiment of the present disclosure.
Figure 4B:
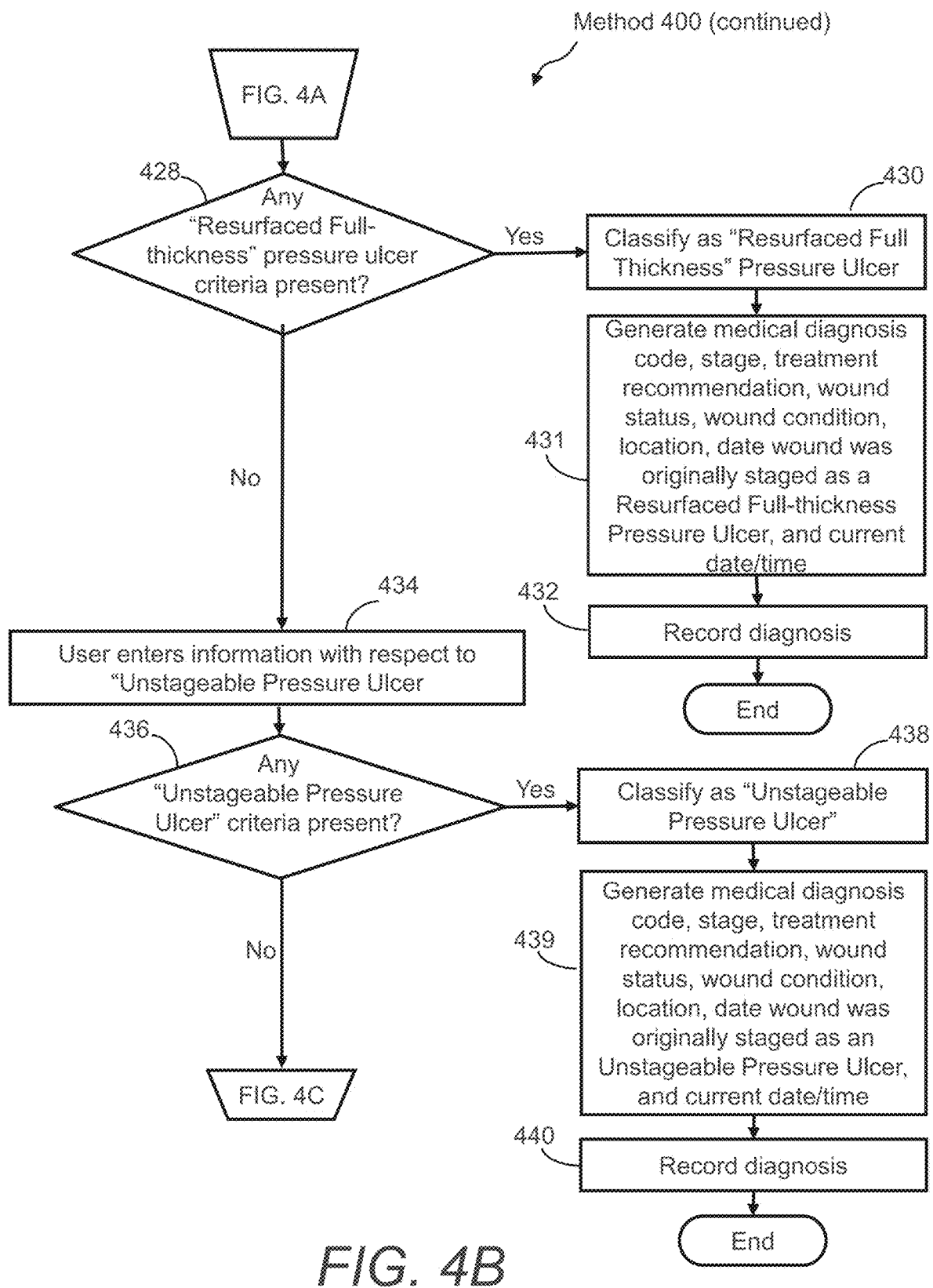
Figure 4C:
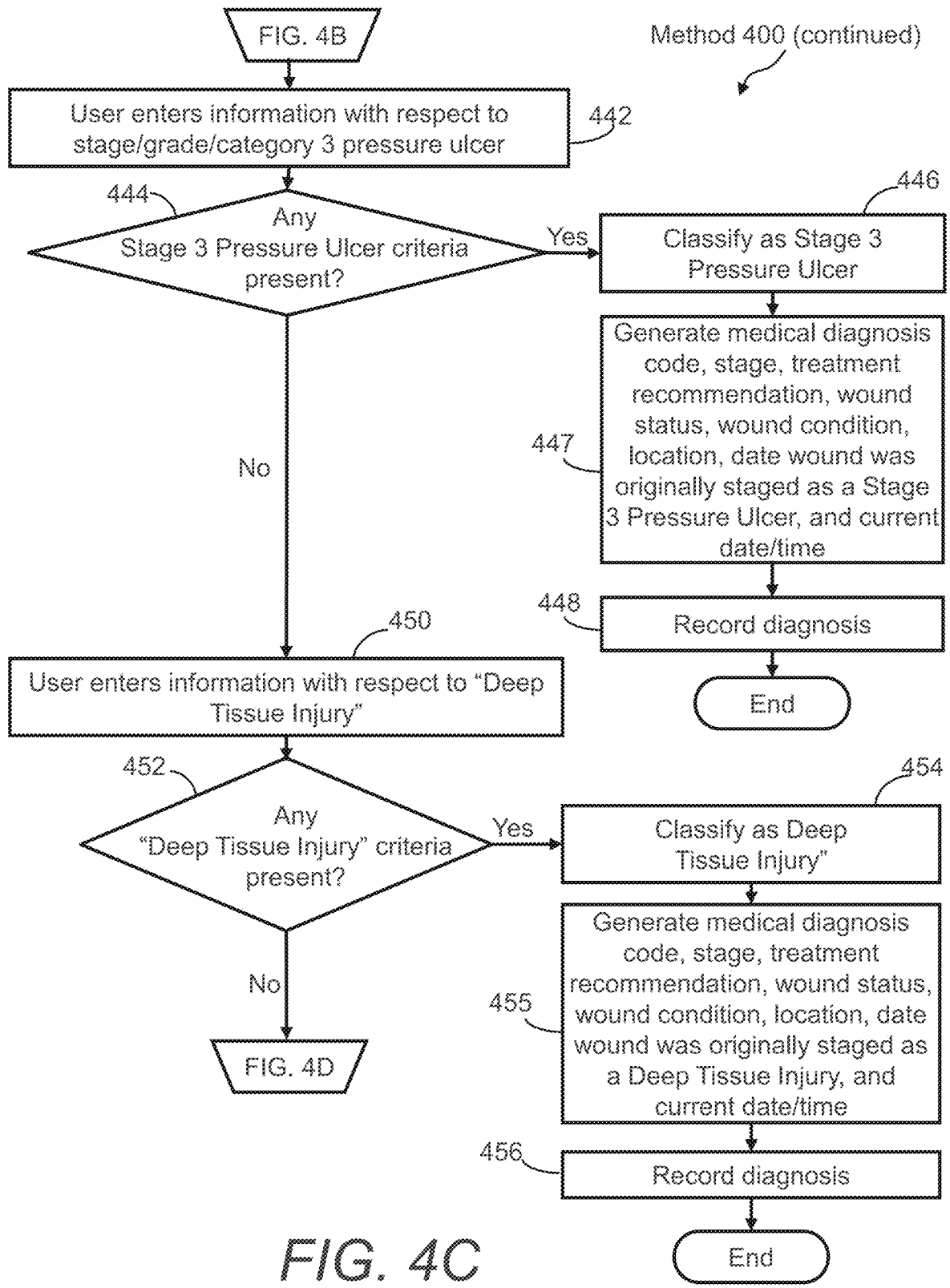

Referring now to FIG. 4 (consisting of FIGS. 4A, 4B, 4C, and 4D), a flowchart of an exemplary pressure ulcer classification method 400 is shown according to one embodiment of the present disclosure. Generally, the method 400 is the process by which the PUD tool 112 accurately diagnoses pressure ulcers. Throughout the steps of the method 400, FIG. 5 through FIG. 23 will be referenced, wherein FIG. 5 through FIG. 23 show examples of screens of the PUD GUI 118 of the PUD tool 112. Further, in addition to depicting the process steps of accurately diagnosing pressure ulcers using the PUD tool 112, certain process steps will indicate certain beneficial features that are built into the PUD tool 112. For example, in various embodiments, the diagnosis module 116 of the PUD tool 112:

(1) ensures accurate diagnosis of Stage 4 Pressure Ulcers and prevents reverse staging of Stage 4 Pressure Ulcers to a Resurfaced full-thickness Pressure Ulcer, Unstageable Pressure Ulcer, Stage 3 Pressure Ulcer, Deep Tissue Injury, Stage 2 Pressure Ulcer, Stage 1 Pressure Ulcer, as not a pressure ulcer at all, or as a Healed pressure ulcer, once a pressure ulcer has been determined at any time to Be classified as a Stage 4 Pressure Ulcer;

(2) ensures accurate diagnosis of Resurfaced Full-thickness Pressure Ulcers and prevents reverse staging of Resurfaced Full-thickness Pressure Ulcers to an Unstageable Pressure Ulcer, a Stage 3 Pressure Ulcer, Stage 2 Pressure Ulcer, Stage 1 Pressure Ulcer, as not a pressure ulcer, or as a healed pressure ulcer, while still allowing the ability for the Resurfaced Full-thickness Pressure Ulcer to become a Stage 4 Pressure Ulcer if the pressure ulcer is determined as such at any subsequent giventime.

(3) ensures accurate diagnosis of Unstageable Pressure Ulcers and prevents reverse staging of Unstageable Pressure Ulcers to a Deep Tissue Injury, a Stage 3 Pressure Ulcer while Unstageable Pressure Ulcer characteristics or symptoms listed in e) iii) are still visible, palpable, and/or true, Stage 2 Pressure Ulcer, Stage 1 Pressure Ulcer, as not a pressure ulcer at all, as a healed pressure ulcer, while still allowing the Unstageable Pressure Ulcer to become a Stage 3 Pressure Ulcer, a Resurfaced Full-thickness Pressure Ulcer, or a Stage 4 Pressure Ulcer, if the pressure ulcer is determined as such at any subsequent given time;

(4) ensures accurate diagnosis of Stage 3 Pressure Ulcers and prevents reverse staging of Stage 3 Pressure Ulcers to a DTI, Stage 2 Pressure Ulcer, Stage 1 Pressure Ulcer, as not a pressure ulcer, or as a healed pressure ulcer that is no longer present, while still allowing the Stage 3 Pressure Ulcer to become a Resurfaced Full-thickness Pressure Ulcer, Unstageable Pressure Ulcer, or a Stage 4 Pressure Ulcer if the pressure ulcer is determined as such at any subsequent time;

(5) ensures accurate diagnosis of Deep Tissue Injuries;

(6) ensures accurate diagnosis of Stage 2 Pressure Ulcers;

(7) ensures accurate diagnosis of Stage 1 Pressure Ulcers;

(8) ensures accurate diagnosis of a healed pressure ulcer;

(9) ensures that a wound that does not have the characteristics or symptoms of one of the seven pressure ulcer classifications is not diagnosed as a pressure ulcer;

(10) ensures mucous membrane pressure ulcers are not classified using the NPUAP, EPUAP, and the PPPIA standards, if this option of standards is selected;

(11) ensures appropriate, accurate, and necessary documentation is available to justify the classification and diagnosis of the pressure ulcer;

(12) ensures the appropriate medical diagnosis code is assigned to a pressure ulcer;

The method 400 generally begins at step 410, wherein a user 105, in one embodiment, accesses the PUD system 100 and launches and logs into the PUD tool 112. In one example, and referring now to a screen 510 shown in FIG. 5, using the PUD GUI 118, the user enters their username and password. In one embodiment, steps 410, 412, and 414, may replace steps 314, 316, and 318 from the method 300.

At step 412, in the PUD tool 112, the user, in one embodiment, navigates to a patient of interest or adds a new patient into the system. In one example, and referring now to a screen 512 shown in FIG. 6, the patient of interest is an existing patient that may be selected by entering the patient's medical record number or the patient's first and last name or scanning the patients' information (e.g., via a scanning device to a barcode like on a patient hospital wristband). If the user enters a patient's first and/or last names, all patients with the same name may be displayed (e.g., displayed in a popup window not shown). The user could then verify that the patient's medical record number and the name of the patient match to select a particular patient.

Figure 6:
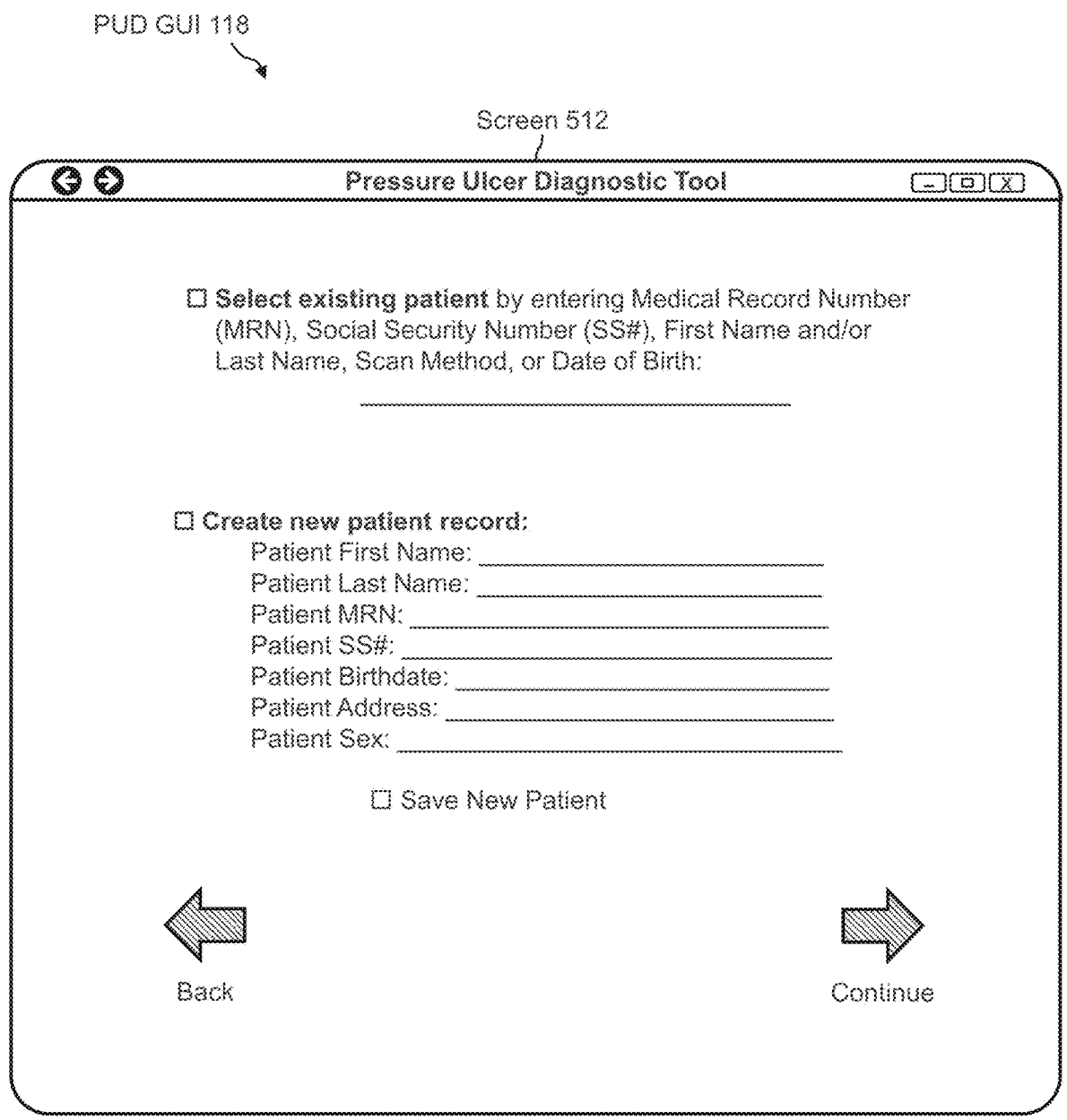
FIG. 6 is a screenshot of an exemplary patient selection screen of a PUD system, according to one embodiment of the present disclosure.

In another example, and referring to again to the screen 512 shown in FIG. 6, the patient of interest is a new patient that may be added into the PUD tool 112 by entering the information regarding the patient such as the patients' first and last name, medical record number, and their gender. The user may then click the "Save new patient" checkbox and select the "Continue" button. Accordingly, the PUD system 100 proceeds forward with classification of pressure ulcers for that selected patient.

At step 414, in one embodiment, the user creates a new or selects a pre-existing ulcer based on the location of the wound to be diagnosed. Here, the word "new" would generally not be indicative of the age of the ulcer but rather a new ulcer in this case would be defined as an ulcer that has not been previously diagnosed by the disclosed system, whereas a pre-existing ulcer would be considered one that has been previously diagnosed by the disclosed system.

If creating a new ulcer classification, at step 414, the user generally may enter the location of the wound bed. In one example, and referring now to a screen 514 shown in FIG. 7, the user selects from a dropdown menu of ulcer locations, based on the location of the patient's ulcer. Table 2 below shows a non-exhaustive list of exemplary pressure ulcer locations. Depending on the jurisdiction where the disclosed system is deployed, these locations may be revised to reflect the appropriate organizational preferences but, in Table 2, are currently shown as following the ICD-10 coding system. Additionally, in one embodiment, if the user selects a wound location that is located on a mucous membrane of the body, such as the vaginal canal, urinary tract, tongue, nasal passage, eyelid, or gastrointestinal tract, etc., an optional feature of the PUD tool may be activated that will display a message (e.g., in a popup-window not shown) stating, for example, "Mucosal Pressure Ulcers are not classified by the NPUAP Pressure Ulcer definitions." This message is an optional feature that may be made active in the PUD tool 112 by the system administrator. If a wound location that is a mucous membrane is selected, then, in various embodiments, the user may either select "Continue" to end the diagnosis or select "Cancel" to enter a different location. If any other non-mucous membrane body location is selected, then, in one embodiment, the method 400 proceeds to step 416. That is, in one embodiment if the mucous membrane optional feature is activated by the administrator, only if the user selects a location other than the vaginal canal, urinary tract, tongue, nasal passage, eyelid, or gastrointestinal tract, etc., will the diagnosis module 116 of the PUD tool 112 proceed to the next step 416, whereas choosing a mucous membrane location ends the classification/diagnosis.

TABLE 2

| Pressure Ulcer Location |
| --- |
| Ankle (Right) |
| Ankle (Left) |
| Ankle (Unspecified) |
| Back (Right, Upper) |
| Back (Right, Lower) |
| Back (Left, Upper) |
| Back (Left, Lower) |
| Back (Unspecified Region) |
| Buttock (Right) |
| Buttock (Left) |
| Buttock (Unspecified) |
| Contiguous site of back, hip, and buttock |
| Elbow (Right) |
| Elbow (Left) |
| Elbow (Unspecified) |
| Head |
| Heel (Right) |
| Heel (Left) |
| Heel (Unspecified) |
| Hip (Right) |
| Hip (Left) |
| Hip (Unspecified) |
| Sacral Region |
| Other Site |
| Unspecified Site |

In one embodiment, and referring now to a screen 514 shown in FIG. 7, the user may select a previously diagnosed/classified ulcer for the particular patient. In one example, a previously diagnosed ulcer may be selected via a dropdown menu list of ulcers previously entered into the system 100 or 200 (e.g., via a popup window—not shown) or by selecting the location of the wound on a body image(s), as shown on screen 514 in FIG. 7. Namely, if the patient has previously diagnosed ulcers, the diagnosis module 116 of the PUD tool 112, in various embodiments, automatically populates the list menu and the visual body image with this information. Further, if a previously diagnosed ulcer is selected, in one embodiment, a "history" button may be used to launch, for example, via a popup window (not shown) or a new screen, as seen in screen 515 in FIG. 8A, that displays information about the selected ulcer (e.g., ulcer history information stored in patient data 134 and any image of the wound would be stored in the image data 136).

At step 416, in one embodiment, when a new pressure ulcer is created at step 414, the user enters information about the cause of the ulcer. The PUD tool asks "Is this ulcer caused by pressure and/or pressure in conjunction with shear," as shown in screen 517 in FIG. 9. The user generally selects "Yes" or "No" to answer the question. For a pre-existing ulcer in the system 100 or 200, however, step 416 will be skipped automatically if the user previously answered "Yes." For a new pressure ulcer that has not been saved into the application, in one embodiment, if "No" is selected, then a message will be displayed (e.g., in a popup window—not shown) that states "This is not a pressure ulcer." In this embodiment, the user must then select "Continue" to proceed with the PUD tool 112. If "Yes" is selected, then, in one embodiment, the PUD tool 112 proceeds to step 418 upon clicking "Continue." That is, in one embodiment, only if "Yes" is selected will the diagnosis module 116 of the PUD tool 112 proceeds to the next step 418, whereas choosing "No" ends the diagnosis/classification.

At step 418, in one embodiment, the PUD tool 112 receives information with respect to classification of a Stage 4 Pressure Ulcer and a Resurfaced Full-thickness Pressure Ulcer (e.g., through user entry, image analysis of a photo of the pressure ulcer, etc.). In one example, and referring now to a screen 518 shown in FIG. 10A, a prompt appears on the display with the question, "Is or was any of the following visible, palpable, and/or true (select all that apply)?" To answer the question, in one embodiment, the user 105 first physically palpates the wound bed (and periwound area) or, if the user is not the entity assessing the patient, the user could locate the answers to the questions in the patient's medical record. Generally, the PUD tool 112 may provide the user 105 with instructions on where and how to physically palpate the wound bed (e.g., written instructions, videos, etc.). After palpating the wound bed (and periwound area) or locating this information in the patient's medical record, the user, in one embodiment, selects all of the symptoms/characteristics that apply from a list of conditions (e.g., whether "Bone", "Muscle", "Tendon", "Ligament", "Cartilage", "Fascia", "Joint Capsule", or "Other supporting structures" were visible and/or palpable; "This was previously classified as a Stage 4 Pressure Ulcer"; and/or "This pressure ulcer is or was closed, is or was 100% scar tissue. AND the previous stage was an Unstageable Pressure Ulcer or is Unknown."). In the example shown in FIG. 10A, check boxes are provided to enable the user 105 to select the applicable characteristics/symptoms from the list. Those skilled in the art will appreciate, however, that other means may be provided to enable a user to select the appropriate Stage 4 Pressure Ulcer or Resurfaced Full-thickness Pressure Ulcer characteristics or symptoms, for example, using a drop-down menu, or the like. The user 105 may, in one embodiment, also indicate whether the characteristics or symptoms selected were visible and/or palpable, for example, by selecting the appropriate check boxes. Alternatively, or additionally, the user may select "This wound was previously classified as a Stage 4 Pressure Ulcer," which is a Stage 4 Pressure Ulcer characteristic, or "This pressure ulcer is or was closed, is or was resurfaced with 100% scar tissue and/or epithelium, AND the last known stage was Unstageable or Unknown," which is a Resurfaced Full-thickness Pressure Ulcer characteristic. In various embodiments, the user may select the "Back" button to review the previous screen (e.g., screen 517), the "Continue" button to proceed to step 420, or the "cancel" button to cancel the classification.

At step 420, based on the information provided at step 418, the diagnosis module 116 of the PUD tool 112 determines whether any one or more Stage 4 Pressure Ulcer characteristics or symptoms are present (e.g., whether "Bone", "Muscle", "Tendon", "Ligament", "Cartilage", "Fascia", "Joint Capsule", or "Other supporting structures" were visible and/or palpable; and/or "This was previously classified as a Stage 4 Pressure Ulcer"). Namely, in one embodiment, if in step 418 any one or more conditions on screen 518 shown in FIG. 10A are selected, then the particular pressure ulcer being classified is a Stage 4 Pressure Ulcer (e.g., the pressure ulcer is stage/grade/category 4), and the PUD tool 112 proceeds to step 422.

Further, and referring now to FIG. 10B, in one embodiment, for all future diagnoses of this particular pressure ulcer for this patient, if in step 418 any one or more of the Stage 4 Pressure Ulcer characteristics or symptoms on screen 518 is selected, then the PUD tool 112 will automatically classify the particular pressure ulcer as previously classified as a Stage 4 Pressure Ulcer (e.g., the checkbox stating, "This wound was previously classified as a Stage 4 Pressure Ulcer," will be automatically selected and the date this ulcer was initially classified as a Stage 4 Pressure Ulcer may be optionally displayed beside that statement) and prevent the pressure ulcer from ever being reverse staged to a less-severe classification of pressure ulcer. In various embodiments, this feature of the diagnosis module 116 of the PUD tool 112 prevents reverse staging and allows the user 105 to easily track stage changes on a pressure ulcer in the medical record. Once "This wound was previously classified as a Stage 4 Pressure Ulcer" is selected, in one embodiment, the user 105 cannot deselect this option on any future assessment without an override. For example, using an "Override" button, the user may select that this option was: (1) previously chosen in error; (2) new staging information has become available that verified this ulcer was never a Stage 4 Pressure Ulcer, which will allow the user to then proceed to step 428; or (3) the optional date showing the date this ulcer was initially classified as that Stage 4 Pressure Ulcer may also be edited to reflect the information available in the patients' medical record prior to the date in the PUD system 100 or the networked PUD system 200 was used if such a date is known (for example, if the ulcerwas known to be a Stage 4 Pressure Ulcer on Jan. 1, 2016, but the PUD tool 112 is not used for the first time until Mar. 1, 2016, the override option would allow the Mar. 1, 2016, date to be changed to the date the ulcer was initially classified as a Stage 4 Pressure Ulcer, which in this example would be on Jan. 1, 2016). In one embodiment, in this step as well as in any subsequent steps, if the "override" function has been invoked, then the "Override" button changes color, for example, from green to red, and this will also be reflected on the history reports. At step 422, the diagnosis module 116 of the PUD tool 112 classifies the patient's ulcer as a Stage 4 Pressure Ulcer.

At step 424, the diagnosis module 116 of the PUD tool 112 generates, based on the information received at step 418, a medical diagnosis code that correlates to the diagnosis/classification results, the stage of the pressure ulcer, the wound location, the wound status (e.g., active, inactive, marked in error), the wound condition (e.g., open, closed, healed, marked in error, not applicable), the date and time of the current assessment, the date and time of a previous assessment when this pressure ulcer first became this stage (if applicable), and a treatment recommendation.

At step 425, in various embodiments, the diagnosis/classification of the ulcer as a Stage 4 Pressure Ulcer is recorded in the patient data 134 in the data store 114 and the patient's chart is closed. In one embodiment, and referring now to a screen 530 shown in FIGS. 15A, 15B, and 15C, the 105 user selects from a list of options for recording the diagnosis of the patient's ulcer. The user may, for example, accept the results by selecting the "confirm and save" button and the system will optionally log any and/or all of the results generated; the user may choose to select the "reject" button to reject the results and the user then has the option to manually change any of the system generated results to what the user believes to be accurate and true. For example, Table 3 shows a list of available ICD-10 codes from which the user may select, namely, the ICD-10 codes currently ranging from L89.000-L89.95. The skilled artisan will appreciate that the ICD-10 codes shown in Table 3 are exemplary, and may at some point be updated to ICD-11 codes and the like. It is to be understood that the presently disclosed subject matter contemplates whatever the most current codes are called, regardless of what they are called at any point in time. Once the appropriate information is showing on screen 530, in various embodiments, the user may then select the "confirm and save" button or any other button shown in screen 530; the user may also choose to select the "back" button to return to the previous screen(s) if a question or item was selected or not selected in error; the user may select the "cancel" button to cancel the entire assessment and not save any information for this assessment.

TABLE 3

| ICD-10 Codes | |
|---|---|
| icd-10 Code | icd-10 Code Description |
| L89.000 | Pressure ulcer of unspecified elbow, unstageable |
| L89.001 | Pressure ulcer of unspecified elbow, stage 1 |
| L89.002 | Pressure ulcer of unspecified elbow, stage 2 |
| L89.003 | Pressure ulcer of unspecified elbow, stage 3 |
| L89.004 | Pressure ulcer of unspecified elbow, stage 4 |
| L89.009 | Pressure ulcer of unspecified elbow, unspecified stage |
| L89.010 | Pressure ulcer of right elbow, unstageable |
| L89.011 | Pressure ulcer of right elbow, stage 1 |
| L89.012 | Pressure ulcer of right elbow, stage 2 |
| L89.013 | Pressure ulcer of right elbow, stage 3 |
| L89.014 | Pressure ulcer of right elbow, stage 4 |
| L89.019 | Pressure ulcer of right elbow, unspecified stage |
| L89.020 | Pressure ulcer of left elbow, unstageable |
| L89.021 | Pressure ulcer of left elbow, stage 1 |
| L89.022 | Pressure ulcer of left elbow, stage 2 |
| L89.023 | Pressure ulcer of left elbow, stage 3 |
| L89.024 | Pressure ulcer of left elbow, stage 4 |
| L89.029 | Pressure ulcer of left elbow, unspecified stage |
| L89.100 | Pressure ulcer of unspecified part of back, unstageable |
| L89.101 | Pressure ulcer of unspecified part of back, stage 1 |
| L89.102 | Pressure ulcer of unspecified part of back, stage 2 |
| L89.103 | Pressure ulcer of unspecified part of back, stage 3 |
| L89.104 | Pressure ulcer of unspecified part of back, stage 4 |
| L89.109 | Pressure ulcer of unspecified part of back, unspecified stage |
| L89.110 | Pressure ulcer of right upper back, unstageable |
| L89.111 | Pressure ulcer of right upper back, stage 1 |
| L89.112 | Pressure ulcer of right upper back, stage 2 |
| L89.113 | Pressure ulcer of right upper back, stage 3 |
| L89.114 | Pressure ulcer of right upper back, stage 4 |
| L89.119 | Pressure ulcer of right upper back, unspecified stage |
| L89.120 | Pressure ulcer of left upper back, unstageable |
| L89.121 | Pressure ulcer of left upper back, stage 1 |
| L89.122 | Pressure ulcer of left upper back, stage 2 |
| L89.123 | Pressure ulcer of left upper back, stage 3 |
| L89.124 | Pressure ulcer of left upper back, stage 4 |
| L89.129 | Pressure ulcer of left upper back, unspecified stage |
| L89.130 | Pressure ulcer of right lower back, unstageable |
| L89.131 | Pressure ulcer of right lower back, stage 1 |
| L89.132 | Pressure ulcer of right lower back, stage 2 |
| L89.133 | Pressure ulcer of right lower back, stage 3 |
| L89.134 | Pressure ulcer of right lower back, stage 4 |
| L89.139 | Pressure ulcer of right lower back, unspecified stage |
| L89.140 | Pressure ulcer of left lower back, unstageable |
| L89.141 | Pressure ulcer of left lower back, stage 1 |
| L89.142 | Pressure ulcer of left lower back, stage 2 |
| L89.143 | Pressure ulcer of left lower back, stage 3 |
| L89.144 | Pressure ulcer of left lower back, stage 4 |
| L89.149 | Pressure ulcer of left lower back, unspecified stage |
| L89.150 | Pressure ulcer of sacral region, unstageable |
| L89.151 | Pressure ulcer of sacral region, stage 1 |
| L89.152 | Pressure ulcer of sacral region, stage 2 |
| L89.153 | Pressure ulcer of sacral region, stage 3 |
| L89.154 | Pressure ulcer of sacral region, stage 4 |
| L89.159 | Pressure ulcer of sacral region, unspecified stage |
| L89.200 | Pressure ulcer of unspecified hip, unstageable |
| L89.201 | Pressure ulcer of unspecified hip, stage 1 |
| L89.202 | Pressure ulcer of unspecified hip, stage 2 |
| L89.203 | Pressure ulcer of unspecified hip, stage 3 |
| L89.204 | Pressure ulcer of unspecified hip, stage 4 |
| L89.209 | Pressure ulcer of unspecified hip, unspecified stage |
| L89.210 | Pressure ulcer of right hip, unstageable |
| L89.211 | Pressure ulcer of right hip, stage 1 |
| L89.212 | Pressure ulcer of right hip, stage 2 |
| L89.213 | Pressure ulcer of right hip, stage 3 |
| L89.214 | Pressure ulcer of right hip, stage 4 |

TABLE 3-continued

ICD-10 Codes

| icd-10 Code | icd-10 Code Description |
|---|---|
| L89.219 | Pressure ulcer of right hip, unspecified stage |
| L89.220 | Pressure ulcer of left hip, unstageable |
| L89.221 | Pressure ulcer of left hip, stage 1 |
| L89.222 | Pressure ulcer of left hip, stage 2 |
| L89.223 | Pressure ulcer of left hip, stage 3 |
| L89.224 | Pressure ulcer of left hip, stage 4 |
| L89.229 | Pressure ulcer of left hip, unspecified stage |
| L89.300 | Pressure ulcer of unspecified buttock, unstageable |
| L89.301 | Pressure ulcer of unspecified buttock, stage 1 |
| L89.302 | Pressure ulcer of unspecified buttock, stage 2 |
| L89.303 | Pressure ulcer of unspecified buttock, stage 3 |
| L89.304 | Pressure ulcer of unspecified buttock, stage 4 |
| L89.309 | Pressure ulcer of unspecified buttock, unspecified stage |
| L89.310 | Pressure ulcer of right buttock, unstageable |
| L89.311 | Pressure ulcer of right buttock, stage 1 |
| L89.312 | Pressure ulcer of right buttock, stage 2 |
| L89.313 | Pressure ulcer of right buttock, stage 3 |
| L89.314 | Pressure ulcer of right buttock, stage 4 |
| L89.319 | Pressure ulcer of right buttock, unspecified stage |
| L89.320 | Pressure ulcer of left buttock, unstageable |
| L89.321 | Pressure ulcer of left buttock, stage 1 |
| L89.322 | Pressure ulcer of left buttock, stage 2 |
| L89.323 | Pressure ulcer of left buttock, stage 3 |
| L89.324 | Pressure ulcer of left buttock, stage 4 |
| L89.329 | Pressure ulcer of left buttock, unspecified stage |
| L89.40 | Pressure ulcer of contiguous site of back, buttock and hip, unspecified |
| L89.41 | Pressure ulcer of contiguous site of back, buttock and hip, stage 1 |
| L89.42 | Pressure ulcer of contiguous site of back, buttock and hip, stage 2 |
| L89.43 | Pressure ulcer of contiguous site of back, buttock and hip, stage 3 |
| L89.44 | Pressure ulcer of contiguous site of back, buttock and hip, stage 4 |
| L89.45 | Pressure ulcer of contiguous site of back, buttock and hip, unstageable |
| L89.500 | Pressure ulcer of unspecified ankle, unstageable |
| L89.501 | Pressure ulcer of unspecified ankle, stage 1 |
| L89.502 | Pressure ulcer of unspecified ankle, stage 2 |
| L89.503 | Pressure ulcer of unspecified ankle, stage 3 |
| L89.504 | Pressure ulcer of unspecified ankle, stage 4 |
| L89.509 | Pressure ulcer of unspecified ankle, unspecified stage |
| L89.510 | Pressure ulcer of right ankle, unstageable |
| L89.511 | Pressure ulcer of right ankle, stage 1 |
| L89.512 | Pressure ulcer of right ankle, stage 2 |
| L89.513 | Pressure ulcer of right ankle, stage 3 |
| L89.514 | Pressure ulcer of right ankle, stage 4 |
| L89.519 | Pressure ulcer of right ankle, unspecified stage |
| L89.520 | Pressure ulcer of left ankle, unstageable |
| L89.521 | Pressure ulcer of left ankle, stage 1 |
| L89.522 | Pressure ulcer of left ankle, stage 2 |
| L89.523 | Pressure ulcer of left ankle, stage 3 |
| L89.524 | Pressure ulcer of left ankle, stage 4 |
| L89.529 | Pressure ulcer of left ankle, unspecified stage |
| L89.600 | Pressure ulcer of unspecified heel, unstageable |
| L89.601 | Pressure ulcer of unspecified heel, stage 1 |
| L89.602 | Pressure ulcer of unspecified heel, stage 2 |
| L89.603 | Pressure ulcer of unspecified heel, stage 3 |
| L89.604 | Pressure ulcer of unspecified heel, stage 4 |
| L89.609 | Pressure ulcer of unspecified heel, unspecified stage |
| L89.610 | Pressure ulcer of right heel, unstageable |
| L89.611 | Pressure ulcer of right heel, stage 1 |
| L89.612 | Pressure ulcer of right heel, stage 2 |
| L89.613 | Pressure ulcer of right heel, stage 3 |
| L89.614 | Pressure ulcer of right heel, stage 4 |
| L89.619 | Pressure ulcer of right heel, unspecified stage |
| L89.620 | Pressure ulcer of left heel, unstageable |
| L89.621 | Pressure ulcer of left heel, stage 1 |
| L89.622 | Pressure ulcer of left heel, stage 2 |
| L89.623 | Pressure ulcer of left heel, stage 3 |
| L89.624 | Pressure ulcer of left heel, stage 4 |
| L89.629 | Pressure ulcer of left heel, unspecified stage |
| L89.810 | Pressure ulcer of head, unstageable |
| L89.811 | Pressure ulcer of head, stage 1 |
| L89.812 | Pressure ulcer of head, stage 2 |
| L89.813 | Pressure ulcer of head, stage 3 |
| L89.814 | Pressure ulcer of head, stage 4 |
| L89.819 | Pressure ulcer of head, unspecified stage |
| L89.890 | Pressure ulcer of other site, unstageable |
| L89.891 | Pressure ulcer of other site, stage 1 |
| L89.892 | Pressure ulcer of other site, stage 2 |

TABLE 3-continued

ICD-10 Codes

| icd-10 Code | icd-10 Code Description |
| --- | --- |
| L89.893 | Pressure ulcer of other site, stage 3 |
| L89.894 | Pressure ulcer of other site, stage 4 |
| L89.899 | Pressure ulcer of other site, unspecified stage |
| L89.90 | Pressure ulcer of unspecified site, unspecified stage |
| L89.91 | Pressure ulcer of unspecified site, stage 1 |
| L89.92 | Pressure ulcer of unspecified site, stage 2 |
| L89.93 | Pressure ulcer of unspecified site, stage 3 |
| L89.94 | Pressure ulcer of unspecified site, stage 4 |
| L89.95 | Pressure ulcer of unspecified site, unstageable |

Once the user selects the "Confirm and Save" button, the information will store in patient data 134 in the data store 114. In one example and referring now to a screen 514 shown in FIG. 7, screen 515 shown in FIG. 8A., and screen 516 shown in FIG. 8B., the user selects from a list of options (e.g., "Print", "Export", or "Back"). For example, if the user selects the "Print" button, the user may choose to print any and all selected and/or displayed information on the current screen; In another example, if the user selects the "Export" option, the user may choose a list of options for exporting the data selected and/or displayed on the current screen (e.g., Export to Excel, PDF, MS Word, email, to EMR, external hard drive, etc.) and then the user may choose to either (1) return to the previous screen using the "back" button or (2) print the information exported. Further, using an "Upload Photo(s)" button, the user may elect to upload one or more digital images of the patient's wound area to the patient's chart. Upon completion of the recording process, in various embodiments, the user may choose to complete another assessment on the existing patient, may select a different patient, or may exit the PUD Tool 112 and the method 400 ends thereafter.

However, if at step 418, no Stage 4 Pressure Ulcer characteristics or symptoms on screen 518 are selected, then no Stage 4 Pressure Ulcer is present (e.g., the particular pressure ulcer is not stage/grade/category 4) and the PUD tool 112 proceeds to step 428. At step 418, information is also received with respect to a Resurfaced Full-thickness Pressure Ulcer. In one example, and referring now to a screen 518, the option stating "This pressure ulcer is or was closed, is or was resurfaced with 100% scar tissue and/or epithelium, AND the last known stage was Unstageable or Unknown," is an option indicating a characteristic or symptom of a Resurfaced Full-thickness Pressure Ulcer. If both symptoms are present, then, in one embodiment, the PUD tool 112 proceeds to step 428.

At a decision step 428, in one embodiment, based on the information provided by the entity assessing the wound in step 418, if no Stage 4 Pressure Ulcer characteristic or symptom was present, the diagnosis module 116 of the PUD tool 112 then determines whether any Resurfaced Full-thickness Pressure Ulcer is present. Namely, if in step 418 the item on screen 518 which states "This pressure ulcer is or was closed, is or was resurfaced with 100% scar tissue and/or epithelium, AND the last known stage was Unstageable or Unknown," is selected because the statement is true, then the Resurfaced Full-thickness Pressure Ulcer characteristic or symptom is present and the PUD tool 112 proceeds to step 430. Generally, an "Unknown" pressure ulcer is a wound that was previously Unstageable or was not staged and healed before the wound was staged by a professional (e.g., a patient arrives in the doctor's office for the first time with a healed pressure ulcer, this wound is Unknown; a patient arrived at a doctor's office with a pressure ulcer that was Unstageable and has returned to the doctor's office after the wound healed, this wound is Unknown).

Further and referring now to screen 518 shown on FIG. 10C., in one embodiment, for all future diagnoses of this pressure ulcer for this patient, if in step 418 the statement on screen 518 which states "This pressure ulcer is or was closed, is or was resurfaced with 100% scar tissue and/or epithelium, AND the last known stage was Unstageable or Unknown," is selected because the statement is true, then the statement as shown on screen 518 shown in FIG. 10C., will be automatically selected and the date this ulcer was initially classified as a Resurfaced Full-thickness Pressure Ulcer may optionally be displayed beside that statement. This feature of the diagnosis module 116 of the PUD tool 112 prevents reverse staging and allows users to easily track stage changes on a pressure ulcer in the medical record. Once the statement which states "This pressure ulcer is or was closed, is or was resurfaced with resurfaced with 100% scar tissue and/or epithelium, AND the last known stage was Unstageable or Unknown," on screen 518 as shown in FIG. 10C., has been selected, in one embodiment, the user cannot deselect this option without an override. For example, in various embodiments, using an "Override" button, the user may select that this option was: (1) previously chosen in error; (2) new staging information has become available that verified this ulcer was never a Stage 4 Pressure Ulcer, which will allow the user 105 to then proceed to step 434; or (3) the optional date showing the date this ulcer was initially classified as that stage, which in the aforementioned example was a stage 4, may also be edited to reflect the information available in the patients' medical record prior to the date the PUD system 100/200 was used if such a date is known. So, in one embodiment, if the ulcer was known to be a Resurfaced Full-thickness Pressure Ulcer on Jan. 1, 2016, but the disclosed system is not used for the first time until Mar. 1, 2016, then the override option would allow the Mar. 1, 2016, date to be changed to the date the ulcer was initially classified as a Resurfaced Full-thickness Pressure Ulcer, which in this example would be on Jan. 1, 2016. However, if at step 418, in one embodiment, the statement on screen 518 shown in FIG. 10C., which states "This pressure ulcer is or was closed, is or was resurfaced with resurfaced with 100% scar tissue and/or epithelium, AND the last known stage was Unstageable or Unknown," is not selected, because the statement is not true, then no Resurfaced Full-thickness Pressure Ulcer is present (e.g., the pressure ulcer is not a Resurfaced Full-thickness Pressure Ulcer) and then the PUD tool 112 proceeds to step 434.

At step 430, the diagnosis module 116 of the PUD tool 112 classifies the patient's ulcer as a Resurfaced Full-thickness Pressure Ulcer, based on the information received at step 418. At step 431, the diagnosis module 116 of the PUD tool 112 generates a medical diagnosis code that correlates to the diagnosis/classification results, the stage of the pressure ulcer, the wound location, the wound status (e.g., active, inactive, marked in error), the wound condition (e.g., open, closed, healed, marked in error, not applicable), the date and time of the current assessment, the date and time of a previous assessment when this pressure ulcer first became this stage (if applicable), and a treatment recommendation. At step 432, using the screen 530 of FIG. 15A as described above in step 425, the diagnosis of the ulcer as a Resurfaced Full-thickness Pressure Ulcer is recorded in the patient data 134 in the data store 114 the patient's chart is closed, and the method 400 ends thereafter.

If, however, at step 428, no Resurface Full-thickness Pressure Ulcer criteria are present, then the PUD tool 112 proceeds to step 434, wherein the user 105 enters information with respect to an "Unstageable Pressure Ulcer. In one embodiment, and referring now to a screen 522 shown in FIG. 11, the user 105 is prompted with the statement "Select the following statement if it is true", followed by the statement, "Slough and/or eschar is obscuring (covering) an area of the wound bed so that the extent of tissue loss cannot be determined." If the statement is true, then, in one embodiment, the user 105 selects the statement. In one embodiment, "unstageable" is also referred to as "unclassified." The user may, in various embodiments, select the "Back" button to review the previous screen (e.g., screen 518); otherwise, the user then selects the "Continue" button.

At a decision step 436, based on the information provided by the user in step 434, the diagnosis module 116 of the PUD tool 112 determines whether any Unstageable Pressure Ulcer characteristics or symptoms are present. Namely, if in step 434 if the statement(s) on screen 522 is selected because the statement(s) is true (e.g., the pressure ulcer is an Unstageable Pressure Ulcer), then an Unstageable Pressure Ulcer is present and the method 400 proceeds to step 438.

Figure 12A:
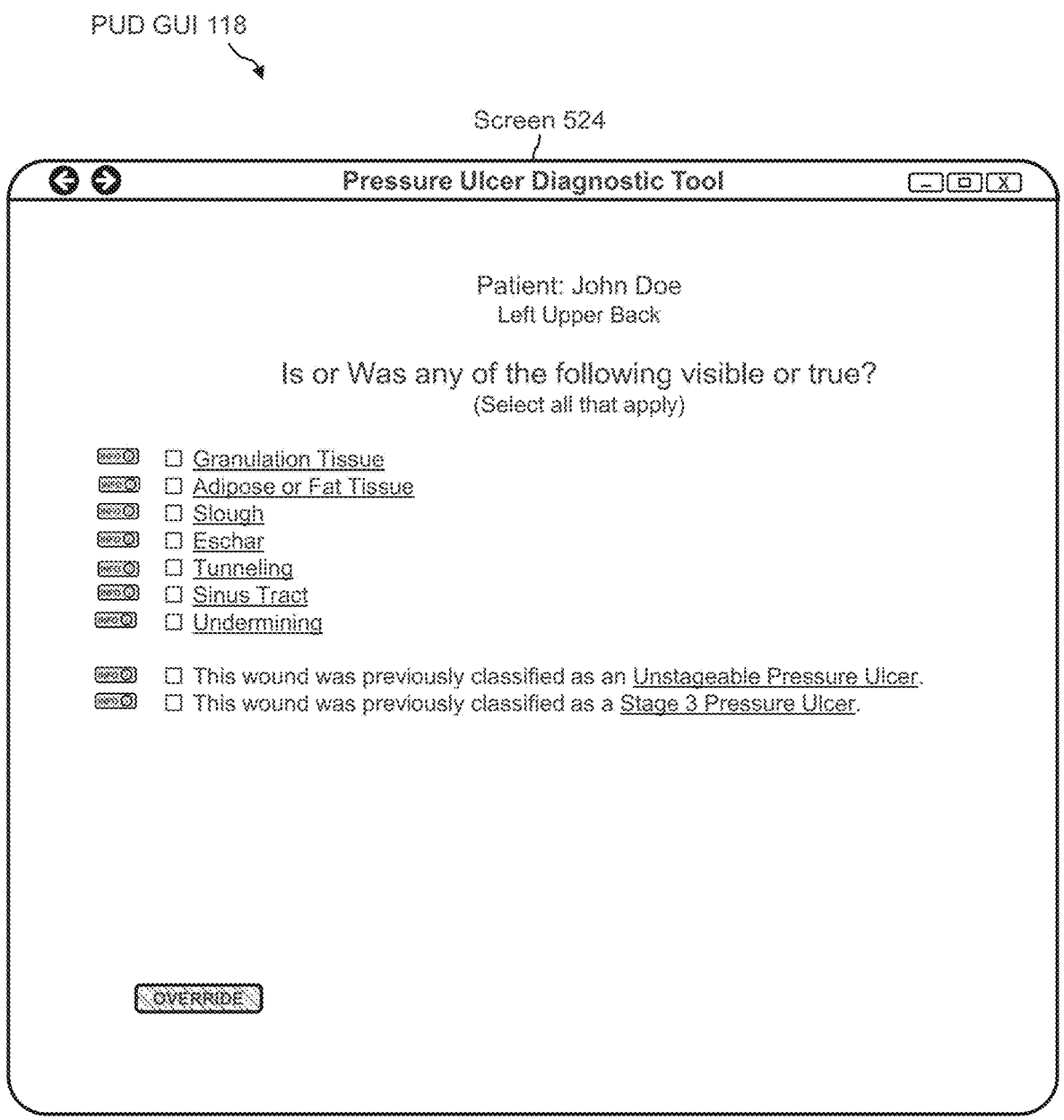
FIG. 12 (consisting of FIGS. 12A, 12B, and 12C) is a screenshot of an exemplary Stage 3 wound classification screen of a PUD system, according to one embodiment of the present disclosure.
Figure 12B:
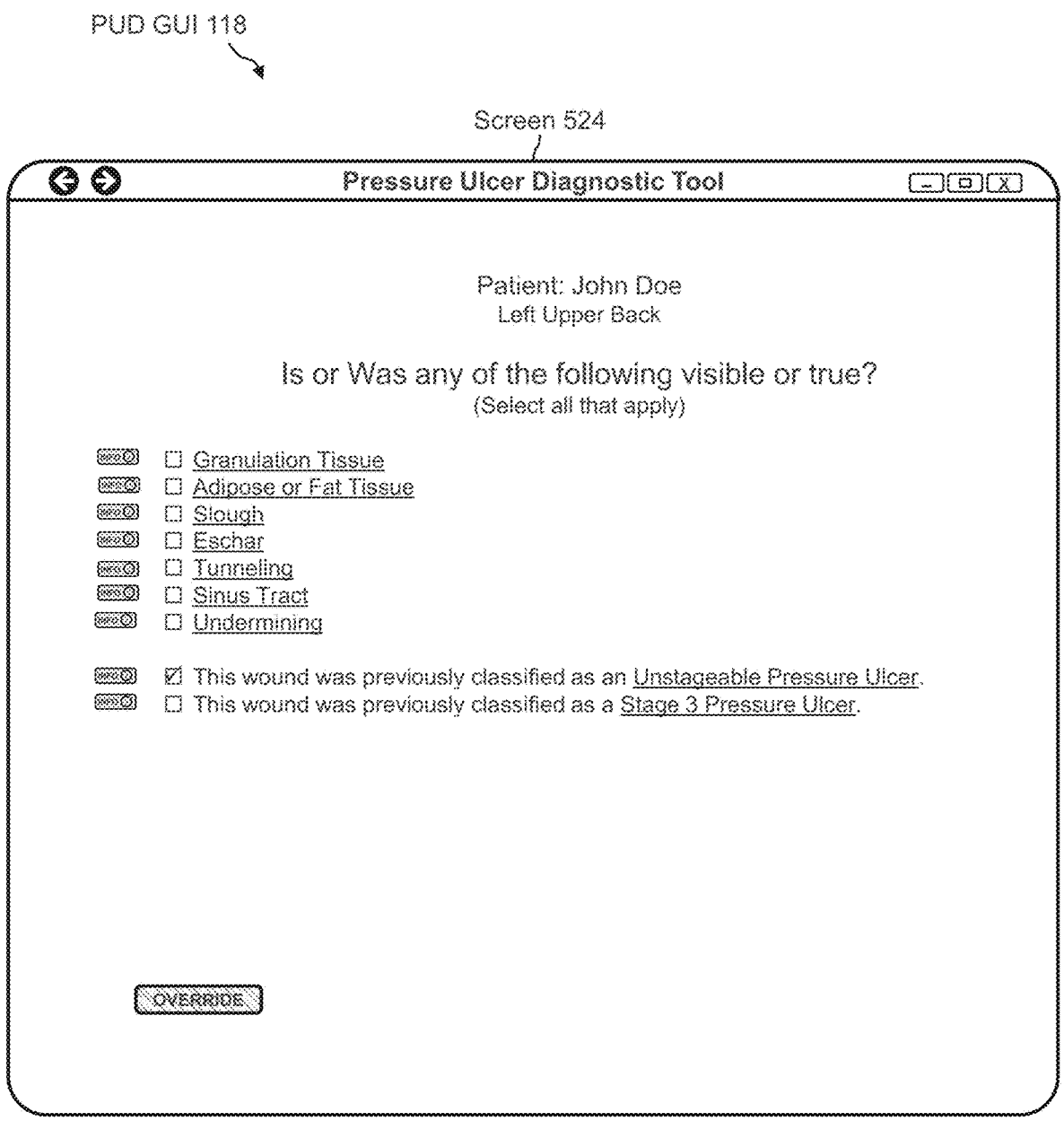
Figure 13:
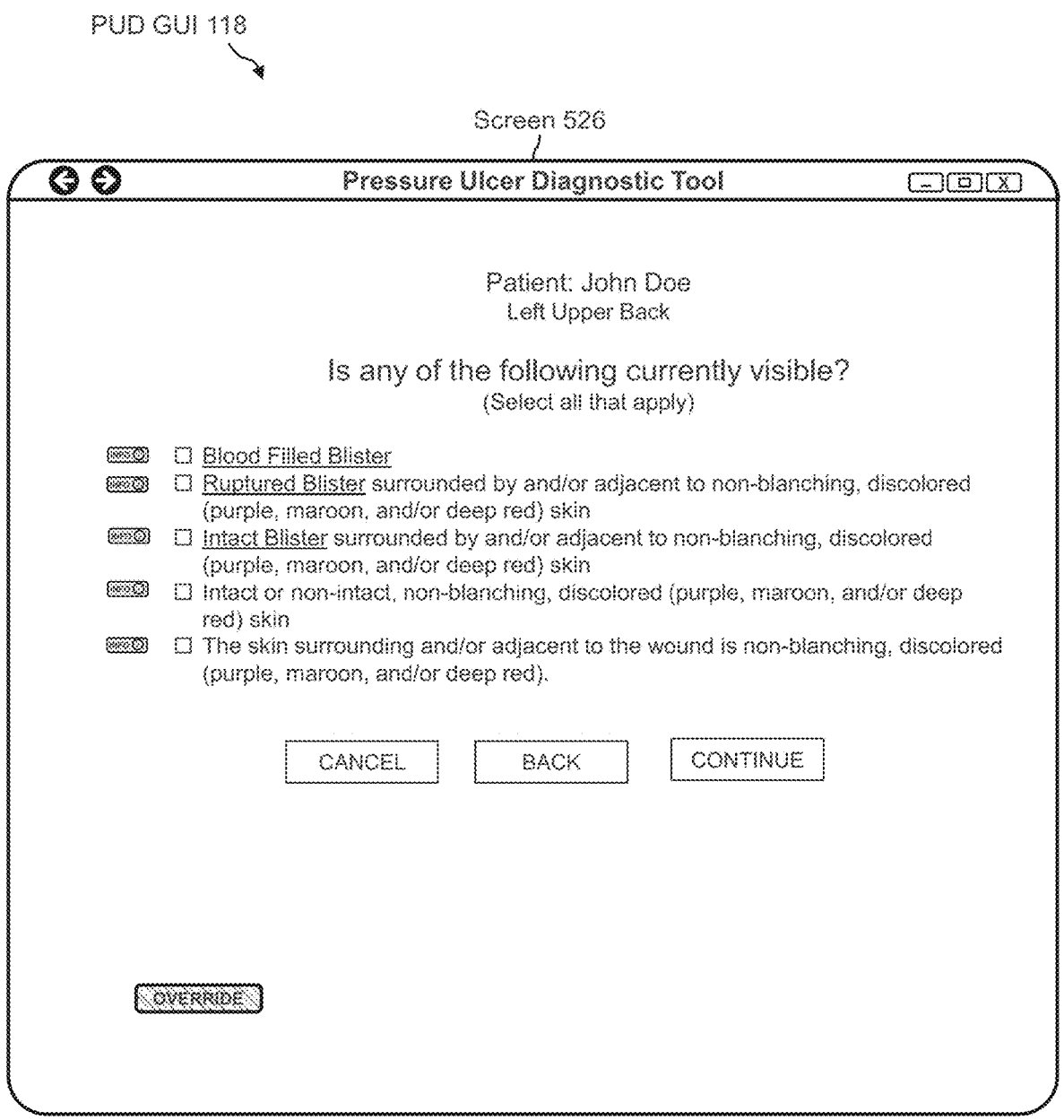
FIG. 13 is a screenshot of an exemplary DTI wound classification screen of a PUD system, according to one embodiment of the present disclosure.

Further and referring now to a screen 524 shown in FIG. 12B, in various embodiments, for all future diagnoses of this pressure ulcer for this patient, if in step 434 the checkbox on screen 522, is selected (which states "Slough, eschar, and/or an non-removable dressing is obscuring (covering) an area of the wound bed so that the extent of tissue loss cannot be determined"), because the statement is true, then the statement "This wound was previously classified as an Unstageable Pressure Ulcer" will be automatically selected, as shown on screen 524 shown in FIG. 12B., and the date this ulcer was initially classified as an Unstageable Pressure Ulcer may optionally be displayed beside that statement. This feature of diagnosis module 116 of the PUD tool 112 allows Unstageable Pressure Ulcers to be later classified as either a Stage 3 Pressure Ulcer, Stage 4 Pressure Ulcer, or a Resurfaced Full-thickness Pressure Ulcer, but prevents staging to any other Pressure Ulcer classification, and allows users 105 to easily track stage/classification changes on a pressure ulcer in the medical record. In one embodiment, once the statement, "This wound was previously classified as an Unstageable Pressure Ulcer," on screen 524 shown in FIG. 12B, is selected, the user cannot deselect this option without an override. For example, using an "Override" button, the user may select that this option was: (1) previously chosen in error; (2) new staging information has become available that verified this ulcer was never an Unstageable Pressure Ulcer (which will allow the user to then proceed to step 442); or (3) the optional date showing the date this ulcer was initially classified as that category/stage/grade, may also be edited to reflect the information available in the patients' medical record prior to the date the PUD system was used if such a date is known. So if the ulcer was known to be an Unstageable Pressure Ulcer on Jan. 1, 2016, but this PUD system 100/200 is not used for the first time until Mar. 1, 2016, the override option would allow the Mar. 1, 2016 date to be changed to the date the ulcer was initially classified as an Unstageable Pressure Ulcer, which in this example would be on Jan. 1, 2016.

At step 438, the diagnosis module 116 of the PUD tool 112 generally classifies the patient's ulcer as an Unstageable Pressure Ulcer. At step 439, in various embodiments, based on the classification as an Unstageable Pressure Ulcer, the diagnosis module 116 of the PUD tool 112 generates a medical diagnosis code that correlates to the diagnosis results, the stage of the pressure ulcer, the wound location, the wound status (e.g., active, inactive, marked in error), the wound condition (e.g., open, closed, healed, marked in error, not applicable), the date and time of the current assessment, the date and time of a previous assessment when this pressure ulcer first became this stage (if applicable), and a treatment recommendation. At step 440, in one embodiment, using the screen 530 of FIG. 15A described above in step 424, the diagnosis/classification of the ulcer as an Unstageable Pressure Ulcer is recorded in the patient data 134 in the data store 114, the patient's chart is closed, and the method 400 ends thereafter.

However, in one embodiment, if at step 434 the item(s) on screen 522 is not checked because the statement is not true (e.g., the symptoms are not present), then no Unstageable Pressure Ulcer characteristic or symptom is present (e.g., the pressure ulcer is not an Unstageable Pressure Ulcer) and then the method 400 proceeds to step 442 (shown in FIG. 4C).

At step 442, in various embodiments, the user 105 enters information with respect to a Stage 3 Pressure Ulcer. In one example, and referring now again to screen 524 shown in FIG. 12A, the user 105 is prompted to answer the question, "Is or Was any of the following visible or true?" To answer this question, the user 105 selects all of the symptoms/characteristics that apply from a list of conditions (e.g., "Adipose or Fat Tissue", "Granulation Tissue", "Slough", "Eschar", "Sinus Tract", "Tunneling", and/or "Undermining", "This wound was previously classified as a Stage 3 Pressure Ulcer", "This wound was previously classified as an Unstageable Pressure Ulcer", etc.). In one embodiment, the user 105 may select the "Back" button to review the previous screen. In one embodiment, the user 105 then selects the "Continue" button.

At a decision step 444, in one embodiment, based on the information provided by the user at step 442, the diagnosis module 116 of the PUD tool 112 determines whether any Stage 3 Pressure Ulcer characteristic or symptom is present. Namely, in one embodiment, if at step 442 any one or more conditions on screen 524 are selected, then a Stage 3 Pressure Ulcer characteristic or symptom is present (e.g., the pressure ulcer is Stage 3 Pressure Ulcer) and the PUD tool 112 proceeds to step 446.

Further and referring now to FIG. 12C, in one embodiment, for all future diagnoses of this pressure ulcer for this patient, if in step 442 any one or more conditions on screen 524 are selected, then the "This wound was previously classified as a Stage 3 Pressure Ulcer" checkbox will be automatically selected and the date this ulcer was initially classified as a Stage 3 Pressure Ulcer may optionally be displayed beside that statement. This feature of the diagnosis module 116 of the PUD tool 112 generally prevents reverse staging and allows users to easily track stage changes on a pressure ulcer in the medical record. Once "This wound was previously classified as a Stage 3 Pressure Ulcer" is selected, in one embodiment, the user 105 cannot deselect this option without an override. For example, using an "OVERRIDE" button, the user 105 may select that this option was: (1) previously chosen in error; (2) new staging information has become available that verified this ulcer was never a Stage 3 Pressure Ulcer, which will allow the user 105 to proceed to step 450; or (3) the optional date showing the date this ulcer was initially classified as that Stage 3 Pressure Ulcer may also be edited to reflect the information available in the patients' medical record prior to the date the PUD system 100/200 was used if such a date is known. For example, if the ulcer was known to be a Stage 3 Pressure Ulcer on Jan. 1, 2016, but this PUD system 100/200 is not used for the first time until Mar. 1, 2016, the override option would allow the Mar. 1, 2016, date to be changed to the date the ulcer was initially classified as a Stage 3 Pressure Ulcer, which in this example would be on Jan. 1, 2016.

At step 446, in various embodiments, the diagnosis module 116 of the PUD tool 112 classifies the patient's ulcer as a Stage 3 Pressure Ulcer, based on the information received at step 442. At step 447, the diagnosis module 116 of the PUD tool 112 generates a medical diagnosis code that correlates to the diagnosis results, the stage of the pressure ulcer, the wound location, the wound status (e.g., active, inactive, marked in error, etc.), the wound condition (e.g., open, closed, healed, marked in error, not applicable, etc.), the date and time of the current assessment, the date and time of a previous assessment when this pressure ulcer first became this stage (if applicable), and a treatment recommendation. At step 448, in one embodiment, using the screen 530 of FIG. 15A, as described above in step 424, the diagnosis of the ulcer as a Stage 3 Pressure Ulcer is recorded in the patient data 134 in the data store 114 and the patient's chart is closed, and the method 400 ends thereafter.

However, if at step 442, in one embodiment, no conditions on screen 524 are selected, then no Stage 3 Pressure Ulcer is present (e.g., the pressure ulcer is not Stage 3 Pressure Ulcer) and the PUD tool 112 proceeds to step 450. At step 450, the user 105 generally enters information with respect to a "Deep tissue Injury" (DTI). In one example and referring, now to a screen 526 shown in FIG. 13, the user 105 is prompted to answer the question "Is any of the following currently visible?" To answer the question, in various embodiments, the user 105 selects any and all symptoms or characteristics that apply from a list of conditions (e.g., "Blood filled blister", "Ruptured blister surrounded by and/or adjacent to discolored purple, maroon, and/or deep red intact skin", "Intact blister surrounded by and/or adjacent to non-blanching discolored purple, maroon, and/or deep red intact skin", "Intact and non-intact non-blanching discolored purple, maroon, and/or deep red skin", and "The skin surrounding or adjacent to the wound is non-blanching and discolored purple, maroon, and/or deep red", etc.). The user 105 may generally select the "Back" button to review the previous screen (e.g., screen 524) or the "Continue" button.

At a decision step 452, based on the information provided by the user 105 in step 450, the diagnosis module 116 of the PUD tool 112 determines whether any DTI characteristic or symptom is present. Namely, if in step 450, in one embodiment, any one or more conditions on screen 526 are selected, then a DTI is present (e.g., the pressure ulcer is DTI) and the PUD tool 112 proceeds to step 454. The diagnosis module 116 of the PUD tool 112 generally prevents reverse staging a DTI pressure ulcer to a Stage 2 Pressure Ulcer or a Stage 1 Pressure Ulcer, in the event that the DTI has presented in addition to any characteristics or symptoms of a Stage 1 or Stage 2 Pressure Ulcer. Additionally, all the previous steps of method 400 generally still allow for a DTI to be classified as a Stage 4 Pressure Ulcer, a Resurfaced Full-thickness Pressure Ulcer, an Unstageable Pressure Ulcer, or a Stage 3 Pressure Ulcer, depending which Stage characteristics and symptoms presented.

At step 454, the diagnosis module 116 of the PUD tool 112, in one embodiment, classifies the patient's ulcer as a "Deep tissue Injury." At step 455, the diagnosis module 116 of the PUD tool 112, in various embodiments, generates a medical diagnosis code that correlates to the diagnosis results, the stage of the pressure ulcer, the wound location, the wound status (e.g., active, inactive, marked in error, etc.), the wound condition (e.g., open, closed, healed, marked in error, not applicable, etc.), the date and time of the current assessment, the date and time of a previous assessment when this pressure ulcer first became this stage (if applicable), and a treatment recommendation. At step 456, using the screen 530 of FIG. 15A, as described above in step 424, the diagnosis of the wound as a Deep Tissue Injury is generally recorded in the patient data 134 in the data store 114, the patient's chart is closed, and the method 400 ends thereafter.

However, if at step 450, in one embodiment, no conditions on screen 526 are selected, then no DTI characteristic or symptom is present (e.g., the pressure ulcer is not a DTI) and the method 400 proceeds to step 458. At step 458, the user generally enters information with respect to a Stage 2 Pressure Ulcer. In one example, and referring now to a screen 528 shown in FIG. 14, the user 105 is prompted to answer the question "Is any of the following currently visible?" To answer the question, the user 105 generally selects all that apply from a list of characteristics or symptoms (e.g., "Intact blister", "Ruptured blister", "Shallow open wound with exposed dermis usually with a red and/or pink wound bed", etc.). The user 105 may generally select the "Back" button to review the previous screen (e.g., screen 526) or the "Continue" button.

At a decision step 460, based on the information provided by the user in step 458, the diagnosis module 116 of the PUD tool 112, in various embodiments, determines whether any Stage 2 Pressure Ulcer characteristic or symptom is present. Namely, in one embodiment, if at step 458 any one or more Stage 2 Pressure Ulcer characteristics or symptoms on screen 528 are selected, then a Stage 2 Pressure Ulcer is present (e.g., the pressure ulcer is Stage/grade/category 2) and the method 400 proceeds to step 462. The diagnosis module 116 of the PUD tool 112 generally prevents inaccurately staging a Stage 2 Pressure Ulcer. The user 105 may generally choose to override this classification. For example, using an "Override" button, the user may select that this option was: (1) previously chosen in error; (2) new staging information has become available that verified this ulcer was never a Stage 2 Pressure Ulcer (which will allow the user to then proceed to step 466); or (3) the optional date showing the date this ulcer was initially classified as that category/stage/grade, may also be edited to reflect the information available in the patients' medical record prior to the date the PUD system 100/200 was used if such a date is known. For example, if the ulcer was known to be a Stage 2 Pressure Ulcer on Jan. 1, 2016, but this PUD system 100/200 is not used for the first time until Mar. 1, 2016, the override option would allow the Mar. 1, 2016, date to be changed to the date the ulcer was initially classified as a Stage 2 Pressure Ulcer, which in this example would be on Jan. 1, 2016.

At step 462, the diagnosis module 116 of the PUD tool 112 generally classifies the patient's ulcer as a Stage 2 Pressure Ulcer. At step 463, in one embodiment, the diagnosis module 116 of the PUD tool 112 generates a medical diagnosis code that correlates to the diagnosis results, the stage of the pressure ulcer, the wound location, the wound status (e.g., active, inactive, marked in error, etc.), the wound condition (e.g., open, closed, healed, marked in error, not applicable, etc.), the date and time of the current assessment, the date and time of a previous assessment when this pressure ulcer first became this stage (if applicable), and a treatment recommendation. At step 464, using the screen 530 of FIG. 15A, as described above in step 424, the diagnosis of the wound as a Stage 2 Pressure Ulcer is generally recorded in the patient data 134 in the data store 114, the patient's chart is closed, and the method 400 ends thereafter.

However, if at step 458, in one embodiment, no characteristic or symptom on screen 528 is selected, then no Stage 2 Pressure Ulcer is present (e.g., the pressure ulcer is not a stage/grade/category 2) and the PUD tool 112 proceeds to step 466. At step 466, the user 105 generally enters information with respect to a Stage 1 Pressure Ulcer. In one example, and referring now to a screen 528 shown in FIG. 14, the user is prompted to answer the question "Is any of the following currently visible?" To answer the question, the user 105 selects whether any Stage 1 Pressure Ulcer (e.g., "Intact skin with non-blanching erythema/redness") applies to the wound being assessed. The user 105 generally may select the "Back" button to review the previous screen (e.g., screen 526) or the "Continue" button.

At a decision step 468, based on the information provided by the assessing user 105 at step 466, the diagnosis module 116 of the PUD tool 112 generally determines whether any Stage 1 Pressure Ulcer characteristic or symptom is present. Namely, if in step 466 any one or more conditions on screen 528 are selected, then, in one embodiment, a Stage 1 Pressure Ulcer is present (e.g., the pressure ulcer is Stage/Grade/Category 1 Pressure Ulcer) and the PUD tool 112 proceeds to step 470. The user 105 generally may choose to override this classification. For example, using an "Override" button, the user may select that this option was: (1) previously chosen in error; (2) new staging information has become available; or (3) the optional date showing the date this ulcer was initially classified as that category/stage/grade, may also be edited to reflect the information available in the patients' medical record prior to the date the PUD system was used if such a date is known. For example, if the ulcer was known to be a Stage 1 Pressure Ulcer on Jan. 1, 2016, but this PUD system 100/200 is not used for the first time until Mar. 1, 2016, the override option would allow the Mar. 1, 2016, date to be changed to the date the ulcer was initially classified as a Stage 1 Pressure Ulcer, which in this example would be on Jan. 1, 2016.

At step 470, the diagnosis module 116 of the PUD tool 112 generally classifies the patient's ulcer as a Stage 1 Pressure Ulcer. At step 471, the diagnosis module 116 of the PUD tool 112, in various embodiments, generates a medical diagnosis code that correlates to the diagnosis results, the stage of the pressure ulcer, the wound location, the wound status (e.g., active, inactive, marked in error, etc.), the wound condition (e.g., open, closed, healed, marked in error, not applicable, etc.), the date and time of the current assessment, the date and time of a previous assessment when this pressure ulcer first became this stage (if applicable), and a treatment recommendation. At step 472, using the screen 530 of FIG. 15A., as described above in step 424, the diagnosis of the wound as a Stage 1 Pressure Ulcer is generally recorded in the patient data 134 in the data store 114, the patient's chart is closed, and the method 400 ends thereafter.

Figure 14:
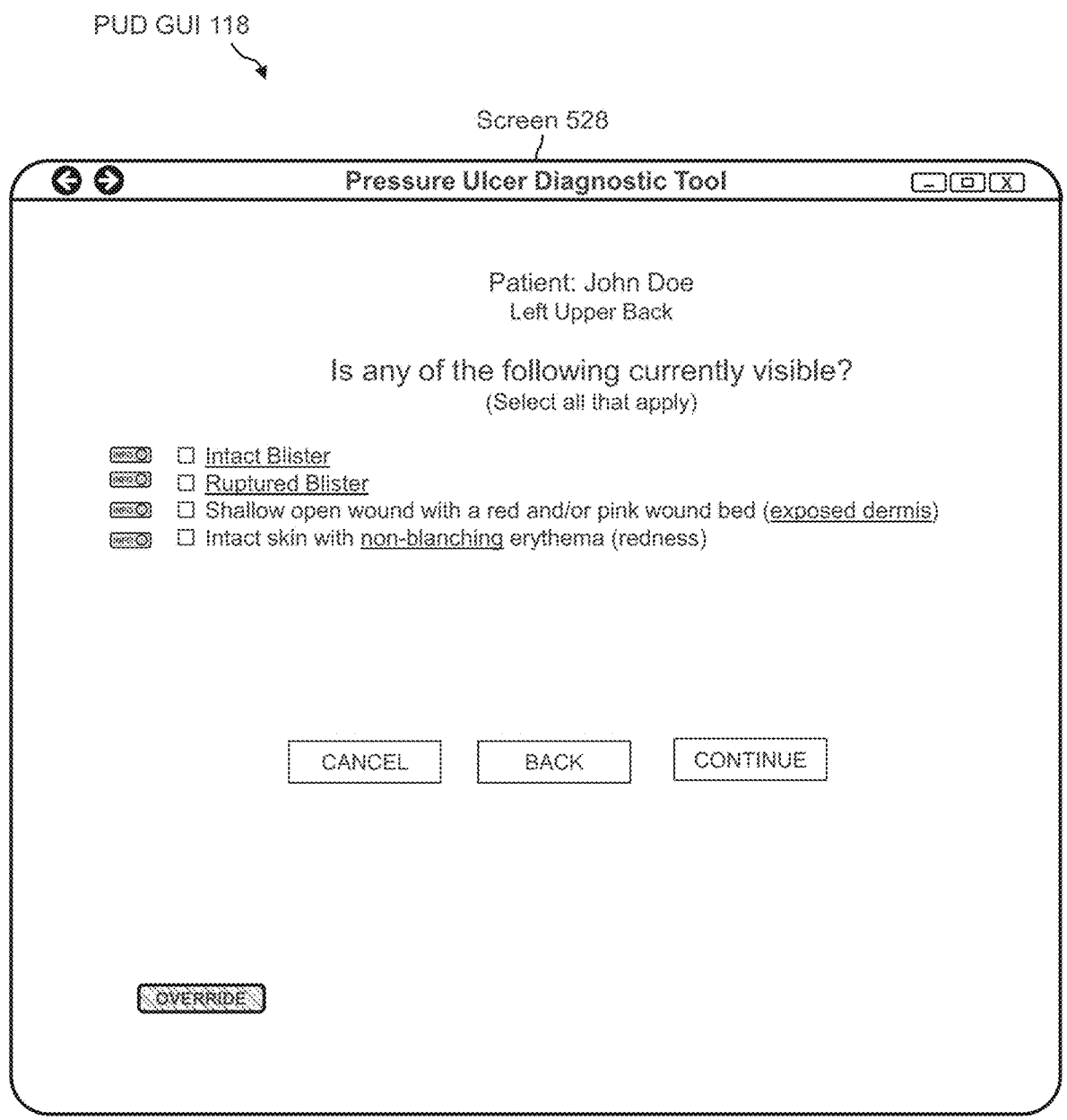
FIG. 14 is a screenshot of an exemplary Stage 2/Stage 1 wound classification screen of a PUD system, according to one embodiment of the present disclosure.

However, if at step 466, in one embodiment, no conditions on screen 530 are selected, then no Stage 1 Pressure Ulcer is present (e.g., the pressure ulcer is not Stage/Grade/Category 1 Pressure Ulcer), and the PUD tool 112 proceeds to step 474. At step 474, the patient's lesion is generally classified as "not a pressure ulcer." In one example, and referring now to a screen 528 shown in FIG. 14, the user 105 is prompted to answer the question "Is any of the following statement currently visible," and the user 105 selects any and all that apply from a list of characteristics or symptoms (e.g., "Intact blister", "Ruptured blister", "Shallow open wound with exposed dermis usually with a red and/or pink wound bed", "Intact skin with non-blanching erythema/redness", etc.). The user may generally select the "Back" button to review the previous screen (e.g., screen 526). If the user does not select any of the characteristics or symptoms, then the diagnosis module 116 of the PUD tool 112, in one embodiment, classifies the stage of the lesion as "not a pressure ulcer." A message will generally display in the Stage section of screen 530 (not shown) which states, "This is not a pressure ulcer but may become one if pressure is not relieved; This diagnosis is complete." In one embodiment, the wound status will be classified by the system as "Inactive." The wound condition, in one embodiment, will be classified by the system as "Not applicable." The medical diagnosis code, in one embodiment, will be displayed as not applicable or N/A. The date and time of the assessment will be generally displayed as the current date and time the assessment was entered. In various embodiments, the user may override this selection using an "Override" button, if this option was either: (1) previously chosen in error; or (2) new staging information has become available that verified this ulcer was indeed determined as a pressure ulcer but the user 105 will need to begin the entire method 400 over with the new and/or correct classification/staging information again, which will allow the PUD tool 112 to then proceed to step 416. If none of the characteristics or symptoms on screen 528, as shown in FIG. 14, are selected, then the diagnosis module 116 of the PUD tool 112 will generally classify the lesion as "not a pressure ulcer." The user may generally select the "Back" button to review the previous screen (e.g., screen 526) or the "Continue" button.

At step 475, the diagnosis module 116 of the PUD tool 112, in various embodiments, generates a medical diagnosis code that correlates to the diagnosis results, the stage of the pressure ulcer, the wound location, the wound status (e.g., active, inactive, marked in error), the wound condition (e.g., open, closed, healed, marked in error, not applicable), the date and time of the current assessment, the date and time of a previous assessment when this pressure ulcer first became this stage (if applicable), and a treatment recommendation. At step 476, using the screen 530 of FIG. 15A., as described above in step 424, in one embodiment, the diagnosis of the lesion as "N/A" will be recorded in the patient data 134 in the data store 114, the patient's chart is closed, and the method 400 ends thereafter. If this is determined as "not as pressure ulcer", generally no ICD-10 or any other corresponding medical diagnosis code will be assigned. In one embodiment, the option on screen 530 as shown in FIG. 15C, which displays the diagnosis in the patients' medical record will be unavailable for selection. The wound status generally will be assigned as "inactive," and the wound condition, in one embodiment, will be listed as "not applicable."

When using the method 400, the PUD tool 112 ensures, for example, that terms (such as bone, muscle, tendon, ligament, fascia, joint capsule, other supporting structures, Stage 4 Pressure Ulcer, "closed is or was 100% scar tissue," Unstageable Pressure Ulcer, Unknown Stage, slough, eschar, granulation tissue, adipose or fat tissue, tunneling, undermining, sinus tract, Stage 3 Pressure Ulcer, Blood filled blister, Ruptured blister, Intact blister, Intact discolored non-blanching skin, Intact skin, Persistently discolored & non-blanching) regarding any stage/grade/category of pressure ulcers have information (e.g., description, definitions, hyperlinks, photos, instructions, etc.) that may be selected by the user 105. This information helps the user (e.g., the user 105) make a more educated, informed decision about what they are truly visualizing and assessing regarding the patients' pressure ulcer. Accordingly, at any time during the pressure ulcer diagnostic process of the method 400, the user (e.g., the user 105) may view selection-specific information (e.g., description, definitions, hyperlinks, photos, etc.) about any stage/grade/category of pressure ulcers. Namely, in one embodiment, an "INFO" button is provided next to each of the selection items on each of the screens of the PUD GUI 118. These "INFO" buttons generally allow selection-specific information tobe displayed to the user. In an example, FIG. 12C shows an example of items displayed in PUD GUI 118 that are hyperlinked, wherein content, description, definitions, and/or photos about the selected hyperlink may be displayed. By way of example, screen 524 shown in FIG. 12C in window 1205 contains content about "Tunneling" when the "Tunneling" hyperlink is selected. Any of the items in any of the screens in PUD GUI 118 may be similarly hyperlinked.

Figure 15A:
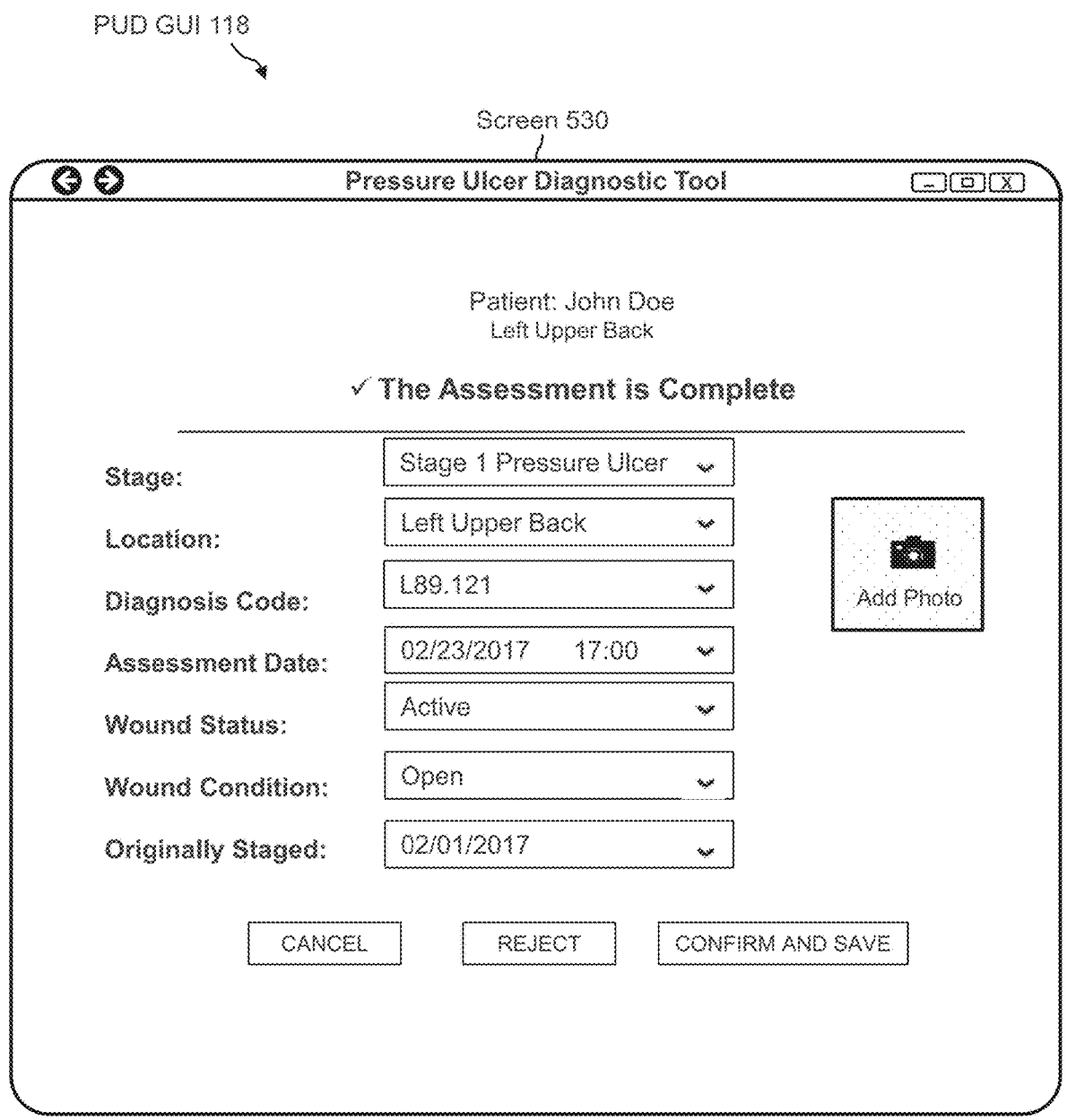
FIG. 15 (consisting of FIGS. 15A, 15B, and 15C) is a screenshot of an exemplary wound classification recordation screen of a PUD system, according to one embodiment of the present disclosure.

Other exemplary features/embodiments of the PUD tool 112 of the PUD system 100 of FIG. 1 and the networked PUD system 200 of FIG. 2 comprise:

(1) ensuring the rationale for the stage assigned to the patient will be in the patients' medical record. An option may generally be selected that will display all the previously stored diagnoses on the monitor so the diagnoses may be reviewed easily (e.g., as part of step 308). Having this tool in an EMR will assist with collaboration of care for healthcare providers within the same network on a shared EMR system, with access to a common EMR system or with shared access to the PUD system 100 in FIG. 1 or the networked PUD system 200 in FIG. 2. For example, the "history" button shown on screen 514 of FIG. 7 allows the user to view and sort all past diagnoses (as seen in screen 515 shown in FIG. 8A);

(2) suggesting the pressure ulcer classification and the suggested ICD-10 code (based on the location and the suggested stage), such as on screen 530 of FIG. 15A;

(3) allowing the user (e.g., the user 105) to choose which classification terms should be used, choices including: Pressure Ulcer, Pressure Injury, Bedsore, Decubitus Ulcer; Stage, Grade, or Category; Unstageable, Ungradable, or Unclassified; Resurfaced Full-thickness Pressure Ulcer or Resurfaced Full-thickness Pressure Ulcer of Unspecified Stage; Suspected Deep Tissue Pressure Injury, Deep Tissue Pressure Injury, Suspected Deep Tissue Injury, or Deep Tissue Injury (based on the healthcare providers preferred or required terms);

(4) allowing for the different classification/staging system guidelines to be used, including the National Pressure Ulcer Advisory Panel (NPUAP) guidelines, the European Pressure Ulcer Advisory Panel Guidelines (EPUAP), the Pan Pacific Pressure Injury Alliance, CMS, WHO, and the MDS Guidelines;

(5) allowing for the final stage and medical diagnosis code along with the date and time of the assessment, the date the wound became the determined diagnosis, wound condition, wound status, stage, location, photo, and the rationale for the stage to be printed or exported.

(6) not allowing ulcers that are not caused by pressure and/or pressure in conjunction with shear to be classified using this system;

(7) not allowing pressure ulcers on the mucous membrane to be classified using this staging system (an optional feature).

The presently disclosed PUD system 100 and the PUD tool 112 are not limited to the screens of the PUD GUI 118 that are shown in FIG. 5 through FIG. 17, nor is the operation of the presently disclosed PUD system 100 and the PUD tool 112 limited precisely to the steps described in the method 400 of FIG. 4A, FIG. 4B, FIG. 4C, and FIG. 4D. In various embodiments, the prompts, questions, answers, and responses disclosed herein (of the method 400 and in FIGS. 5-23) describe decisions made by the disclosed system when analyzing a digital image, when classifying a pressure ulcer, etc.

Figure 18:
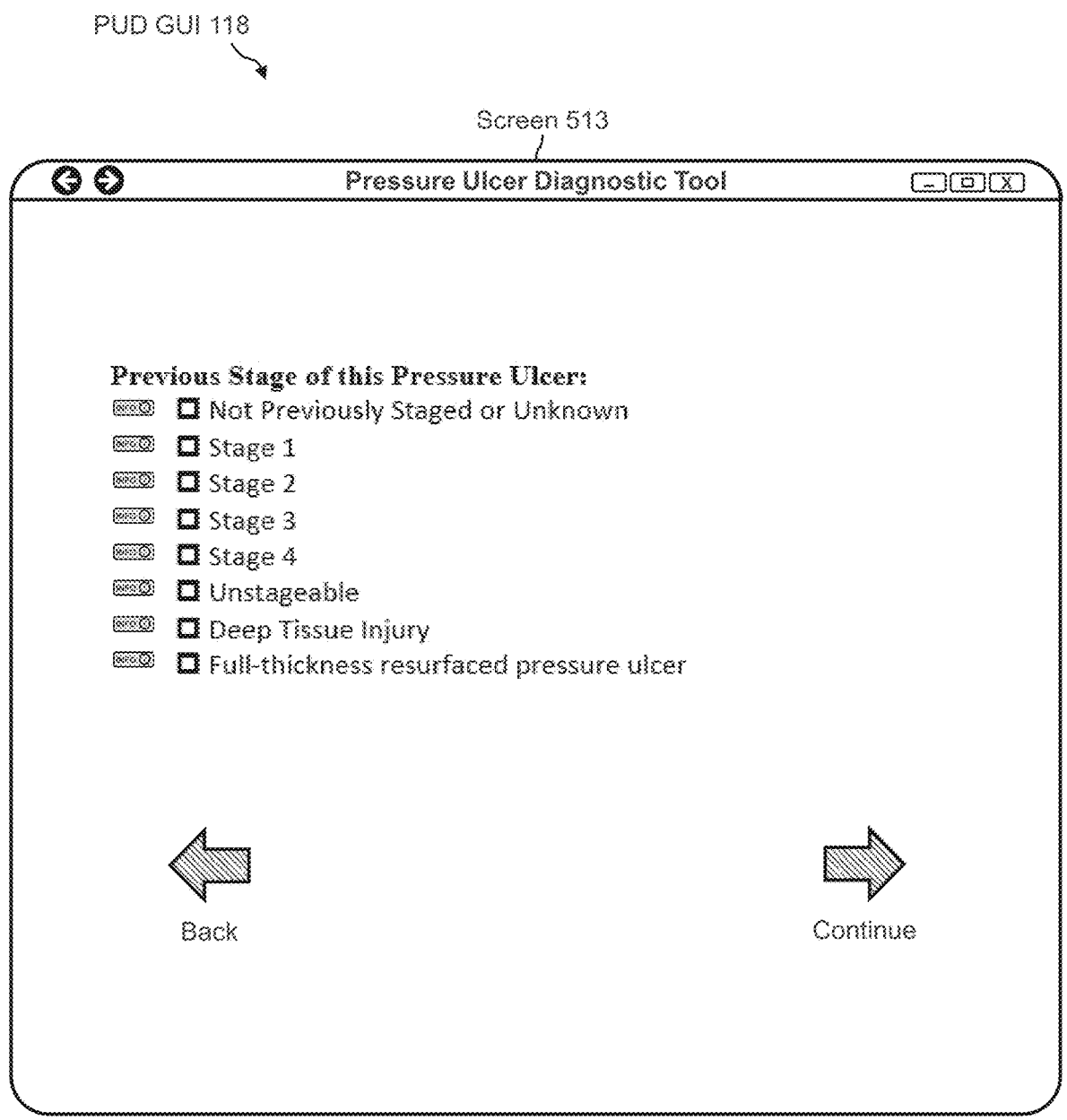
FIG. 18 is a screenshot of an alternative exemplary wound previous classification screen of a PUD system, according to one embodiment of the present disclosure.

Another example of the screens of the PUD GUI 118 and the ulcer classification method are described herein below regarding FIG. 18 through FIG. 23. In this example, certain functions previously described in the method 400 are performed by the PUD tool 112 in a hierarchy of steps performed in the background. Namely, in one embodiment, FIG. 18 shows another example of how the disclosed system may work by changing the order of the questions by separating out the questions about previous stage from FIGS. 10, 12A, and 12B, by asking the particular "Previous stage of this pressure ulcer" as shown in FIG. 18 of screen 513. In screen 513 of FIG. 18, if "Stage 3 Pressure Ulcer" is selected, then the PUD tool 112 may generally ensure this will remain a Stage 3 Pressure Ulcer, without allowing the pressure ulcer to be classified as a Stage 1 Pressure Ulcer, Stage 2 Pressure Ulcer, or a Deep Tissue Injury, at any subsequent assessment, unless an override is made, while still allowing the pressure ulcer to be classified as a Stage 4 Pressure Ulcer, Resurfaced Full-thickness Pressure Ulcer, or as an Unstageable Pressure Ulcer, at a later assessment, depending on the characteristics or symptoms that present, as previously described and shown in FIG. 4. If "Stage 4 Pressure Ulcer" is selected, then, in one embodiment, the PUD tool 112 will ensure that the particular pressure ulcer will be classified as a Stage 4 Pressure Ulcer no matter what other selections are made on subsequent assessments. If an "Unstageable Pressure Ulcer" is selected, then, in one embodiment, the PUD tool 112 will ensure that the particular pressure ulcer will either remain as an Unstageable Pressure Ulcer, without allowing the pressure ulcer to be classified as a Stage 1 Pressure Ulcer, Stage 2 Pressure Ulcer, or a Deep Tissue Injury, at any subsequent assessment, unless an override is made, while still allowing the pressure ulcer to be classified as a Stage 4 Pressure Ulcer, Resurfaced Full-thickness Pressure Ulcer, or a Stage 3 Pressure Ulcer at a later assessment, depending on the characteristics or symptoms that present, as previously described and shown in FIG. 4. If "Resurfaced Full-thickness Pressure Ulcer" is selected, then, in one embodiment, the PUD tool 112 will ensure that this particular pressure ulcer will remain classified as a Resurfaced Full-thickness Pressure Ulcer without allowing the pressure ulcer to be classified as a Stage 1 Pressure Ulcer, Stage 2 Pressure Ulcer, Deep Tissue Injury, Stage 3 Pressure Ulcer, or an Unstageable Pressure Ulcer at any subsequent assessment, unless an override is made, while still allowing the pressure ulcer to be classified as a Stage 4 Pressure Ulcer at a later assessment, depending on the characteristics or symptoms that present, as previously described and shown in FIG. 4.

FIG. 19 is a screenshot of an alternative exemplary Stage 4 wound classification screen of a PUD system, according to one embodiment of the present disclosure. Generally, FIG. 19 shows screen 518, as previously shown in FIG. 10, as described in step 418 of the method 400. In this example, the statement "This wound was previously classified as a Stage 4 Pressure Ulcer" shown previously in FIG. 10 is omitted. If any Stage 4 Pressure Ulcer characteristics or symptoms on either screen 513 shown in FIG. 18 or on screen 518 shown in FIG. 19 are selected, in various embodiments, then the PUD tool 112 will classify this particular pressure ulcer as a Stage 4 Pressure Ulcer, regardless of any other subsequent selections, and optionally, the date this wound was first classified as a Stage 4 Pressure Ulcer will be stored on all future assessments beside the characteristic "Stage 4 Pressure Ulcer" on screen 513 shown in FIG. 18.

FIG. 19, in one embodiment, also shows screen 518 as previously shown in FIG. 10, as described in step 428 of the method 400. If any Resurfaced Full-thickness Pressure Ulcer characteristics or symptoms on screen 513 shown in FIG. 18 or on screen 518 shown in FIG. 19 are selected, (namely the statement "This pressure ulcer is or was closed, is or was 100% scar tissue, and the previous stage was Unknown or an Unstageable Pressure Ulcer" or "Resurfaced Full-thickness Pressure Ulcer"), in various embodiments, and no Stage 4 Pressure Ulcer characteristics or symptoms were selected, then the PUD tool 112 will classify this as a Resurfaced Full-thickness Pressure Ulcer, regardless of any subsequent selections, and optionally, the date this wound was first classified as a Resurfaced Full-thickness Pressure Ulcer will be stored on all future assessments beside the characteristic "Resurfaced Full-thickness Pressure Ulcer" on screen 513 shown in FIG. 18.

Figure 20:
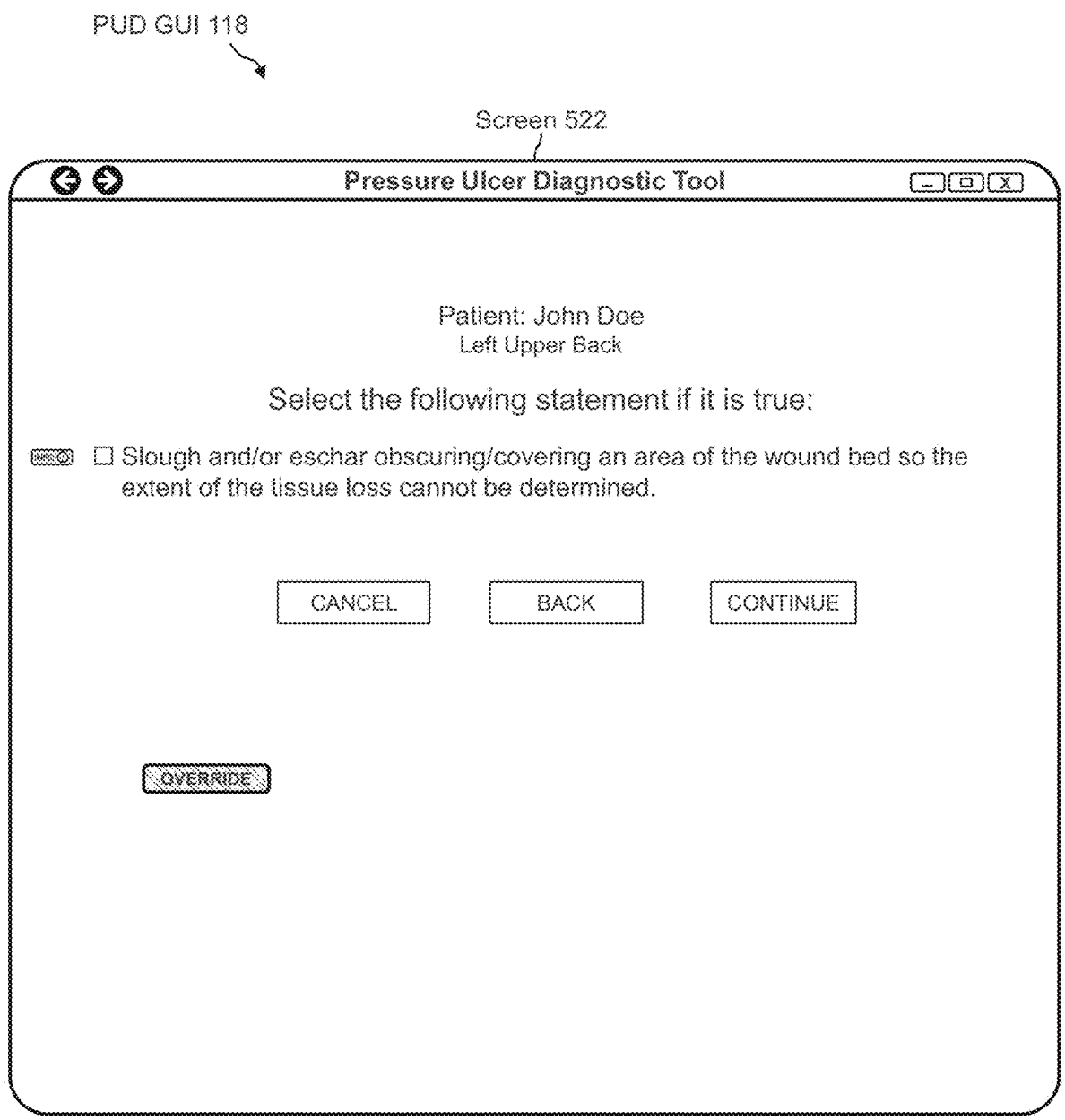
FIG. 20 is a screenshot of an alternative exemplary unstageable wound classification screen of a PUD system, according to one embodiment of the present disclosure.

FIG. 20 is a screenshot of an alternative exemplary unstageable wound classification screen of a PUD system, according to one embodiment of the present disclosure. FIG. 20 generally shows screen 522 previously shown in FIG. 11 and described in step 434 of the method 400. If this ulcer has never been classified as a Stage 4 Pressure Ulcer or a Resurfaced Full-thickness Pressure Ulcer, and consequently "Stage 4 Pressure Ulcer" and "Resurfaced Full-thickness Pressure Ulcer" is not selected on screen 513 shown in FIG. 18, no characteristics or symptoms in screen 518 of FIG. 19 are selected, and an Unstageable Pressure Ulcer characteristic or symptom if selected on either screen 513 shown in FIG. 18 (e.g., "Unstageable Pressure Ulcer") or on screen 522 of FIG. 20 is selected, then, in one embodiment, the PUD tool 112 will classify this as an Unstageable Pressure Ulcer, regardless of any other subsequent selections, and optionally the date this wound was first classified as an Unstageable Pressure Ulcer will be stored on all future assessments beside the characteristic "Unstageable Pressure Ulcer" on screen 513 shown in FIG. 18.

Figure 21:
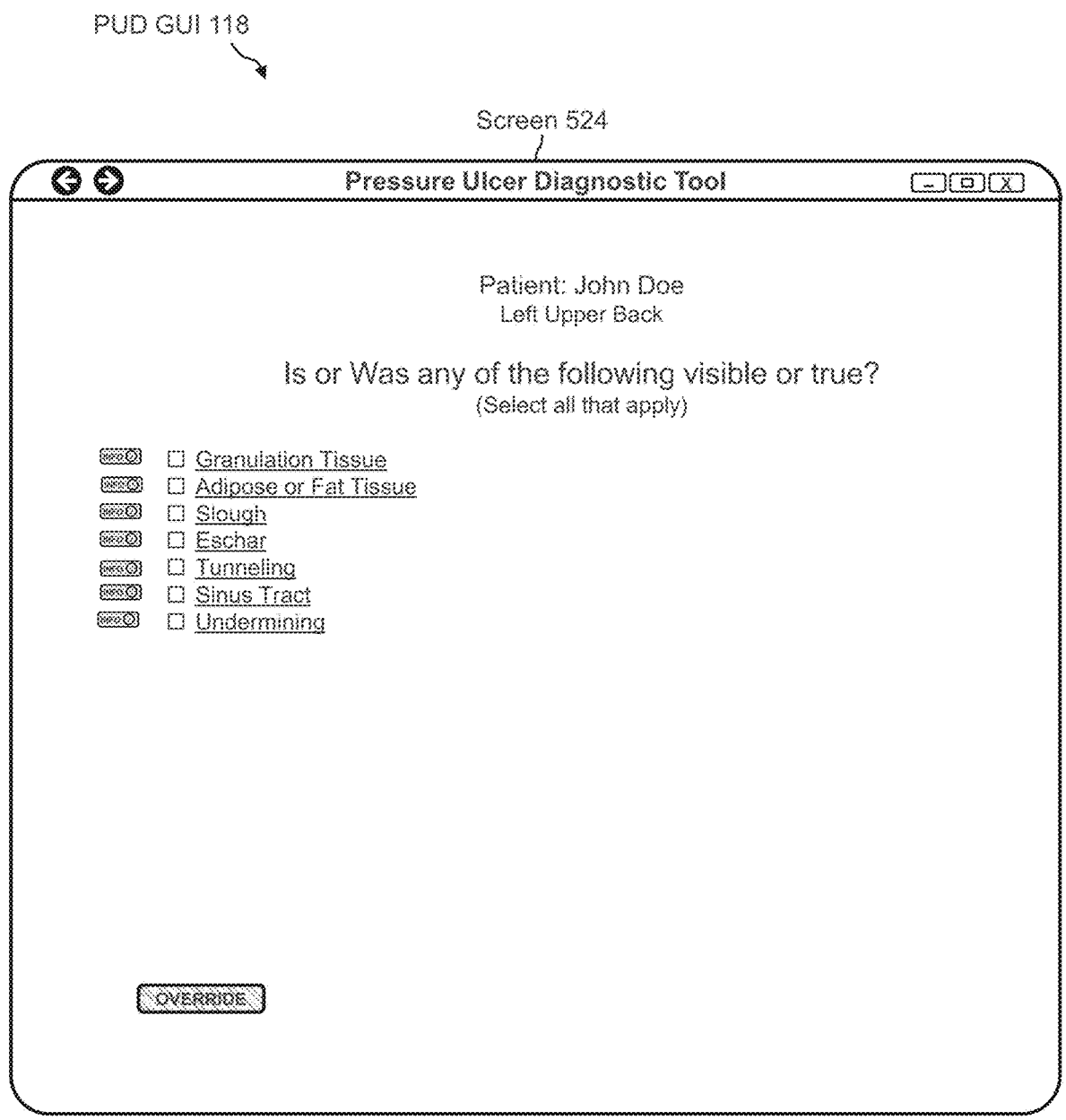
FIG. 21 is a screenshot of an alternative exemplary Stage 3 wound classification screen of a PUD system, according to one embodiment of the present disclosure.

FIG. 21 is a screenshot of an alternative exemplary Stage 3 wound classification screen of a PUD system, according to one embodiment of the present disclosure. FIG. 21 shows screen 524 previously shown in FIG. 12, as described in step 442 of the method 400. In this example, statements in FIG. 12 (e.g., "This wound was previously classified as an Unstageable Pressure Ulcer" and "This wound was previously classified as a Stage 3 Pressure Ulcer") is omitted. If a pressure ulcer was not previously classified as a Stage 4 Pressure Ulcer or a Resurfaced Full-thickness Pressure Ulcer, "Stage 4 Pressure Ulcer" and/or "Resurfaced Full-thickness Pressure Ulcer" is not selected on screen 513 shown in FIG. 18, no characteristic or symptom in screen 518 of FIG. 19 and screen 522 of FIG. 20 is selected, and at least one characteristic or symptom on screen 524 of FIG. 21 is selected, then, in one embodiment, the PUD tool 112 will classify this particular pressure ulcer as a Stage 3 Pressure Ulcer regardless of any other subsequent selections, and optionally the date this wound was first classified as an Stage 3 Pressure Ulcer will be stored on all future assessments beside the characteristic "Stage 3 Pressure Ulcer" on screen 513 shown in FIG. 18.

Figure 22:
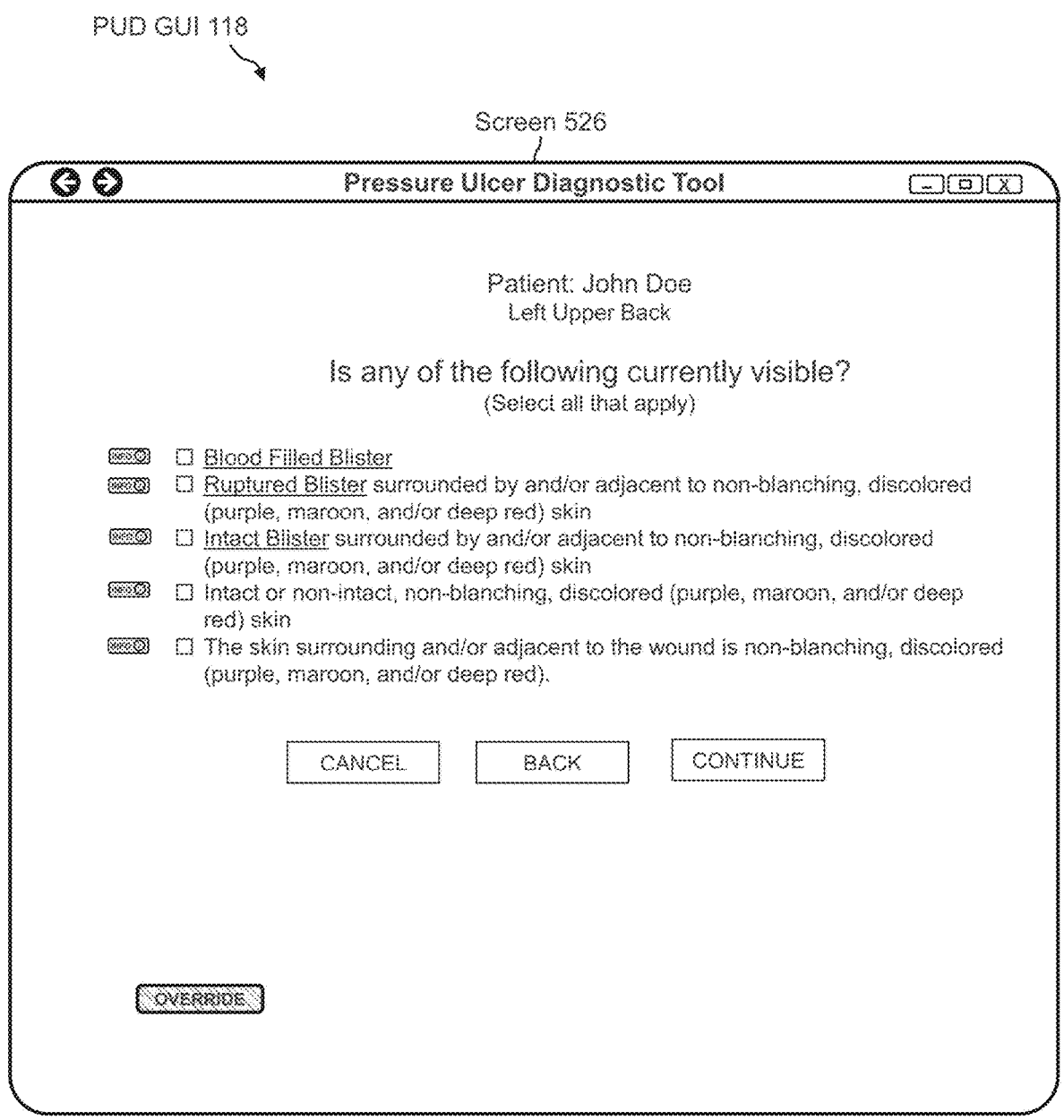
FIG. 22 is a screenshot of an alternative exemplary DTI wound classification screen of a PUD system, according to one embodiment of the present disclosure.

FIG. 22 is a screenshot of an alternative exemplary DTI wound classification screen of a PUD system, according to one embodiment of the present disclosure. FIG. 22 shows screen 526, as previously shown in FIG. 13 and as described in step 450 of the method 400. If on screen 513 shown in FIG. 18, Stage 1 Pressure Ulcer, Stage 2 Pressure Ulcer, Deep Tissue Injury, and/or Not previously classified or Unknown are selected, then the method 400 will continue as previously described in the method 400 as described in FIG. 4. FIG. 22 also shows screen 526 as previously shown in FIG. 13 and described in step 450 of the method 400). If a pressure ulcer was not previously classified as a Stage 4 Pressure Ulcer, a Resurfaced Full-thickness Pressure Ulcer, an Unstageable Pressure Ulcer, or a Stage 3 Pressure Ulcer, "Stage 4 Pressure Ulcer", "Resurfaced Full-thickness Pressure Ulcer", "Unstageable Pressure Ulcer", and "Stage 3 Pressure Ulcer" is not selected on screen 513 shown in FIG. 18, no characteristic or symptom in screen 518 shown in FIG. 19, screen 522 shown in FIG. 20, and screen 524 shown in FIG. 21 is selected, and at least one characteristic or symptom on screen 526 of FIG. 22 is selected, then, in one embodiment, the PUD tool 112 will classify this as a Deep Tissue Injury regardless of any other subsequent selections and optionally the date this wound was first classified as an Deep Tissue Injury will be stored on all future assessments beside the characteristic "Deep Tissue Injury" on screen 513 shown in FIG. 18.

Figure 23:
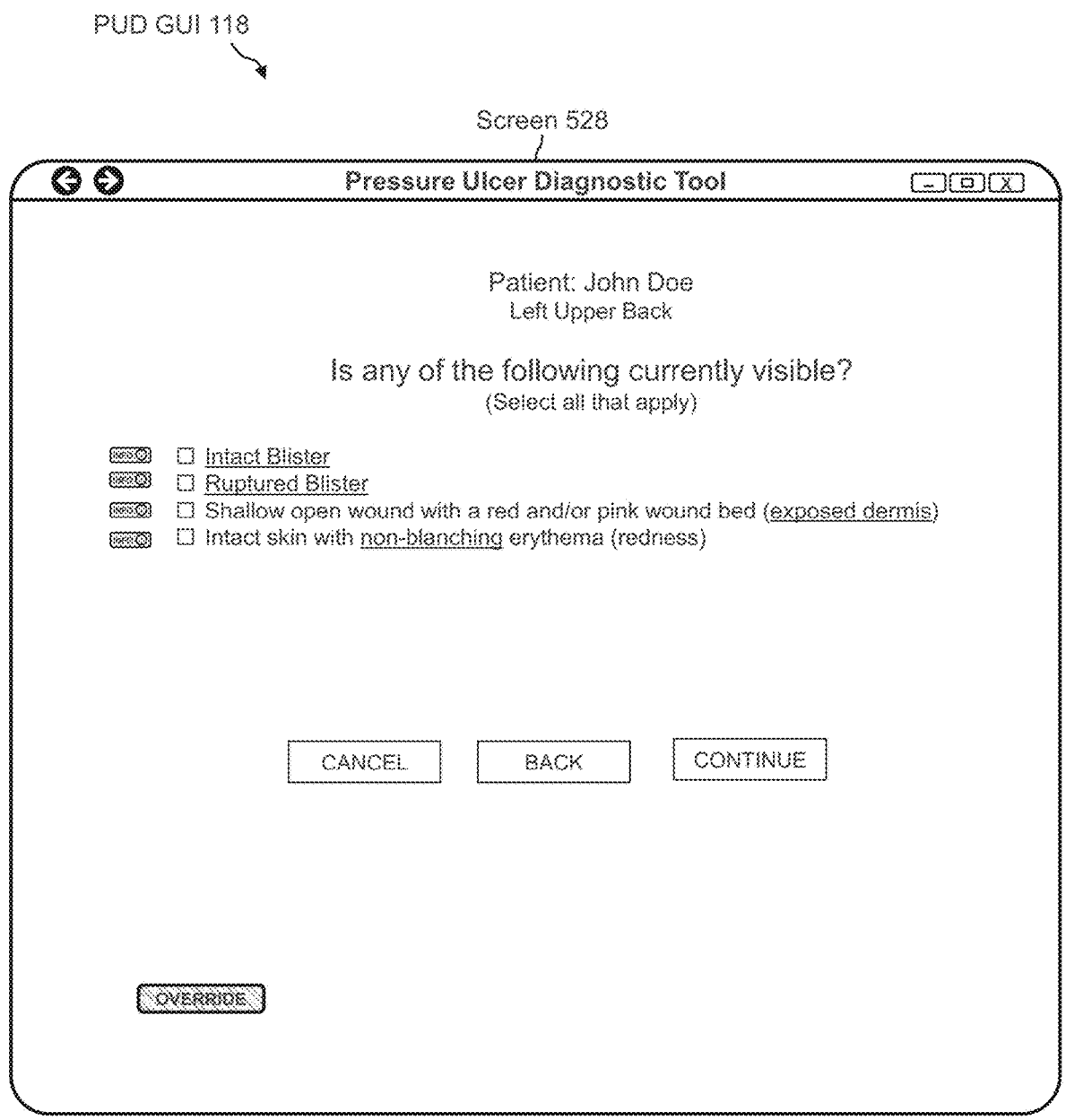
FIG. 23 is a screenshot of an alternative exemplary Stage 2/Stage 1 wound classification screen of a PUD system, according to one embodiment of the present disclosure.

FIG. 23 is a screenshot of an alternative exemplary Stage 2/Stage 1 wound classification screen of a PUD system, according to one embodiment of the present disclosure. FIG. 23 shows screen 528 as previously shown in FIG. 14 and described in step 458 of the method 400). If a pressure ulcer was not previously classified as a Stage 4 Pressure Ulcer, a Resurfaced Full-thickness Pressure Ulcer, an Unstageable Pressure Ulcer, or a Stage 3 Pressure Ulcer, "Stage 4 Pressure Ulcer", "Resurfaced Full-thickness Pressure Ulcer", "Unstageable Pressure Ulcer", and "Stage 3 Pressure Ulcer", is not selected on screen 513 shown in FIG. 18, no characteristic or symptom in screen 518 shown in FIG. 19, screen 522 shown in FIG. 20, screen 524 shown in FIG. 21, and screen 526 shown in FIG. 22 is selected, and at least one characteristic or symptom of a Stage 2 Pressure Ulcer is selected on screen 528 of FIG. 23 is selected (e.g., "Intact blister", "Ruptured blister", and/or "Shallow open wound with a red and/or pink wound bed/exposed dermis"), then, in one embodiment, the PUD tool 112 will classify this as a Stage 2 Pressure Ulcer regardless of any other subsequent selections and optionally the date this wound was first classified as an Stage 2 Pressure Ulcer will be stored on all future assessments beside the characteristic "Stage 2 Pressure Ulcer" on screen 513 shown in FIG. 18.

FIG. 23 also shows screen 528 as previously shown in FIG. 14 and described in step 466 of the method 400). If a pressure ulcer was not previously classified as a Stage 4 Pressure Ulcer, a Resurfaced Full-thickness Pressure Ulcer, an Unstageable Pressure Ulcer, or a Stage 3 Pressure Ulcer, "Stage 4 Pressure Ulcer", "Resurfaced Full-thickness Pressure Ulcer", "Unstageable Pressure Ulcer", and "Stage 3 Pressure Ulcer", is not selected on screen 513 shown in FIG. 18, and no characteristic or symptom in screen 518 shown in FIG. 19, screen 522 shown in FIG. 20, screen 524 shown in FIG. 21, and screen 526 shown in FIG. 22 is selected, no Stage 2 characteristic or symptom is selected on screen 528 of FIG. 23 is selected (e.g., "Intact blister", "Ruptured blister", and/or "Shallow open wound with a red and/or pink wound bed/exposed dermis"), and at least one or more characteristic or symptom of a Stage 1 Pressure Ulcer are present on screen 528 shown in FIG. 23 (e.g., "Intact skin with non-blanching erythema/redness"), then the PUD tool 112 will classify this as a Stage 1 Pressure Ulcer regardless of any other subsequent selections and optionally the date this wound was first classified as an Stage 1 Pressure Ulcer will be stored on all future assessments beside the characteristic "Stage 1 Pressure Ulcer" on screen 513 shown in FIG. 18.

FIG. 23 also shows screen 528 as previously shown in FIG. 14 and described in step 466 of the method 400). If a pressure ulcer was not previously classified as a Stage 4 Pressure Ulcer, a Resurfaced Full-thickness Pressure Ulcer, an Unstageable Pressure Ulcer, or a Stage 3 Pressure Ulcer, "Stage 4 Pressure Ulcer", "Resurfaced Full-thickness Pressure Ulcer", "Unstageable Pressure Ulcer", or a "Stage 3 Pressure Ulcer", is not selected on screen 513 shown in FIG. 18, no characteristic or symptom in screen 518 shown in FIG. 19, screen 522 shown in FIG. 20, screen 524 shown in FIG. 21, and screen 526 shown in FIG. 22 is selected, and 528 of FIG. 23, then, in one embodiment, the PUD tool 112 will classify this as a "Not a Pressure Ulcer."

FIG. 24 shows data demonstrating that the presently disclosed PUD system and tool are capable of diagnosing pressure injuries with 100% accuracy in contrast to conventional methods which are not even half as accurate. In yet another aspect of the presently disclosed PUD system, PUD tool, and methods, when used properly, it may achieve 100% accuracy of diagnosing/classifying pressure ulcers as compared with conventional methods that are only from about 30% to about 64% accurate. Generally, seventeen (17) different healthcare practitioners (e.g., registered nurses/ "RN" and licensed practical nurses/"LPN") of various demographics (disclosed in FIG. 24) were tested on classification of pressure ulcers both using the currently disclosed system and without using the currently disclosed system. The tests showed that these healthcare practitioners (with at least 3 years of experience and up to 38 years of experience and other experience as explained in FIG. 24) were only able to accurately classify a pressure ulcer 20-70% of time without using the currently disclosed system. Generally, without using the system, these healthcare practitioners frequently staged the pressure ulcer too low (e.g., Stage 3 instead of Stage 4) or staged the pressure ulcer too high (e.g., Stage 2 instead of Stage 1). In contrast, when using the presently disclosed system, these healthcare practitioners were accurate 100% of the time when classifying pressure ulcers.

Alternative Embodiments

A pressure ulcer diagnostic (PUD) clinical decision support system, computer application, and methods is disclosed. In one embodiment, the PUD clinical decision support system is in a standalone configuration that comprises a user computer that further comprises a PUD tool (e.g., a computer application), a data store, and a communications interface. In another embodiment, the PUD system is in a networked configuration that comprises the PUD tool running on an application server and a plurality of user computers that are connected to the application server via a network. In the networked PUD system, the application server may support a cloud computing environment. A method of using the PUD system for accurately diagnosing pressure ulcers is provided. Further, a method of diagnosing pressure ulcers using the PUD tool of the PUD system is provided.

An aspect of the presently disclosed subject matter provides a method of diagnosing a subject's pressure ulcer, the method comprising: a) optionally removing a dressing, if present, covering a wound bed and periwound area of the subject's pressure ulcer; b) optionally cleaning the wound bed and periwound area of the subject's pressure ulcer; c) determining whether the subject's pressure ulcer was either i) not previously classified or unknown; or ii) previously diagnosed as a pressure ulcer selected from the group consisting of: 1) a Stage 4 Pressure Ulcer, 2) a Resurfaced Full-thickness Pressure Ulcer, 3) an Unstageable Pressure Ulcer, 4) a Stage 3 Pressure Ulcer, 5) a Deep Tissue Injury, 6) a Stage 2 Pressure Ulcer, 7) a Stage 1 Pressure Ulcer and 8) Not a pressure ulcer; d) physically palpating the wound bed and periwound area of the subject's pressure ulcer; e) determining whether one or more pressure ulcer characteristic or symptom is and/or was visible, palpable and/or true, in the wound bed and periwound area of the subject's pressure ulcer, wherein one or more of the following characteristics or symptoms are selected from the group consisting of: i) a Stage 4 Pressure Ulcer characteristic or symptom (which comprises "bone", "muscle", "tendon", "ligament", "fascia", "cartilage", "joint capsule", "other supporting structures", and "This wound was previously classified as a Stage 4 Pressure Ulcer"), ii) a Resurfaced Full-Thickness Pressure Ulcer characteristic or symptom (which comprises "This pressure ulcer is or was closed, is or was 100% resurfaced with scar tissue and/or epithelium, and the last known stage was unknown or Unstageable"), iii) an Unstageable Pressure Ulcer characteristic or symptom (which comprises "Slough and/or eschar is obscuring/covering an area of the wound bed so the extent of the tissue loss cannot be determined"), iv) a Stage 3 Pressure Ulcer characteristic or symptom (which comprises "Granulation tissue, Adipose or fat tissue", "Slough", "Eschar", "Tunneling", "Undermining", "Sinus Tract", "This wound was previously classified as an Unstageable Pressure Ulcer", and "This wound was previously classified as a Stage 3 Pressure Ulcer"), v) a Deep Tissue Injury characteristic or symptom which comprises ("Blood filled blister", "Ruptured blister surrounded by and/or adjacent to discolored {purple, maroon, and/or deep red} intact skin", "Intact blister surrounded by and/or adjacent to non-blanching discolored {purple, maroon, and/or deep red} intact skin", "Intact or non-intact non-blanching discolored {purple, maroon, and/or deep red} skin", and "The skin surrounding or adjacent to the wound is non-blanching and discolored {purple, maroon, and/or deep red}"), vi) a Stage 2 Pressure Ulcer characteristic or symptom (which comprises "Intact blister", "Ruptured Blister", and "Shallow open wound with a red and/or pink wound bed {exposed dermis}"), vii) a Stage 1 Pressure Ulcer characteristic or symptom (which comprises "Intact skin with non-blanching erythema"), viii) Characteristics or symptoms not indicative of a pressure ulcer (which comprise "Blanching erythema and/or blanching discoloration"); and
f) diagnosing the subject's pressure ulcer depending on whether the subject's pressure ulcer was either c) i) not previously classified or unknown, or c) ii) previously diagnosed as a pressure ulcer listed in c) ii) 1)-c) ii) 8) above, wherein:

i) if the subject's pressure ulcer was c) i) not previously classified or unknown, diagnosing the subject's pressure ulcer comprises diagnosing the subject's pressure ulcer as a pressure ulcer selected from the group consisting of pressure ulcer characteristics and symptoms as listed in items c) ii) 1)-c) ii) 8) inclusive (above), wherein the subject's pressure ulcer is diagnosed as a Stage 4 Pressure Ulcer if at least one Stage 4 Pressure Ulcer characteristic or symptom as listed in e) i) is or was visible, palpable, and/or true, regardless of whether one or more pressure ulcer characteristic or symptom listed in e) ii)-e) viii) is or was visible, palpable, and/or true; wherein the subject's pressure ulcer is diagnosed as a Resurfaced Full-thickness Pressure Ulcer if 1) no Stage 4 Pressure Ulcer characteristic or symptom as listed in e) i) is or was visible, palpable, and/or true, and 2) at least one Resurfaced Full-thickness Pressure Ulcer characteristic or symptom listed in e) ii) is visible, palpable, and/or true, regardless of whether one or more pressure ulcer characteristics or listed in e) iii)-e) viii) is or was visible, palpable, and/or true; wherein the subject's pressure ulcer is diagnosed as an Unstageable Pressure Ulcer if 1) no Stage 4 Pressure Ulcer characteristic or symptom listed in e) i) is or was visible, palpable, and/or true, and 2) no Resurfaced Full-thickness Pressure Ulcer pressure ulcer characteristic or symptom listed in e) ii) is visible, palpable, and/or true, and 3) at least one Unstageable Pressure Ulcer characteristic or symptom listed in e) iii) is visible, palpable, and/or true, regardless of whether one or more pressure ulcer characteristics or symptoms listed in e) iv) through e) viii), is or was visible, palpable, and/or true; wherein the subject's pressure ulcer is diagnosed as a Stage 3 Pressure Ulcer if 1) no Stage 4 Pressure Ulcer characteristic or symptom listed in e) i) is or was visible, palpable, and/or true, and 2) no Resurfaced Full-thickness Pressure Ulcer characteristic or symptom listed in e) ii) is visible, palpable, and/or true, and 3) no Unstageable Pressure Ulcer characteristic or symptom listed in e) iii) is visible, palpable, and/or true, and 4) at least one Stage 3 Pressure Ulcer characteristic or symptom listed in e) iv) is or was visible, palpable, and/or true, regardless of whether one or more pressure ulcer characteristics or symptoms listed in e) v) through e) viii), is or was visible, palpable, and/or true; wherein the subject's pressure ulcer is diagnosed as a Deep Tissue Injury if 1) no Stage 4 Pressure Ulcer characteristic or symptom listed in e) i) is or was visible, palpable, and/or true, and 2) no Resurfaced Full-thickness Pressure Ulcer pressure ulcer characteristic or symptom listed in e) ii) is visible, palpable, and/or true, and 3) no Unstageable Pressure Ulcer characteristic or symptom listed in e) iii) is visible, palpable, and/or true, and 4) no Stage 3 Pressure Ulcer characteristic or symptom listed in e) iv) is or was visible, palpable, and/or true, and 5) at least one Deep Tissue Injury characteristic or symptom listed in e) v) is visible, palpable, and/or true, regardless of whether one or more pressure ulcer characteristic or symptom listed in e) vi)-e) viii) is or was visible, palpable, and/or true; wherein the subject's pressure ulcer is diagnosed as a Stage 2 Pressure Ulcer if 1) no Stage 4 Pressure Ulcer characteristic or symptom listed in e) i) is or was visible, palpable, and/or true, and 2) no Resurfaced Full-thickness Pressure Ulcer pressure ulcer characteristic or symptom listed in e) ii) is visible, palpable, and/or true, and 3) no Unstageable Pressure Ulcer characteristic or symptom listed in e) iii) is visible, palpable, and/or true, and 4) no Stage 3 Pressure Ulcer characteristic or symptom listed in e) iv) is or was visible, palpable, and/or true, and 5) no Deep Tissue Injury characteristic or symptom listed in e) v) is visible, palpable, and/or true, and 6) at least one Stage 2 Pressure Ulcer characteristic or symptom listed in e) vi) is visible, palpable, and/or true, regardless of whether one or more pressure ulcer characteristic or symptom listed in e) vii)-e) viii) is or was visible, palpable, and/or true; wherein the subject's pressure ulcer is diagnosed as a Stage 1 Pressure Ulcer if 1) no Stage 4 Pressure Ulcer characteristic or symptom listed in e) i) is or was visible, palpable, and/or true, and 2) no Resurfaced Full-thickness Pressure Ulcer pressure ulcer characteristic or symptom listed in e) ii) is visible, palpable, and/or true, and 3) no Unstageable Pressure Ulcer characteristic or symptom listed in e) iii) is visible, palpable, and/or true, and 4) no Stage 3 Pressure Ulcer characteristic or symptom listed in e) iv) is or was visible, palpable, and/or true, and 5) no Deep Tissue Injury characteristic or symptom listed in e) v) is visible, palpable, and/or true, and 6) no Stage 2 Pressure Ulcer characteristic or symptom listed in e) vi) is visible, palpable, and/or true, and 7) at least one Stage 1 Pressure Ulcer characteristic or symptom listed in e) vii) is visible or palpable, regardless of whether one or more characteristic or symptom listed in e) viii) is or was visible, palpable, and/or true; wherein the subject's pressure ulcer is determined as "Not a pressure ulcer" if 1) no Stage 4 Pressure Ulcer characteristic or symptom listed in e) i) is or was visible, palpable, and/or true, and 2) no Resurfaced Full-thickness Pressure Ulcer pressure ulcer characteristic or symptom listed in e) ii) is visible, palpable, and/or true, and 3) no Unstageable Pressure Ulcer characteristic or symptom listed in e) iii) is visible, palpable, and/or true, and 4) no Stage 3 Pressure Ulcer characteristic or symptom listed in e) iv) is or was visible, palpable, and/or true, and 5) no Deep Tissue Injury characteristic or symptom listed in e) v) is visible, palpable, and/or true, and 6) no Stage 2 Pressure Ulcer characteristic or symptom listed in e) vi) is visible, palpable, and/or true, and 7) no Stage 1 Pressure Ulcer characteristic or symptom listed in e) vii) is visible, palpable, and/or true;

ii) if the subject's pressure ulcer was previously diagnosed as a Stage 4 Pressure Ulcer using the PUD system 100, then diagnosing the subject's pressure ulcer comprises of diagnosing the pressure ulcer as a Stage 4 Pressure Ulcer, as the PUD system 100 will automatically pre-select the Stage 4 Pressure Ulcer characteristic under e) i) which states, "This pressure ulcer was previously classified as a Stage 4 Pressure Ulcer." Therefore, the PUD system 100 will classify this pressure ulcer as a Stage 4 Pressure Ulcer", regardless of whether any one or more pressure ulcer characteristic or symptom listed in items e) i) (other than the characteristic above) through e) viii) is or was visible, palpable, and/or true, thereby preventing diagnosis of the subject's pressure ulcer to any pressure ulcer classification other than a Stage 4 Pressure Ulcer which prevents reverse staging;

iii) if the subject's pressure ulcer was previously diagnosed as a Stage 4 Pressure Ulcer, but the PUD system 100 has not been used, then diagnosing the subject's pressure ulcer comprises of diagnosing the pressure ulcer as a Stage 4 Pressure Ulcer, if the user selects the characteristic in e) i) which states, "This pressure ulcer was previously classified as a Stage 4 Pressure Ulcer", regardless of whether any one or more pressure ulcer characteristic or symptom listed in items e) i)-e) viii) is or was visible, palpable, and/or true, thereby preventing diagnosis of the subject's pressure ulcer to any pressure ulcer classification other than a Stage 4 Pressure Ulcer which prevents reverse staging;

iv) if the subject's pressure ulcer was previously diagnosed as a Resurfaced Full-thickness Pressure Ulcer using the PUD system 100, then diagnosing the subject's pressure ulcer comprises of diagnosing the subject's pressure ulcer as a Resurfaced Full-thickness Pressure Ulcer if 1) no Stage 4 Pressure Ulcer characteristic or symptom listed in e) i) is or/was visible, palpable, and/or true, as the PUD system 100 will automatically pre-select the characteristic under e) ii) which states, "This pressure ulcer is or was closed, is or was resurfaced with 100% scar tissue and/or epithelium, and the last known stage was Unstageable or Unknown." Therefore, the PUD system 100 will classify this pressure ulcer as a Resurfaced Full-thickness Pressure Ulcer, regardless of whether any one or more pressure ulcer characteristic or symptom listed in items e) ii)-e) viii) is or was visible, palpable, and/or true, thereby preventing reverse staging; wherein the subject's pressure ulcer was previously diagnosed as a Resurfaced Full-thickness Pressure Ulcer, using the PUD system 100, diagnosing the subject's pressure ulcer as a Stage 4 Pressure Ulcer comprises diagnosing the subject's pressure ulcer as a Stage 4 Pressure Ulcer if 1) at least one Stage 4 Pressure Ulcer characteristic or symptom is or was visible, palpable, and/or true, thereby preventing reverse staging.

v) if the subject's pressure ulcer was previously diagnosed as a Resurfaced Full-thickness Pressure Ulcer but the PUD system 100 has not been used, then diagnosing the subject's pressure ulcer comprises of diagnosing the subject's pressure ulcer as a Resurfaced Full-thickness Pressure Ulcer if the user selects the characteristic in e) ii) which states "This pressure ulcer is or was closed, is or was resurfaced with 100% scar tissue and/or epithelium, and the last known stage was Unstageable or Unknown," regardless of whether any one or more pressure ulcer characteristic or symptom listed in items e) ii)-e) viii) is or was visible, palpable, and/or true, thereby preventing reverse staging; wherein the subject's pressure ulcer was previously diagnosed as a Resurfaced Full-thickness Pressure Ulcer, but the PUD system 100 has not been used, diagnosing the subject's pressure ulcer as a Stage 4 Pressure Ulcer comprises diagnosing the subject's pressure ulcer as a Stage 4 Pressure Ulcer if 1) at least one Stage 4 Pressure Ulcer characteristic or symptom as listed in e) i) is or was visible, palpable, and/or true, regardless of whether any one or more pressure ulcer characteristic or symptom listed in items e) ii)-e) viii) is or was visible, palpable, and/or true, thereby preventing reverse staging;

vi) if the subject's pressure ulcer was previously diagnosed as an Unstageable Pressure Ulcer, then diagnosing the subject's pressure ulcer comprises diagnosing the subject's pressure ulcer as either a Stage 4 Pressure Ulcer, a Resurfaced Full Thickness Pressure Ulcer, an Unstageable Pressure Ulcer, or as a Stage 3 Pressure Ulcer, depending on the characteristics or symptoms present, without allowing the pressure ulcer to be diagnosed as a Deep Tissue Injury, a Stage 2 Pressure Ulcer, a Stage 1 Pressure Ulcer, or as Not a Pressure Ulcer, regardless of the characteristics and symptoms present, thereby preventing reverse staging; wherein if the subject's pressure ulcer was previously diagnosed as an Unstageable Pressure Ulcer using the PUD system 100, then the subject's pressure ulcer will be diagnosed as a Stage 4 Pressure Ulcer if at least one Stage 4 Pressure Ulcer characteristic or symptom listed in e) i) is or was visible, palpable, and/or true, regardless of whether one or more of the characteristics or symptoms listed in e) ii) through e) viii) is or was visible, palpable, and/or true, thereby preventing reverse staging; wherein if the subjects pressure ulcer was previously diagnosed as an Unstageable Pressure Ulcer Pressure Ulcer using the PUD system 100, the subject's pressure ulcer will be diagnosed as a Resurfaced Full-thickness Pressure Ulcer, if 1) no Stage 4 Pressure Ulcer characteristic or symptom listed in e) i) is or was visible, palpable, and/or true, and 2) at least one Resurfaced Full-thickness Pressure Ulcer characteristic or symptom listed in e) ii) is visible, palpable, and/or true, regardless of whether one or more of the characteristics or symptoms listed in e) iii) through e) viii) is or was visible, palpable, and/or true, thereby preventing reverse staging; wherein if the subjects pressure ulcer was previously diagnosed as an Unstageable Pressure Ulcer, the subject's pressure ulcer will remain diagnosed as an Unstageable Pressure Ulcer if 1) no Stage 4 Pressure Ulcer characteristics or symptoms listed in e) i) is or was visible, palpable, and/or true, and 2) no Resurfaced Full-thickness Pressure Ulcer characteristic or symptom listed in e) ii) is or was visible, palpable, and/or true, if the user selects the characteristic in e) iv) which states, "This wound was previously classified as an Unstageable Pressure Ulcer", regardless of whether one or more of the characteristics or symptoms listed in e) iv) through e) viii) is or was visible, palpable, and/or true, thereby preventing reverse staging; wherein if the subjects pressure ulcer was previously diagnosed as an Unstageable Pressure Ulcer using the PUD system 100, the subject's pressure ulcer will be diagnosed as a Stage 3 Pressure Ulcer if 1) no Stage 4 Pressure Ulcer characteristics or symptoms listed in e) i) is or was visible, palpable, and/or true, and 2) no Resurfaced Full-thickness Pressure Ulcer characteristic or symptom listed in e) ii) is visible, palpable, and/or true, and 3) no Unstageable Pressure Ulcer characteristic or symptom listed in e) iii) is visible, palpable, and/or true, as the system will automatically pre-select the Stage 3 Pressure Ulcer characteristic under e) iv) which states "This pressure ulcer was previously classified as an Unstageable Pressure Ulcer." Therefore, the PUD system 100 will classify this pressure ulcer as a Stage 3 Pressure Ulcer, regardless of whether one or more of the characteristics or symptoms listed in e) iv) through e) viii) is or was visible, palpable, and/or true, thereby preventing reverse staging. Additionally, on all subsequent assessments, the system will automatically pre-select the characteristic in e) iv) which states "This was previously classified as a Stage 3 Pressure Ulcer" to prevent reverse staging of an Unstageable Pressure Ulcer, by not allowing a diagnosis of a Deep Tissue Injury, a Stage 2 Pressure Ulcer, a Stage 1 Pressure Ulcer, or as Not a Pressure Ulcer.

vii) if the subject's pressure ulcer was previously diagnosed as an Unstageable Pressure Ulcer, but the PUD system 100 has not been used, then the subject's pressure ulcer comprises diagnosing the pressure ulcer as a Stage 4 Pressure Ulcer if at least one Stage 4 Pressure Ulcer characteristic or symptom listed in e) i) is or was visible, palpable, and/or true, regardless of whether one or more of the characteristics or symptoms listed in e) ii) through e) viii) is or was visible, palpable, and/or true, thereby preventing reverse staging; wherein if the subjects pressure ulcer was previously diagnosed as an Unstageable Pressure Ulcer Pressure Ulcer but the PUD system 100 has not been used, then the subject's pressure ulcer will be diagnosed as a Resurfaced Full-thickness Pressure Ulcer, if 1) no Stage 4 Pressure Ulcer characteristic or symptom listed in e) i) is or was visible, palpable, and/or true, and 2) at least one Resurfaced Full-thickness Pressure Ulcer characteristic or symptom listed in e) ii) is visible, palpable, and/or true, regardless of whether one or more of the characteristics or symptoms listed in e) iii) through e) viii) is or was visible, palpable, and/or true, thereby preventing reverse staging; wherein if the subjects pressure ulcer was previously diagnosed as an Unstageable Pressure Ulcer but the PUD system 100 has not been used, then the subject's pressure ulcer will remain diagnosed as an Unstageable Pressure Ulcer if 1) no Stage 4 Pressure Ulcer characteristics or symptoms listed in e) i) is or was visible, palpable, and/or true, and 2) no Resurfaced Full-thickness Pressure Ulcer characteristic or symptom listed in e) ii) is or was visible, palpable, and/or true, and 3) the user selects the characteristic or symptom in e) iii) which states "Slough and/or eschar is obscuring/covering an area of the wound bed so the extent of the tissue loss cannot be determined," or any characteristic or symptom in e) iii), regardless of whether one or more of the characteristics or symptoms listed in e) iv) through e) viii) is or was visible, palpable, and/or true, thereby preventing reverse staging; wherein if the subjects pressure ulcer was previously diagnosed as an Unstageable Pressure Ulcer, but the PUD system 100 has not been used, the subject's pressure ulcer will be diagnosed as a Stage 3 Pressure Ulcer if 1) no Stage 4 Pressure Ulcer characteristics or symptoms listed in e) i) is or was visible, palpable, and/or true, and 2) no Resurfaced Full-thickness Pressure Ulcer characteristic or symptom listed in e) ii) is visible, palpable, and/or true, and 3) no Unstageable Pressure Ulcer characteristic or symptom listed in e) iii) is visible, palpable, and/or true, if the user selects the characteristic in e) iv) which states "This pressure ulcer was previously classified as an Unstageable Pressure Ulcer." Therefore, the PUD system 100 will classify this pressure ulcer as a Stage 3 Pressure Ulcer, regardless of whether one or more of the characteristics or symptoms listed in e) iv) through e) viii) is or was visible, palpable, and/or true, thereby preventing reverse staging. Additionally, on all subsequent assessments, the system will automatically pre-select the characteristic in e) iv) which states "This was previously classified as a Stage 3 Pressure Ulcer" to prevent reverse staging of an Unstageable Pressure Ulcer, by not allowing a diagnosis of a Deep Tissue Injury, a Stage 2 Pressure Ulcer, a Stage 1 Pressure Ulcer, or as Not a Pressure Ulcer.

viii) if the subject's pressure ulcer was previously diagnosed as a Stage 3 Pressure Ulcer, diagnosing the subject's pressure ulcer comprises diagnosing the subject's pressure ulcer as either a Stage 4 Pressure Ulcer, a Resurfaced Full Thickness Pressure Ulcer, Unstageable Pressure Ulcer, or as a Stage 3 Pressure Ulcer, without allowing the pressure ulcer to be diagnosed as a Deep Tissue Injury, a Stage 2 Pressure Ulcer, a Stage 1 Pressure Ulcer, or as Not a Pressure Ulcer at this time, thereby preventing reverse staging; wherein if the subject's pressure ulcer was previously diagnosed as an Stage 3 Pressure Ulcer using the PUD system 100, the subject's pressure ulcer will be diagnosed as a Stage 4 Pressure Ulcer if 1) at least one Stage 4 Pressure Ulcer characteristic or symptom listed in e) i) is or was visible, palpable, and/or true, regardless of whether one or more of the characteristics or symptoms listed in e) ii) through e) viii) is or was visible, palpable, and/or true, thereby preventing reverse staging; wherein if the subjects pressure ulcer was previously diagnosed as an Stage 3 Pressure Ulcer using the PUD system 100, the subject's pressure ulcer will be diagnosed as a Resurfaced Full-thickness Pressure Ulcer on a subsequent assessment, if 1) no Stage 4 Pressure Ulcer characteristics or symptoms listed in e) i) is or was visible, palpable, and/or true, and 2) at least one Resurfaced Full-thickness Pressure Ulcer characteristic or symptom listed in e) ii) is visible, palpable, and/or true, regardless of whether one or more of the characteristics or symptoms listed in e) iii) through e) viii) is or was visible, palpable, and/or true, thereby preventing reverse staging; wherein if the subjects pressure ulcer was previously diagnosed as an Stage 3 Pressure Ulcer using the PUD system 100, the subject's pressure ulcer will be diagnosed as an Unstageable Pressure Ulcer if 1) no Stage 4 Pressure Ulcer characteristics or symptoms listed in e) i) is or was visible, palpable, and/or true, and 2) no Resurfaced full thickness pressure ulcer characteristic or symptom listed in e) ii) is visible, palpable, and/or true, and 3) at least one Unstageable Pressure Ulcer characteristic or symptom listed in e) iii) is visible, palpable, and/or true, regardless of whether one or more of the characteristics or symptoms listed in e) iv) through e) viii) is or was visible, palpable, and/or true, thereby preventing reverse staging; wherein if the subjects pressure ulcer was previously diagnosed as a Stage 3 Pressure Ulcer using the PUD system 100, the subject's pressure ulcer will remain diagnosed as a Stage 3 Pressure Ulcer if 1) no Stage 4 Pressure Ulcer characteristics or symptoms listed in e) i) is or was visible, palpable, and/or true, and 2) no Resurfaced full thickness pressure ulcer characteristic or symptom listed in e) ii) is visible, palpable, and/or true, and 3) no Unstageable Pressure Ulcer characteristic or symptom listed in e) iii) is visible, palpable, and/or true, as the PUD system 100 will automatically pre-select the stage 3 pressure ulcer characteristic in e) iv) which states, "This wound was previously classified as a Stage 3 Pressure Ulcer." Therefore, the system will classify this pressure ulcer as a Stage 3 Pressure Ulcer regardless of whether one or more of the characteristics or symptoms listed in e) iv) through e) viii) is or was visible, palpable, and/or true, thereby preventing reverse staging, by not allowing a diagnosis of a Deep Tissue Injury, a Stage 2 Pressure Ulcer, a Stage 1 Pressure Ulcer, or as Not a Pressure Ulcer.

iv) if the subject's pressure ulcer was previously diagnosed as a Stage 3 Pressure Ulcer not using the PUD system 100, the subject's pressure ulcer will be diagnosed as a Stage 4 Pressure Ulcer if 1) at least one Stage 4 Pressure Ulcer characteristic or symptom listed in e) i) is or was visible, palpable, and/or true, regardless of whether one or more of the characteristics or symptoms listed in e) ii) through e) viii) is or was visible, palpable, and/or true, thereby preventing reverse staging; wherein if the subjects pressure ulcer was previously diagnosed as an Stage 3 Pressure Ulcer not using the PUD system 100, then the subject's pressure ulcer will be diagnosed as a Resurfaced Full-thickness Pressure Ulcer, if 1) no Stage 4 Pressure Ulcer characteristics or symptoms listed in e) i) is or was visible, palpable, and/or true, and 2) at least one Resurfaced Full-thickness Pressure Ulcer characteristic or symptom listed in e) ii) is visible, palpable, and/or true, regardless of whether one or more of the characteristics or symptoms listed in e) iii) through e) viii) is or was visible, palpable, and/or true, thereby preventing reverse staging; wherein if the subjects pressure ulcer was previously diagnosed as an Stage 3 Pressure Ulcer not using the PUD system 100, then the subject's pressure ulcer will be diagnosed as an Unstageable Pressure Ulcer if 1) no Stage 4 Pressure Ulcer characteristics or symptoms listed in e) i) is or was visible, palpable, and/or true, and 2) no Resurfaced full thickness pressure ulcer characteristic or symptom listed in e) ii) is visible, palpable, and/or true, and 3) at least one Unstageable Pressure Ulcer characteristic or symptom listed in e) iii) is visible, palpable, and/or true, regardless of whether one or more of the characteristics or symptoms listed in e) iv) through e) viii) is or was visible, palpable, and/or true, thereby preventing reverse staging; wherein if the subjects pressure ulcer was previously diagnosed as a Stage 3 Pressure Ulcer not using the PUD system 100, then the subject's pressure ulcer will remain diagnosed as a Stage 3 Pressure Ulcer if 1) no Stage 4 Pressure Ulcer characteristics or symptoms listed in e) i) is or was visible, palpable, and/or true, and 2) no Resurfaced Full-thickness Pressure Ulcer characteristic or symptom listed in e) ii) is visible, palpable, and/or true, and 3) no Unstageable Pressure Ulcer characteristic or symptom listed in e) iii) is visible, palpable, and/or true, and the user selects the characteristic in e) iv) which states, "This wound was previously classified as a Stage 3 Pressure Ulcer," or any other characteristic or symptom in e) iv), thereby classifying this pressure ulcer as a Stage 3 Pressure Ulcer, regardless of whether one or more of the characteristics or symptoms listed in e) iv) through e) viii) is or was visible, palpable, and/or true, thereby preventing reverse staging, by not allowing a diagnosis of a Deep Tissue Injury, a Stage 2 Pressure Ulcer, a Stage 1 Pressure Ulcer, or as Not a Pressure Ulcer.

In particular embodiments, step f) further comprises: vi) The subject's pressure ulcer will be diagnosed as a Deep Tissue Injury, if 1) No pressure ulcer characteristics or symptoms listed in e) i)-e) iv) is or were visible, palpable, and/or true, and 2) there is at least one characteristic or symptom of a Deep Tissue Injury as listed in e) v) is visible, palpable, and/or true, regardless of whether one or more characteristic or symptoms listed in e) vi)-e) viii) is or was visible, palpable, and/or true, thereby ensuring a Deep Tissue Injury (DTI) is diagnosed over a Stage 1 Pressure Ulcer and/or a Stage 2 Pressure Ulcer even when a Stage 1 Pressure Ulcer or a Stage 2 Pressure Ulcer present alongside a DTI.

In particular embodiments, the Stage 4 Pressure Ulcer characteristics and symptoms is selected from a group consisting of: "bone", "muscle", "tendon", "ligament", "fascia", "cartilage", "joint capsule", "other supporting structures", "This wound was previously classified as a Stage 4 Pressure Ulcer", and combinations thereof.

In particular embodiments, the Resurfaced Full-thickness Pressure Ulcer characteristics and symptoms is selected from the group consisting of: "This pressure ulcer is or was closed, is or was resurfaced with scar tissue and/or epithelium, and the last known stage was unknown or Unstageable", and any combinations thereof.

In particular embodiments, the Unstageable Pressure Ulcer characteristics and symptoms is selected from the group consisting of: "Slough and/or eschar is obscuring/covering an area of the wound bed so the extent of the tissue loss cannot be determined", and any combinations thereof.

In particular embodiments, the Stage 3 Pressure Ulcer characteristics and symptoms is selected from the group consisting of: "Granulation tissue", "Adipose or fat tissue", "Slough", "Eschar", "Tunneling", "Undermining", "Sinus Tract", "This wound was previously classified as an Unstageable Pressure Ulcer", "This wound was previously classified as a Stage 3 Pressure Ulcer", and combinations thereof.

In particular embodiments, the Deep Tissue Injury characteristics and symptoms is selected from the group consisting of: "Blood filled blister", "Ruptured blister surrounded by and/or adjacent to discolored (purple, maroon, and/or deep red) intact skin", "Intact blister surrounded by and/or adjacent to non-blanching discolored (purple, maroon, and/or deep red) intact skin", "Intact and non-intact non-blanching discolored (purple, maroon, and/or deep red) skin", and "The skin surrounding or adjacent to the wound is non-blanching and discolored (purple, maroon, and/or deep red)" and combinations thereof.

In particular embodiments, the Stage 2 Pressure Ulcer characteristics and symptoms is selected from the group consisting of: "Intact blister", "Ruptured Blister", "Shallow open wound with a red and/or pink wound bed (exposed dermis)", and combinations thereof.

In particular embodiments, the Stage 1 Pressure Ulcer characteristic or symptom consists of: "Intact skin with non-blanching erythema", and combinations thereof.

In particular embodiments, not selecting any of the characteristics or symptoms listed in e) i through e) viii) would then establish that this wound is not a pressure ulcer.

In particular embodiments, cleaning the wound bed and periwound area of the subject's pressure ulcer comprises administering a cleaning solution to the wound bed and periwound area.

In particular embodiments, the method comprises treating the subject's pressure ulcer based on the diagnosis and international evidence based treatment guidelines.

In particular embodiments, wound care treatment is selected from the group consisting of: support surfaces, debridement (selected from a group of methods or agents consisting of enzymatic, chemical, biologic, sharp, and/or autolytic), or wound care dressings selected from the group consisting of hydrofibers, gelling fiber dressings, absorptive dressings, gauze, collagen based dressings, transparent film, hydrocolloids, hydrogel, foam, polymeric membrane dressings, cadexomer iodine dressings, silver impregnated dressings, antimicrobial dressings, calcium alginate dressings, honey containing dressings, glycerin dressings, impregnated dressings, grafts, surgery, antimicrobial creams/lotions, antifungal creams/lotions, antibiotics, gauze based dressings, grafts, Negative Pressure Wound Therapy, and combinations thereof.

In particular embodiments, the method is performed on a pressure ulcer diagnostic system comprising a computer that comprises a pressure ulcer diagnostic tool, a data store, and a communications interface.

In particular embodiments, the system further comprises an optional image capture device.

In particular embodiments, the computer is selected from the group consisting of a smartphone, a tablet, or a laptop, each optionally equipped with a digital camera.

In particular embodiments, the pressure ulcer diagnostic tool comprises a diagnosis module, a graphical user interface, an authentication module, and a security module.

In particular embodiments, the data store comprises application data, user data, patient data, and optionally image data.

In particular embodiments, the patient data is linked to a patient's electronic medical record via the communications interface.

In particular embodiments, the pressure ulcer diagnostic tool is a computer application.

In particular embodiments, the computer application is configured to cause the graphical user interface to display a screen for a user to input the results of determining step c), step d) and step e) into the pressure ulcer diagnostic system.

In particular embodiments, the computer application is configured to cause the graphical user interface to display a screen or multiple screens for a user to input the results of determining step c), step d) and step e) into the pressure ulcer diagnostic system. For example, the computer application may be configured to cause the graphical user interface to display a screen shown in FIG. 5 through FIG. 23, inclusive, or a similar screen that has the pertinent content though it may appear differently.

In particular embodiments, the computer application is configured to cause the graphical user interface to display one or more questions shown on a screen depicted in FIG. 5 through FIG. 23, inclusive.

In particular embodiments, the computer application is configured to cause the graphical user interface display screens that implement the computer implemented steps of method 300, including for example, steps 314, 316, 318, 320, 322 and 324.

In particular embodiments, the computer application is configured to cause the graphical user interface to display screens that implement the computer implemented steps of method 400, including for example, steps 410, 412, 414, 416, 418, 420, 422, 424, 425, 428, 430, 431, 432, 434, 436, 438, 439, 440, 442, 444, 446, 447, 448, 450, 452, 454, 455, 456, 458, 460, 462, 463, 464, 466, 468, 470, 471, 472, 474, 475, and 476.

In particular embodiments, the computer application is configured to cause the graphical user interface to display one or more pressure ulcer characteristics or symptoms in e) i)-e) viii) in the form of a hyperlink that when accessed causes the graphical user interface to display additional information regarding the one or more pressure ulcer characteristics or symptoms in e) i)-e) viii), wherein the additional information comprises definitions, drawings, images, and/or descriptions of the one or more characteristics, symptoms, or words and optionally comprises an exemplary image of the one or more characteristics, symptoms or words. A non-limiting example of this is shown FIG. 12C in pop up window 1205.

In particular embodiments, the computer application causes the results of determining step c), step d), step e), and step f) to be stored in the data store.

In particular embodiments, the computer application is configured to perform diagnosing step f) based on the results of determining step c), step d) and step e). It should be appreciated that such steps may be performed by diagnosis module 116, optionally in conjunction with the data store 114, communications interface 124, and PUD GUI 118.

Figure 5:
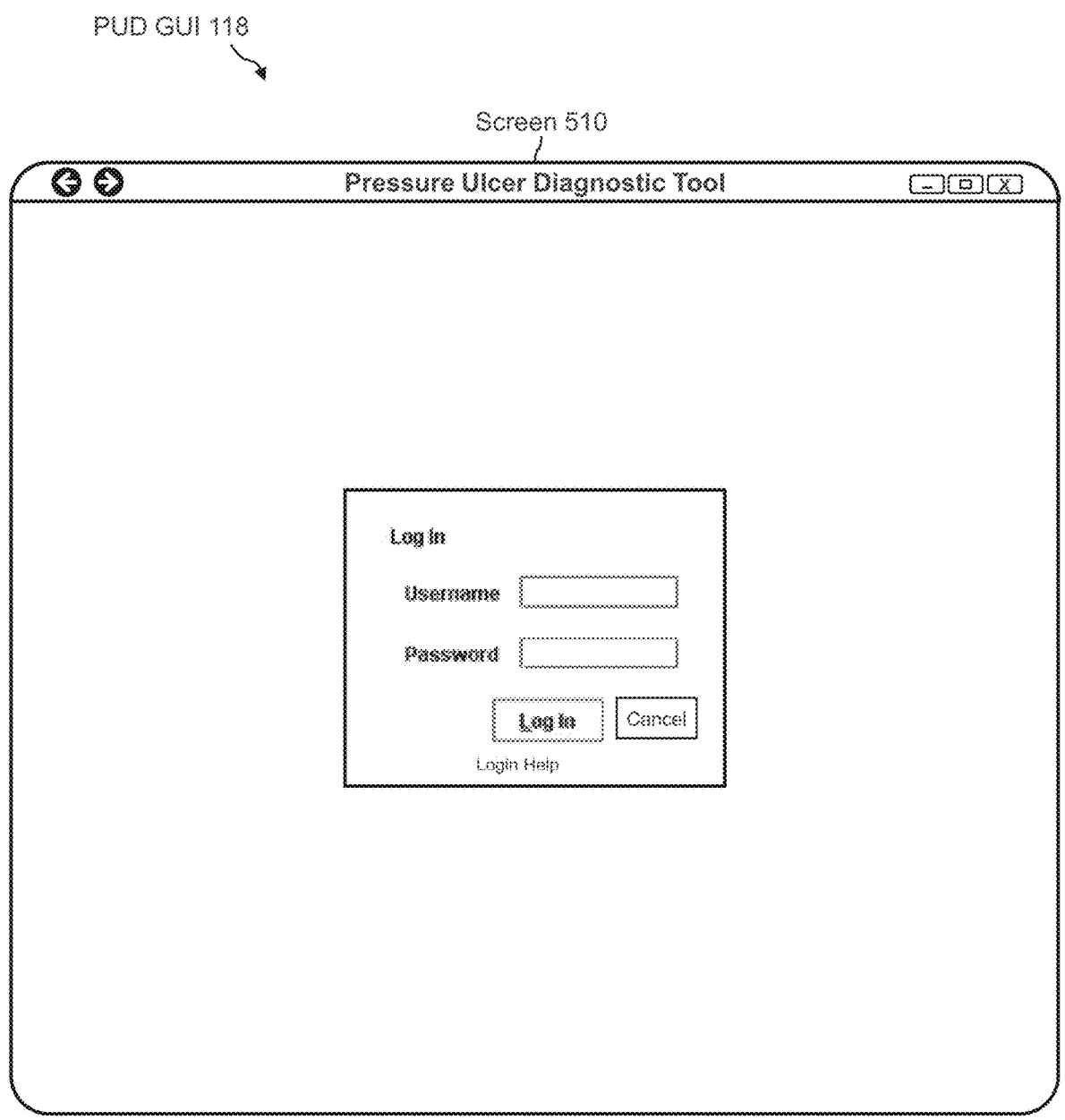
FIG. 5 is a screenshot of an exemplary login screen of a PUD system, according to one embodiment of the present disclosure.

In particular embodiments, the computer application is configured to cause the graphical user interface to display a user login and authentication screen. A non-limiting example of these embodiments is shown in FIG. 5.

In particular embodiments, the computer application is configured to cause the graphical user interface to display a screen that enables the user to select a patient whose pressure ulcer is to be diagnosed. A non-limiting example of these embodiments is shown in FIG. 6. Likewise, a new patient may also be entered in the system as shown in FIG. 6. In some instances, the graphical user interface 118 displays a screen 512 that comprises an option for the user to select an existing patient. For example, the user may select an existing patient by inputting a medical record number, date of birth, and/or the first and last name of the patient. Those skilled in the art will appreciate that the means by which the graphical user interface receives user input will depend on the computer or device used and the type of computer application or the device. In some instances, for example, on touch screen enabled devices, such as laptops, tablets and smartphones, or with voice dictation devices, the graphical user interface 118 may be activated via touch and the user may select a check box, or type in a form field directly on the screen 512. In such instances, a user may use a keyboard or keypad, stylus, or mouse to interact with the graphical user interface 118. In some instances, the graphical user interface 118 displays a screen 512 that comprises a button (or link) that enables a user to add a new patient, for example, if the patient of interest is not present in the data store (or networked electronic medical record). For example, the user may enter information regarding the patient's first and last name, medical record number, birthdate, ID number, barcode, date of birth, social security number, insurance policy information, and/or gender, and combinations thereof.

In particular embodiments, the method optionally further comprises capturing one or more digital photos or files of the wound bed and/or periwound area using the image capture device. In some embodiments, the computer application causes the graphical user interface 118 to display at screen 515 and screen 530 to show an icon that prompts a user to upload one or more digital photos of the wound bed and/or periwound area that were captured using the image capture device (or another device). One non-limiting example shown in FIG. 15A screen 530 which displays a box/icon where a photo may be uploaded. It is to be understood that the box/icon may be displayed on any screen where the user is prompted to enter any information (e.g., FIG. 7 through FIG. 23, inclusive).

In particular embodiments, the computer application is configured to cause one or more digital photos or files of the wound bed and/or periwound area captured using the image capture device to be stored in the image data of the data store.

In particular embodiments, the method comprises prior to, alternatively to, or in addition to determining the results of step c) and step d) and step e), the computer application causes the graphical user interface to display a screen that enables a user to select a new or pre-existing pressure ulcer and/or enter information about the cause of the pressure ulcer. A non-limiting example of such embodiments is shown in FIG. 7. In some instances, the graphical user interface 118 displays a screen 514 that comprises a drop-down menu listing previous diagnoses for a patient of interest. In some instances, the graphical user interface 118 displays a screen 514 that comprises a button or link that prompts a user to add a new pressure ulcer (e.g., one that has not been previously diagnosed for a particular patient using the PUD system).

Figure 9:
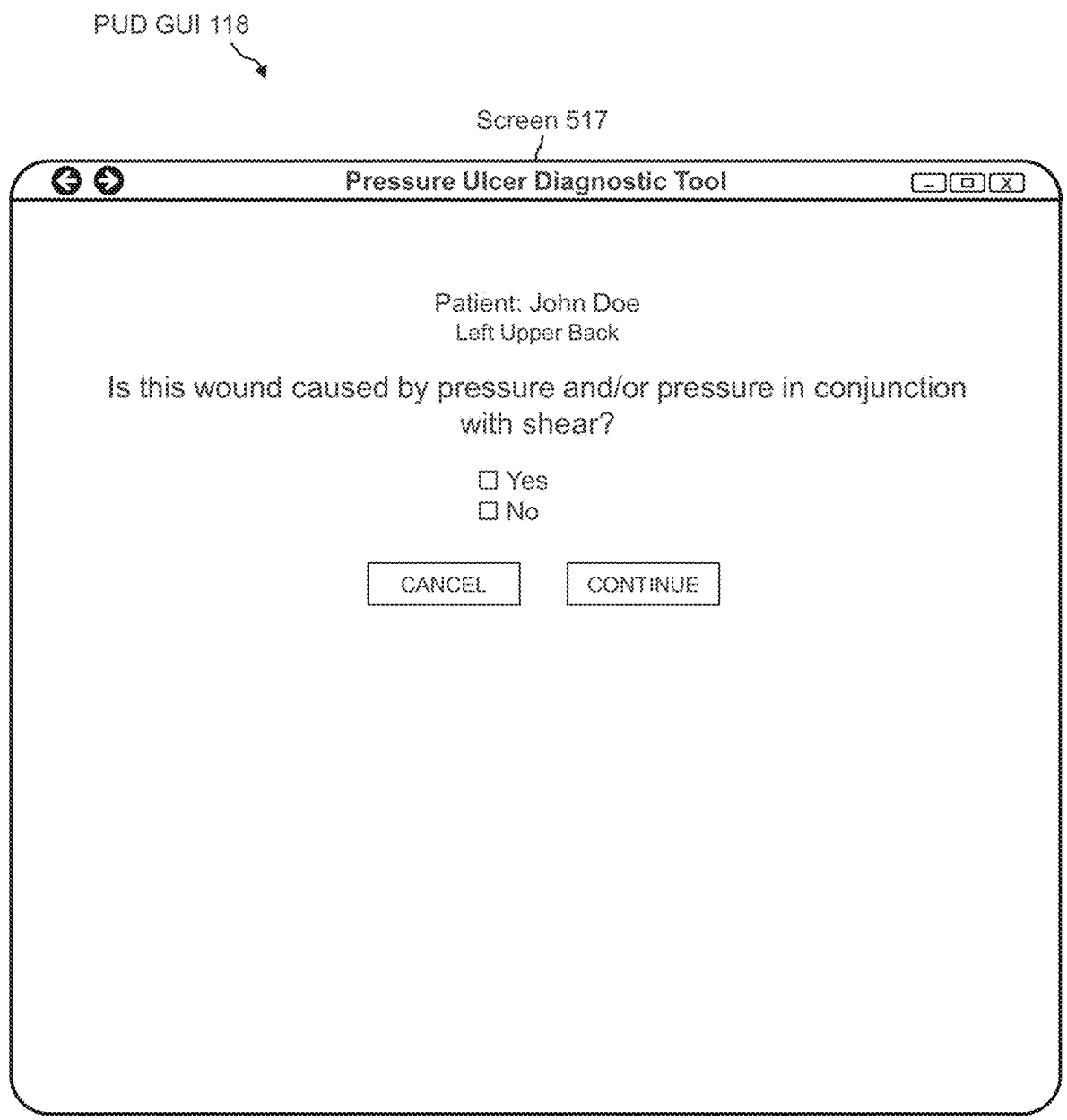
FIG. 9 is a screenshot of an exemplary initial wound classification screen of a PUD system, according to one embodiment of the present disclosure.
Figure 11:
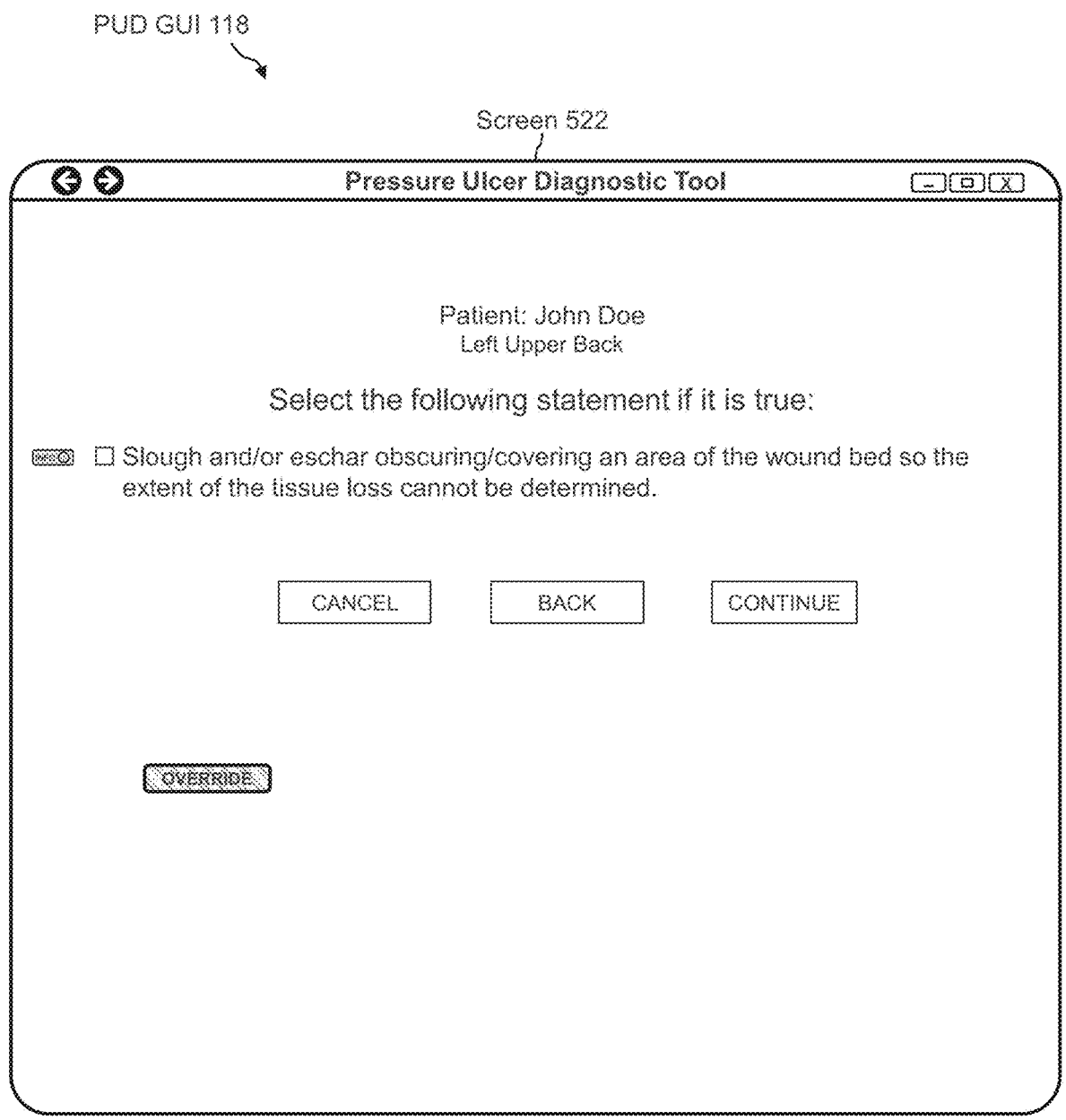
FIG. 11 is a screenshot of an exemplary unstageable wound classification screen of a PUD system, according to one embodiment of the present disclosure.

In particular embodiments, the graphical user interface 118 displays a screen 517 shown in FIG. 9, ensures that only wounds caused by pressure and/or pressure in combination with shear are classified and diagnosed with the PUD system. For example, the graphical user interface may display a question such as "Was this wound caused by pressure and/or pressure in combination with shear," as shown in FIG. 9, with check boxes for the user to check either "Yes" or "No." In other examples, a user may be prompted to select "Yes" or "No" in a drop-down menu, or via other means.

In particular embodiments, the method comprises prior to, alternatively to, or in addition to determining step c), the computer application causes the graphical user interface to display a screen that enables a user to enter a location of the wound bed. A non-limiting example is shown in FIG. 7 where a user may select the location of a wound by selecting the location on the body image in FIG. 7, that corresponds to the location of the wound on the subject/patient. In some instances, a user is prompted to select a pressure ulcer location, for example, using a drop-down menu (not shown). In other instances, a user is prompted to enter a pressure ulcer location. In particular embodiments, the method comprises after diagnosing step f), the computer application causes the graphical user interface to display a medical diagnosis code that is associated with the classification/diagnosis.

In particular embodiments, the method comprises after diagnosing step f), the computer application causes the user interface to display a "Wound Condition" associated with the pressure ulcer. Wound condition comprises the following options: open, closed, healed, or not applicable, and combinations thereof, with examples shown in FIG. 7, FIG. 8A, FIG. 8B, FIG. 15A, FIG. 15B, FIG. 16, and FIG. 17.

In particular embodiments, the method comprises after diagnosing step f), the computer application causes the user interface to display a "Wound Status" associated with the pressure ulcer. Wound status comprises the following options: Active, Inactive, Marked in error, and combinations thereof, with examples shown in FIG. 7, FIG. 8A, FIG. 8B, FIG. 15A, FIG. 15B, FIG. 16, and FIG. 17.

Figure 15B:
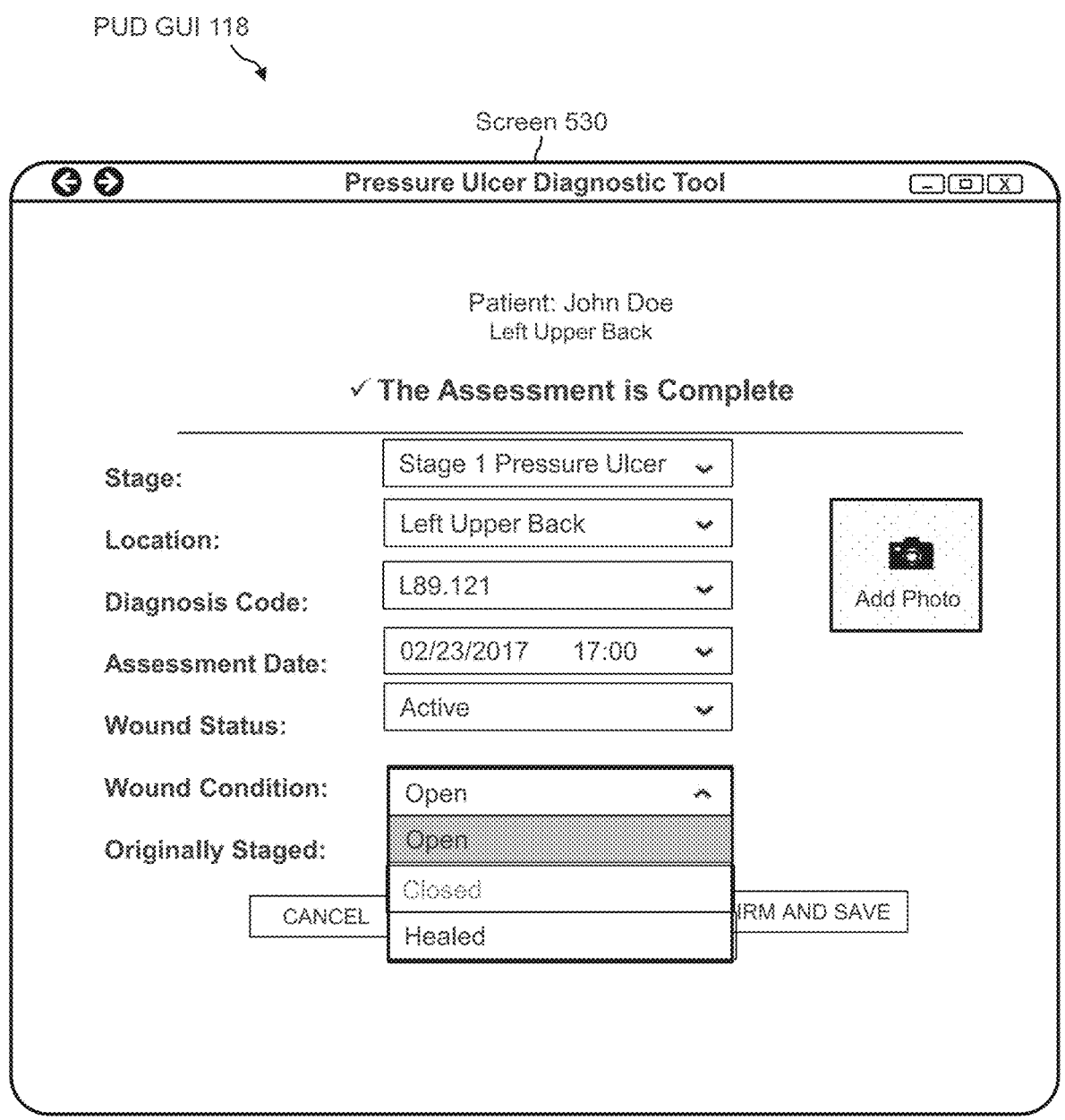
Figure 15C:
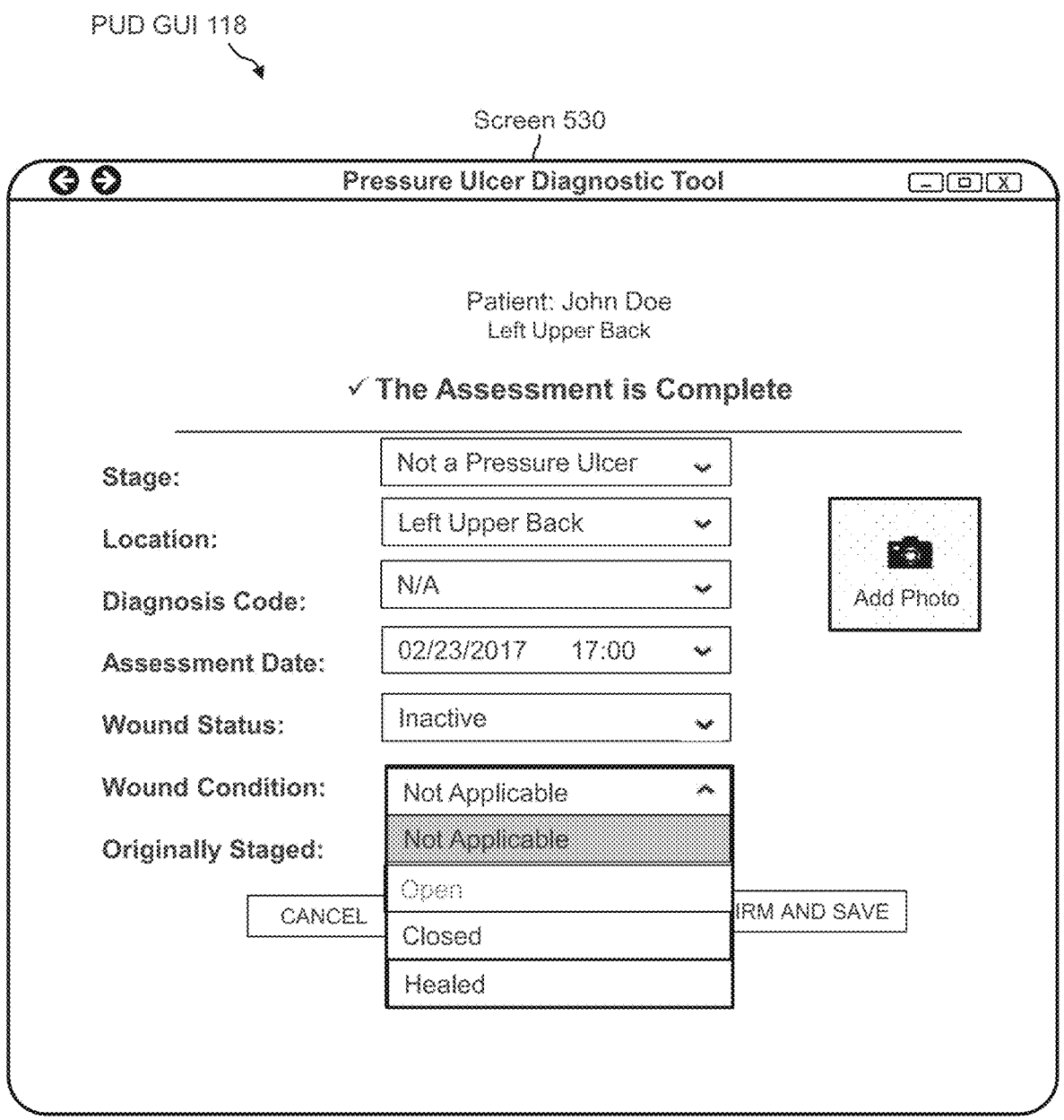
Figure 16:
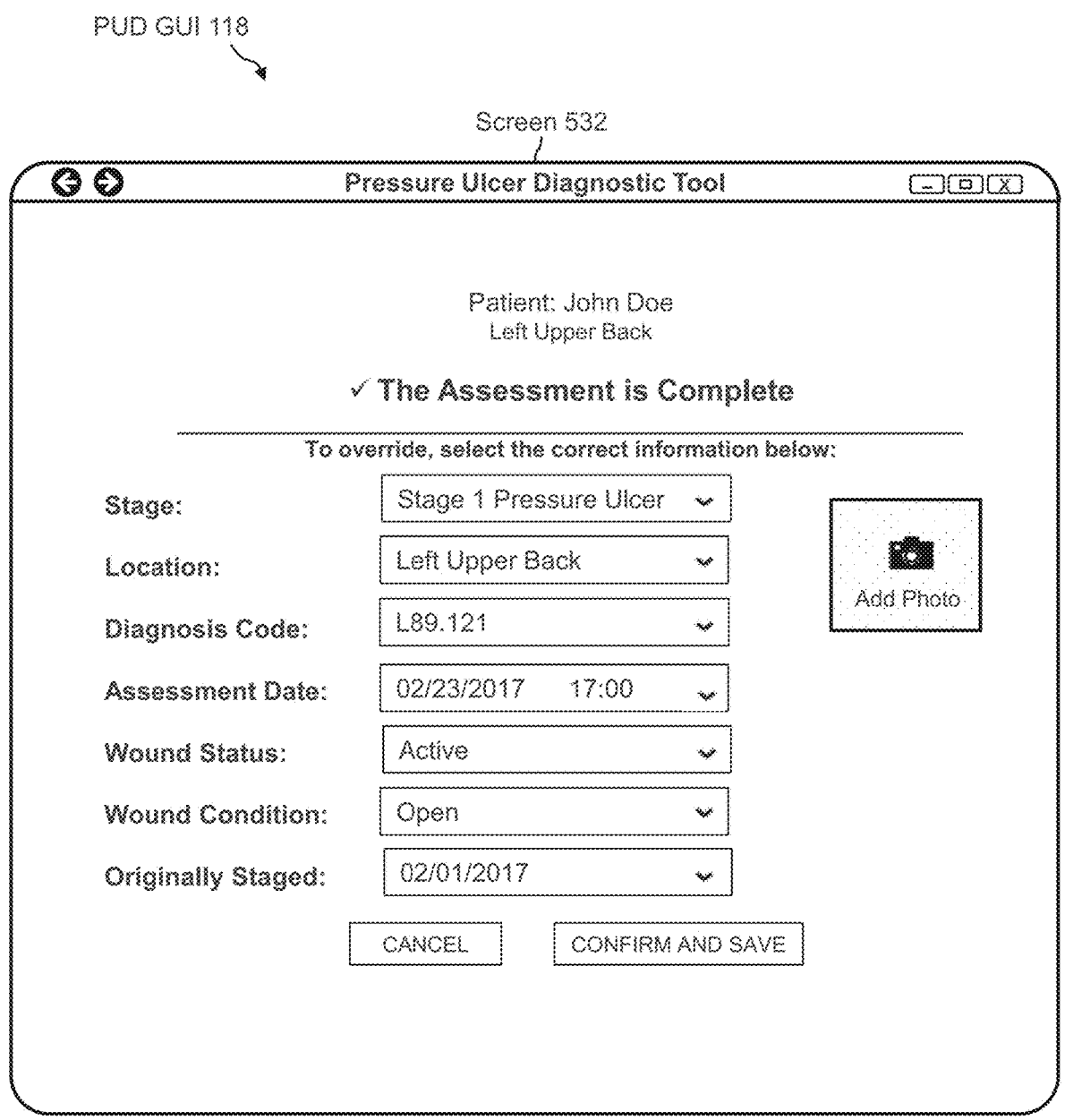
FIG. 16 is a screenshot of an exemplary wound classification override screen of a PUD system, according to one embodiment of the present disclosure.
Figure 17:
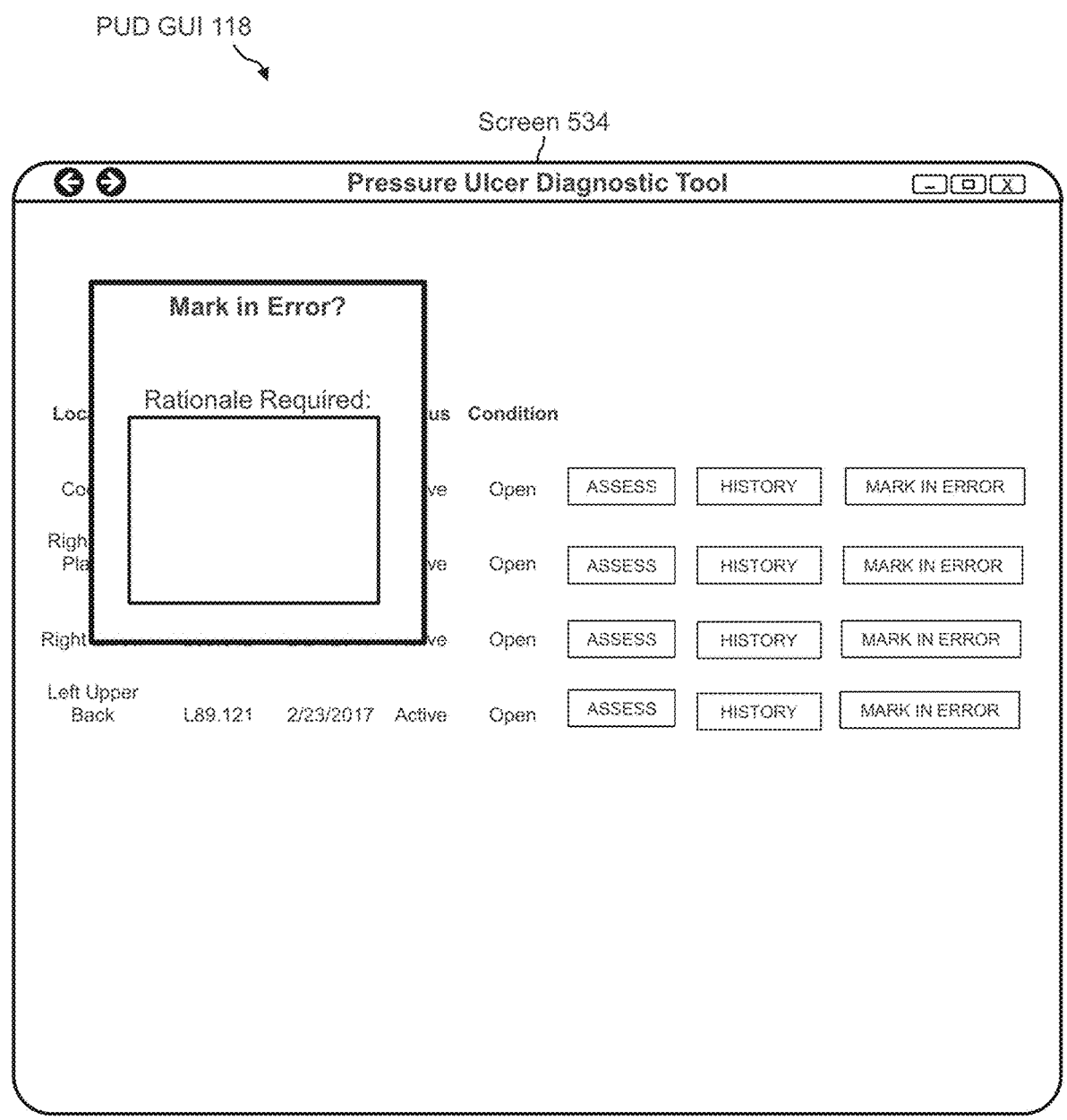
FIG. 17 is a screenshot of an exemplary override justification screen of a PUD system, according to one embodiment of the present disclosure.

In particular embodiments, the method comprises after diagnosing step f), the computer application causes the user interface to display the date the pressure ulcer or wound became the assigned medical diagnosis code initially beside the medical diagnosis code, as shown in, as shown in FIG. 15A, FIG. 15B, and FIG. 16. For example, if a pressure ulcer became a Stage 3 Pressure Ulcer on Mar. 1, 2016, the date Mar. 1, 2016 will be displayed beside the Stage 3 Pressure Ulcer diagnosis code as shown in FIG. 16.

In particular embodiments, the method comprises after diagnosing step f), the computer application causes the user interface to display the date and optionally the time of the current assessment being performed is completed, based on the date, time, and time zone the user accessed the computer application for the associated pressure ulcer in, as shown in, FIG. 16.

In particular embodiments, the method comprises after diagnosing step f), the computer application causes the graphical user interface to display a treatment recommendation that is associated with the diagnosis.

In particular embodiments, the method comprises after diagnosing step f), the computer application causes the graphical user interface to display a screen that enables a user to instruct the computer application on recording the diagnosis. A non-limiting example of this feature is shown in FIG. 15A.

In particular embodiments of the method, the computer application causes the graphical user interface to display a screen that shows the history or other information regarding the selected patient and previously diagnosed pressure ulcers/injuries. Non-limiting examples of such screens are shown in FIG. 7, FIG. 8A, FIG. 8B, AND FIG. 15A.

In particular embodiments, the computer application causes the graphical user interface to display an option for a user to indicate whether a pressure ulcer characteristic or symptom of a pressure ulcer is or was visible, palpable, and/or true. Non-limiting examples of this feature are shown in FIG. 10A, FIG. 10B, and FIG. 10C.

In particular embodiments, the computer application causes the graphical user interface to display a medical diagnosis code that is associated with the diagnosis, as shown in FIG. 15A. The user may also edit or enter their own established medical diagnosis code. For example, the computer application may cause graphical user interface 118 to display a drop-down menu that prompts a user to code and record a result in the patient's chart, as shown in FIG. 15B. In such instances, the drop-down menu may comprise the pressure ulcer classification (also known as stage, grade, and/or category), medical diagnosis code (which is a code used for payment and insurance purposes such as an ICD-10 code), location of the pressure ulcer, the wound condition, the wound status, the date the wound initially became the currently assigned classification (stage, grade, and/or category), and the date of the current assessment.

In particular embodiments, the method comprises after diagnosing step f), the computer application causes the diagnosis code, wound condition, wound status, wound location, date of current assessment, date of assessment in which this wound became the most current stage, Stage, and/or treatment recommendation to be stored in the patient data of the data store, and optionally transmits the diagnosis code and/or treatment recommendation to an electronic medical record of the patient via the communications interface.

In particular embodiments, the computer application causes the graphical user interface to display a wound condition, as shown in FIG. 15A. A wound condition explains the current healing state. For example, a wound condition may be open which means the wound is in an active open state and the wound is not healed; Alternatively, another wound condition wound be "healed" indicating the wound is closed and resurfaced with scar tissue and/or epithelium and is no longer present. In the PUD system, only Stage 1 Pressure Ulcers, Stage 2 Pressure Ulcers, and Deep Tissue Injuries may be classified as "healed." Classifying any other full-thickness pressure ulcer (such as a Stage 4 Pressure Ulcer, Resurfaced Full-thickness Pressure Ulcer, Unstageable Pressure Ulcer, and/or a Stage 3 Pressure) would be an example of reverse staging as those wounds do not heal, but only "close"; Thus another wound condition used only for the aforementioned full-thickness pressure ulcers would be "closed", meaning they have been resurfaced with 100% scar tissue and/or epithelium and they are closed (though by pressure ulcer classification rules, they remain present/active); Only those full-thickness pressure ulcers may be classified as "closed" whereas only Stage 1 and Stage 2 pressure ulcers and a DTI may be classified as healed; If a wound was entered into the PUD system by mistake, the user may select an option to "mark in error" as shown on screen 534 in FIG. 17. The wound condition will be automatically changed by the system to "marked in error" (and the wound status will be automatically changed to "Inactive"); If the wound is determined to be "not a pressure ulcer" the wound condition will be automatically selected by the system to be "not applicable" as this wound is not a pressure ulcer and the wound status will be "inactive." The user may also edit or enter their own established wound condition. For example, the computer application may cause graphical user interface 118 to display a drop-down menu that prompts a user to change the wound condition and record a result in the patient's chart, as shown in FIG. 15B. In such instances, the drop-down menu may comprise the pressure ulcer classification (also known as stage, grade, and/or category), medical diagnosis code (which is a code used for payment and insurance purposes such as an ICD-10 code), location of the pressure ulcer, the wound condition, the wound status, the date the wound initially became the currently assigned classification (stage, grade, and/or category), and the date of the current assessment. This helps prevent reverse staging.

In particular embodiments, the computer application causes the graphical user interface to display a wound status, as shown in FIG. 15A. A wound status explains the current state of the wound in the PUD tool. Three types of statuses are available: "Active, Inactive." For example, a wound status will be active if the pressure ulcer is open which means the wound is in an active open state and the wound is not healed; Alternatively, another wound status would be "inactive" if the wound is healed and no longer present. Only a Stage 1 Pressure Ulcer, Stage 2 Pressure Ulcer, a DTI, and a lesion that has been classified as "not a pressure ulcer"; A wound that was mistakenly entered into the PUD system may be classified as "marked in error"; whereas, only wounds which are considered "closed" and not "healed" when they are resurfaced with 100% scar tissue and/or epithelium such as Stage 4 Pressure Ulcers, Stage 3 Pressure Ulcers, Resurfaced Pressure Ulcers, Unstageable Pressure Ulcers, and Stage Pressure Ulcers will remain "active" at all times, as they are never considered fully healed. This helps prevents reverse staging as well. The user may also edit or enter their own established wound status. For example, the computer application may cause graphical user interface 118 to display a drop-down menu that prompts a user to change the wound status and record a result in the patient's chart, as shown in FIG. 15B.

In particular embodiments, the method prevents classifying wounds that do not meet the criteria of a pressure ulcer as currently established and maintained by the NPUAP, the EPUAP, and adopted by the Center of Medicare and Medicaid Services (CMS), even if the wound and/or lesion is caused by pressure and/or pressure in combination with shear.

In particular embodiments, the method may achieve 100% accuracy in diagnosing pressure injuries.

In particular embodiments, the computer application causes the graphical user interface to display a screen that enables a user to instruct the computer application on recording the diagnosis. A non-limiting example of this feature is shown in FIG. 15A.

In particular embodiments, the computer application causes the graphical user interface to prompt a user to report and/or save the information. A non-limiting example is shown in FIG. 7 and FIG. 8A. As shown in FIG. 7 and FIG. 8A, in some instances, the graphical user interface provides a user with options to export the patient and pressure ulcer data to a spreadsheet (e.g., Excel), export the patient and pressure ulcer data to a PDF file, and/or export the patient and pressure ulcer data to a word processing program (e.g., Word), with additional options (not shown) which allow data to be exported to email, an electronic medical record, a printer, a secure portable data storage device (e.g., encrypted USB thumb drive), or an external hard drive.

In particular embodiments, the computer application causes the medical diagnosis code, classification, location, assessment date and time, wound status, wound condition, the assessment date and time the wound became the currently assigned medical diagnosis code, and/or a treatment recommendation to be stored in the patient data of the data store, and optionally transmits the information to an electronic medical record or other computer program containing information in regards to the patient via the communications interface.

In particular embodiments, the method prevents classifying/diagnosing wounds that are not caused by pressure with the PUD tool.

In particular embodiments, the computer application optionally prevents staging of mucous membrane pressure ulcers.

In particular embodiments, the computer application prevents reverse staging of pressure ulcers.

In particular embodiments, the computer application ensures the necessary information to diagnose and classify a pressure ulcer is provided for the patients' medical record.

In particular embodiments, the method comprises after diagnosing step f), the computer application causes the diagnosis code and/or treatment recommendation to be stored in the patient data of the data store, and optionally transmits the diagnosis code and/or treatment recommendation to an electronic medical record of the patient via the communications interface.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also comprise computer-readable media for carrying or having computer-executable instructions or data structures stored thereon. Such computer-readable media may be any available media which may be accessed by a computer, or downloadable through communication networks. By way of example, and not limitation, such computer-readable media may comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which may be used to carry or store computer program code in the form of computer-executable instructions or data structures and which may be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be comprised within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules comprise routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing various aspects of the described operations, which is not illustrated, comprises a computing device including a processing unit, a system memory, and a system bus that couples various system components including the system memory to the processing unit. The computer will typically comprise one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually comprises an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically comprise many or all of the elements described above relative to the main computer system in which the inventions are embodied. The logical connections between computers comprise a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may comprise a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. A method of classifying decubitus ulcers, comprising the steps of:

capturing an image of a particular wound, wherein the image is captured by an image capture device;

analyzing the image of the particular wound to determine whether one or more criteria of a first stage/grade/category decubitus ulcer are presented by the particular wound;

if the one or more criteria of the first stage/grade/category decubitus ulcer are presented, classifying the particular wound as the first stage/grade/category decubitus ulcer;

if the one or more criteria of a first stage/grade/category decubitus ulcer are not presented, determining whether one or more criteria of a second stage/grade/category decubitus ulcer are presented by the particular wound;

if the one or more criteria of the second stage/grade/category decubitus ulcer are presented, classifying the particular wound as the second stage/grade/category decubitus ulcer;

if the one or more criteria of the second stage/grade/category decubitus ulcer are not presented, taking a predetermined action with respect to the particular wound.

2. The method of claim 1, wherein the predetermined action further comprises a first predetermined action, and wherein the first predetermined action comprises the steps of:

determining whether one or more criteria of a third stage/grade/category decubitus ulcer are presented by the particular wound;

if the one or more criteria of the third stage/grade/category decubitus ulcer are presented, classifying the particular wound as the third stage/grade/category decubitus ulcer; and if the one or more criteria of the third stage/grade/category decubitus ulcer are not presented, taking a second predetermined action with respect to the particular wound.

3. The method of claim 2, wherein the first stage/grade/category decubitus ulcer comprises a Stage 4 decubitus ulcer, the second stage/grade/category decubitus ulcer comprises a Resurfaced Full-Thickness decubitus ulcer, and the third stage/grade/category decubitus ulcer comprises an Unstageable decubitus ulcer.

4. The method of claim 2, wherein the first stage/grade/category decubitus ulcer comprises a Resurfaced Full-Thickness decubitus ulcer, the second stage/grade/category decubitus ulcer comprises an Unstageable decubitus ulcer, and the third stage/grade/category decubitus ulcer comprises a Stage 3 decubitus ulcer.

5. The method of claim 2, wherein the first stage/grade/category decubitus ulcer comprises an Unstageable decubitus ulcer, the second stage/grade/category decubitus ulcer comprises a Stage 3 decubitus ulcer, and the third stage/grade/category decubitus ulcer comprises a Deep Tissue Injury.

6. The method of claim 2, wherein the first stage/grade/category decubitus ulcer comprises a Stage 3 decubitus ulcer, the second stage/grade/category decubitus ulcer comprises a Deep Tissue Injury decubitus ulcer, and the third stage/grade/category decubitus ulcer comprises a Stage 2 decubitus ulcer.

7. The method of claim 2, wherein the first stage/grade/category decubitus ulcer comprises a Deep Tissue Injury, the second stage/grade/category decubitus ulcer comprises a Stage 2 decubitus ulcer, and the third stage/grade/category decubitus ulcer comprises a Stage 1 decubitus ulcer.

8. The method of claim 7, wherein the second predetermined action comprises classifying the particular wound as not a decubitus ulcer.

9. A system for classifying decubitus ulcers, comprising:
an image capture device;
a data store; and
a processor operatively connected to the data store and image capture device, wherein the processor is operative to:
receive an image of a particular wound, wherein the image is captured by the image capture device;
analyze the image of the particular wound to determine whether one or more criteria of a first stage/grade/category decubitus ulcer are presented by the particular wound;
if the one or more criteria of the first stage/grade/category decubitus ulcer are presented, classify the particular wound as the first stage/grade/category decubitus ulcer, store the first stage/grade/category classification in the data store;
if the one or more criteria of a first stage/grade/category decubitus ulcer are not presented, determine whether one or more criteria of a second stage/grade/category decubitus ulcer are presented by the particular wound;
if the one or more criteria of the second stage/grade/category decubitus ulcer are presented, classify the particular wound as the second stage/grade/category decubitus ulcer and store the second stage/grade/category classification in the data store; and if the one or more criteria of the second stage/grade/category decubitus ulcer are not presented, take a predetermined action with respect to the particular wound.

10. The system of claim 9, wherein the predetermined action further comprises a first predetermined action, and wherein, to take the first predetermined action, the processor is further operative to:
determine whether one or more criteria of a third stage/grade/category decubitus ulcer are presented by the particular wound;
if the one or more criteria of the third stage/grade/category decubitus ulcer are presented, classify the particular wound as the third stage/grade/category decubitus ulcer, store the third stage/grade/category classification corresponding to the third stage/grade/category in the data store; and
if the one or more criteria of the third stage/grade/category decubitus ulcer are not presented, take a second predetermined action with respect to the particular wound.

11. The system of claim 9, wherein the first stage/grade/category decubitus ulcer comprises a Stage 4 decubitus ulcer, the second stage/grade/category decubitus ulcer comprises a Resurfaced Full-Thickness decubitus ulcer, and the third stage/grade/category decubitus ulcer comprises an Unstageable decubitus ulcer.

12. The system of claim 9, wherein the first stage/grade/category decubitus ulcer comprises a Resurfaced Full-Thickness decubitus ulcer, the second stage/grade/category decubitus ulcer comprises an Unstageable decubitus ulcer, and the third stage/grade/category decubitus ulcer comprises a Stage 3 decubitus ulcer.

13. The system of claim 9, wherein the first stage/grade/category decubitus ulcer comprises an Unstageable decubitus ulcer, the second stage/grade/category decubitus ulcer comprises a Stage 3 decubitus ulcer, and the third stage/grade/category decubitus ulcer comprises a Deep Tissue Injury.

14. The system of claim 9, wherein the first stage/grade/category decubitus ulcer comprises a Stage 3 decubitus ulcer, the second stage/grade/category decubitus ulcer comprises a Deep Tissue Injury decubitus ulcer, and the third stage/grade/category decubitus ulcer comprises a Stage 2 decubitus ulcer.

15. The system of claim 9, wherein the first stage/grade/category decubitus ulcer comprises a Deep Tissue Injury, the second stage/grade/category decubitus ulcer comprises a Stage 2 decubitus ulcer, and the third stage/grade/category decubitus ulcer comprises a Stage 1 decubitus ulcer.

16. The system of claim 15, wherein, to take the second predetermined action, the processor is further operative to classify the particular wound as not a decubitus ulcer and store the not a decubitus ulcer classification in the data store.

17. A method of classifying decubitus ulcers, comprising the steps of:
receiving an image of a particular wound, wherein the image is captured by an image capture device;
analyzing the image of the particular wound and determining the previous classification of the particular wound based on the image analysis;
determining, in a predefined order of decreasing severity based on the determined previous classification, which one or more symptoms the particular wound presents; and generating, based on the determined one or more symptoms and the determined previous classification, a current classification corresponding to the particular wound.

18. The method of claim 17, wherein the determined previous classification comprises a Stage 4 decubitus ulcer; the one or more symptoms comprise whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and the current classification comprises the Stage 4 decubitus ulcer.

19. The method of claim 17, wherein the determined previous classification comprises a Resurfaced Full-Thickness decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown.

20. The method of claim 17, wherein the determined previous classification comprises an Unstageable decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined.

21. The method of claim 17, wherein the determined previous classification comprises a Stage 3 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining.

22. The method of claim 17, wherein the determined previous classification comprises a Deep Tissue Injury and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red.

23. The method of claim 17, wherein the determined previous classification comprises a Stage 2 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red; and then whether any of the following is currently visible in the particular wound: intact blisters, ruptured blisters, or shallow opened wounds with exposed dermis.

24. The method of claim 17, wherein the determined previous classification comprises a Stage 1 decubitus ulcer and the predefined order comprises whether any of the following are visible in, palpable in, or true of the particular wound: bone, muscle, tendon, ligament, cartilage, fascia, joint capsule, other supporting structures, or the particular wound was previously classified as a Stage 4 decubitus ulcer; and then whether the particular wound is or was closed, is or was resurfaced with scar tissue or epithelium, and the particular wound was previously classified as Unstageable or Unknown; and then whether slough, eschar, or a non-removable dressing is obscuring a portion of the particular wound such that an extent of tissue loss cannot be determined; and then whether any of the following are visible in, palpable in, or true of the particular wound: adipose tissue, granulation tissue, slough, eschar, sinus tract, tunneling, or undermining; and then whether any of the following are visible in, palpable in, or true of the particular wound: blood filled blisters/ruptured blisters surrounded by or adjacent to discolored purple, maroon, or deep red intact skin/intact blister surrounded by or adjacent to non-blanching discolored purple, maroon, or deep red intact skin/intact and non-intact non-blanching discolored purple, maroon, or deep red skin/or skin surrounding or adjacent to the particular wound is non-blanching and discolored purple, maroon, or deep red; and then whether any of the following is currently visible in the particular wound: intact blisters, ruptured blisters, or shallow opened wounds with exposed dermis; and then whether intact skin with non-blanching erythema is currently visible in the particular wound.

* * * * *